US010328084B2

(12) United States Patent
Jeffrey et al.

(10) Patent No.: US 10,328,084 B2
(45) Date of Patent: *Jun. 25, 2019

(54) PYRROLOBENZODIAZEPINES AND TARGETED CONJUGATES

(71) Applicants: SEATTLE GENETICS, INC., Bothell, WA (US); MEDIMMUNE LIMITED, Cambridge, England (GB)

(72) Inventors: Scott Jeffrey, Bothell, WA (US); Patrick Burke, Bothell, WA (US); Philip Wilson Howard, London (GB)

(73) Assignees: SEATTLE GENETICS, INC., Bothell, WA (US); MEDIMMUNE LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/635,063

(22) Filed: Jun. 27, 2017

(65) Prior Publication Data

US 2017/0290924 A1    Oct. 12, 2017

Related U.S. Application Data

(63) Continuation of application No. 15/181,900, filed on Jun. 14, 2016, now Pat. No. 9,713,647, which is a
(Continued)

(51) Int. Cl.
*C07D 471/04* (2006.01)
*C07D 487/04* (2006.01)
(Continued)

(52) U.S. Cl.
CPC .......... *A61K 31/5517* (2013.01); *A61K 47/55* (2017.08); *A61K 47/6803* (2017.08);
(Continued)

(58) Field of Classification Search
CPC .............................. C07D 471/04; C07D 487/04
See application file for complete search history.

(56) References Cited

U.S. PATENT DOCUMENTS 3,361,742 A    1/1968    Julius et al.
3,523,941 A    8/1970    Leimgruber et al.
(Continued)

FOREIGN PATENT DOCUMENTS

EP    1813614    8/2007
FR    2027356    12/1969
(Continued)

OTHER PUBLICATIONS

U.S. Appl. No. 14/774,535, filed Sep. 10, 2015, Howard et al.
(Continued)

*Primary Examiner* — Bruck Kifle
(74) *Attorney, Agent, or Firm* — Casimir Jones, S.C.; Melissa E. Kolom

(57) ABSTRACT

A compound, or a pharmaceutically acceptable salt or solvate thereof, or conjugates thereof, selected from the group consisting of:

(Continued)

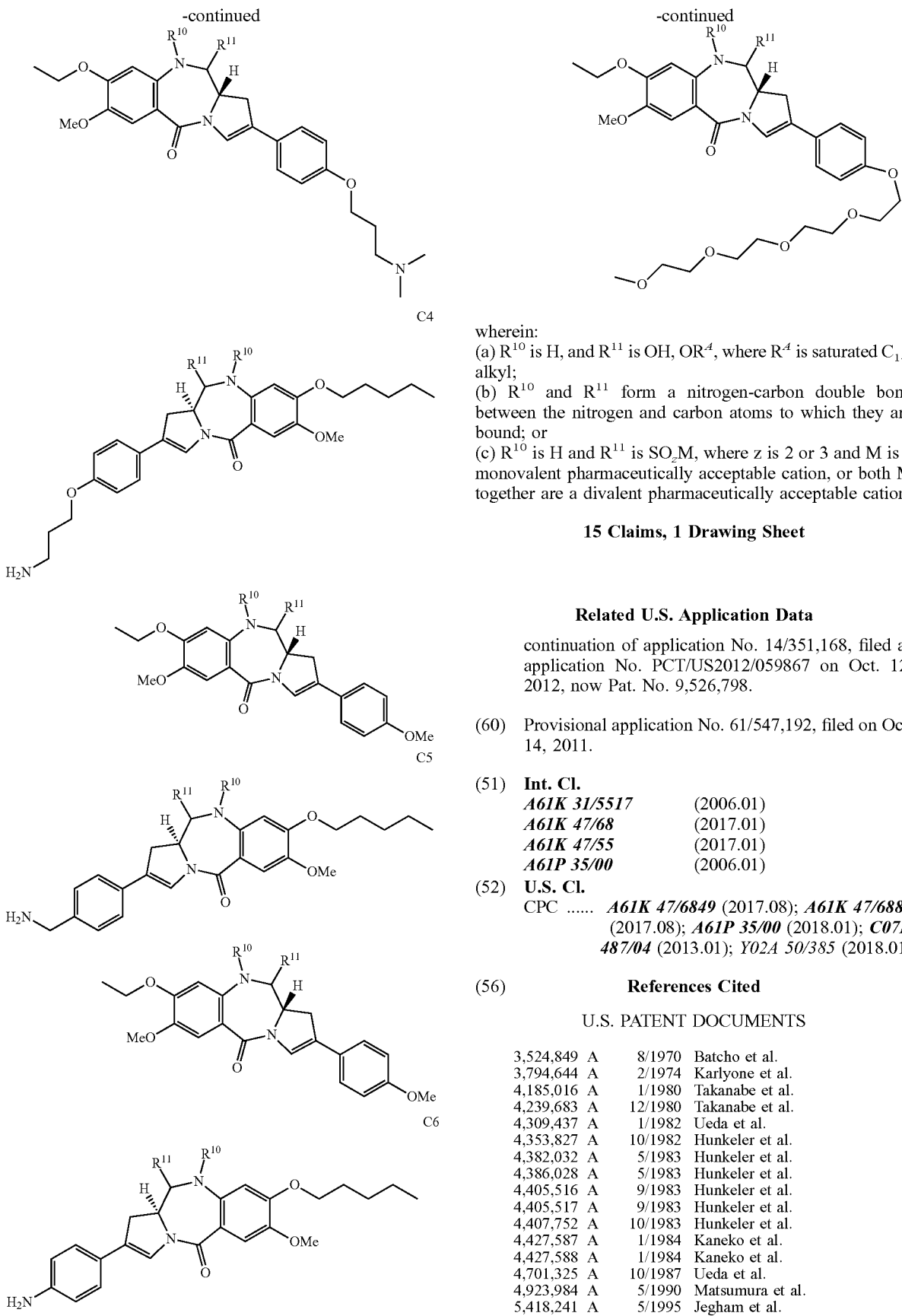

wherein:
(a) $R^{10}$ is H, and $R^{11}$ is OH, $OR^A$, where $R^A$ is saturated $C_{1-4}$ alkyl;
(b) $R^{10}$ and $R^{11}$ form a nitrogen-carbon double bond between the nitrogen and carbon atoms to which they are bound; or
(c) $R^{10}$ is H and $R^{11}$ is $SO_zM$, where z is 2 or 3 and M is a monovalent pharmaceutically acceptable cation, or both M together are a divalent pharmaceutically acceptable cation.

15 Claims, 1 Drawing Sheet

Related U.S. Application Data continuation of application No. 14/351,168, filed as application No. PCT/US2012/059867 on Oct. 12, 2012, now Pat. No. 9,526,798.

(60) Provisional application No. 61/547,192, filed on Oct. 14, 2011.

(51) Int. Cl.
| | | |
|---|---|---|
| *A61K 31/5517* | (2006.01) | |
| *A61K 47/68* | (2017.01) | |
| *A61K 47/55* | (2017.01) | |
| *A61P 35/00* | (2006.01) | |

(52) U.S. Cl.
CPC ...... *A61K 47/6849* (2017.08); *A61K 47/6889* (2017.08); *A61P 35/00* (2018.01); *C07D 487/04* (2013.01); *Y02A 50/385* (2018.01)

(56) References Cited

U.S. PATENT DOCUMENTS

| | | |
|---|---|---|
| 3,524,849 A | 8/1970 | Batcho et al. |
| 3,794,644 A | 2/1974 | Karlyone et al. |
| 4,185,016 A | 1/1980 | Takanabe et al. |
| 4,239,683 A | 12/1980 | Takanabe et al. |
| 4,309,437 A | 1/1982 | Ueda et al. |
| 4,353,827 A | 10/1982 | Hunkeler et al. |
| 4,382,032 A | 5/1983 | Hunkeler et al. |
| 4,386,028 A | 5/1983 | Hunkeler et al. |
| 4,405,516 A | 9/1983 | Hunkeler et al. |
| 4,405,517 A | 9/1983 | Hunkeler et al. |
| 4,407,752 A | 10/1983 | Hunkeler et al. |
| 4,427,587 A | 1/1984 | Kaneko et al. |
| 4,427,588 A | 1/1984 | Kaneko et al. |
| 4,701,325 A | 10/1987 | Ueda et al. |
| 4,923,984 A | 5/1990 | Matsumura et al. |
| 5,418,241 A | 5/1995 | Jegham et al. |
| 6,362,331 B1 | 3/2002 | Kamal et al. |

(56) References Cited

U.S. PATENT DOCUMENTS

| | | |
|---|---|---|
| 6,562,806 B1 | 3/2003 | Thurston et al. |
| 6,608,192 B1 | 8/2003 | Thurston et al. |
| 6,660,742 B2 | 12/2003 | Lee et al. |
| 6,660,856 B2 | 12/2003 | Wang |
| 6,747,144 B1 | 6/2004 | Thurston et al. |
| 6,884,799 B2 | 4/2005 | Kamal et al. |
| 6,909,006 B1 | 6/2005 | Thurston et al. |
| 7,049,311 B1 | 5/2006 | Thurston et al. |
| 7,067,511 B2 | 6/2006 | Thurston et al. |
| 7,244,724 B2 | 7/2007 | Liu et al. |
| 7,265,105 B2 | 9/2007 | Thurston et al. |
| 7,407,951 B2 | 8/2008 | Thurston et al. |
| 7,429,658 B2 | 9/2008 | Howard et al. |
| 7,528,126 B2 | 5/2009 | Howard et al. |
| 7,557,099 B2 | 7/2009 | Howard et al. |
| 7,612,062 B2 | 11/2009 | Gregson et al. |
| 7,704,924 B2 | 4/2010 | Thurston et al. |
| 7,741,319 B2 | 6/2010 | Howard et al. |
| 8,034,808 B2 | 11/2011 | Delavault et al. |
| 8,163,736 B2 | 4/2012 | Gauzy et al. |
| 8,487,092 B2 | 7/2013 | Howard et al. |
| 8,501,934 B2 | 8/2013 | Howard et al. |
| 8,592,576 B2 | 11/2013 | Howard et al. |
| 8,633,185 B2 | 1/2014 | Howard et al. |
| 8,637,664 B2 | 1/2014 | Howard et al. |
| 8,697,688 B2 | 4/2014 | Howard et al. |
| 8,829,184 B2 | 9/2014 | Howard et al. |
| 8,940,733 B2 | 1/2015 | Howard et al. |
| 9,102,704 B2 | 8/2015 | Howard |
| 9,242,013 B2 | 1/2016 | Howard et al. |
| 9,376,440 B2 | 6/2016 | Howard et al. |
| 9,387,259 B2 | 7/2016 | Jeffrey et al. |
| 9,388,187 B2 | 7/2016 | Howard et al. |
| 9,592,240 B2 | 3/2017 | Howard et al. |
| 9,707,301 B2 | 7/2017 | Jeffrey et al. |
| 9,713,647 B2 | 7/2017 | Jeffrey et al. |
| 2003/0195196 A1 | 10/2003 | Thurston et al. |
| 2004/0138269 A1 | 7/2004 | Sun et al. |
| 2004/0198722 A1 | 10/2004 | Thurston et al. |
| 2007/0092940 A1 | 4/2007 | Eigenbrot et al. |
| 2007/0154906 A1 | 7/2007 | Martin et al. |
| 2007/0185336 A1 | 8/2007 | Rossen et al. |
| 2007/0191349 A1 | 8/2007 | Howard et al. |
| 2007/0232592 A1 | 10/2007 | Delavault et al. |
| 2007/0249591 A1 | 10/2007 | Howard et al. |
| 2008/0090812 A1 | 4/2008 | Pepper et al. |
| 2008/0092940 A1 | 4/2008 | Nakajima |
| 2008/0213289 A1 | 9/2008 | Francisco et al. |
| 2009/0148942 A1 | 6/2009 | Mcdonagh et al. |
| 2011/0160192 A1 | 6/2011 | Howard et al. |
| 2011/0256157 A1 | 10/2011 | Howard et al. |
| 2013/0028917 A1 | 1/2013 | Howard et al. |
| 2013/0266595 A1 | 10/2013 | Flygare et al. |
| 2014/0030279 A1 | 1/2014 | Polakis et al. |
| 2014/0030280 A1 | 1/2014 | Polakis |
| 2014/0066435 A1 | 3/2014 | Howard et al. |
| 2014/0120118 A1 | 5/2014 | Howard |
| 2014/0127239 A1 | 5/2014 | Howard |
| 2014/0274907 A1 | 9/2014 | Howard et al. |
| 2014/0286970 A1 | 9/2014 | Jeffrey et al. |
| 2014/0294868 A1 | 10/2014 | Howard et al. |
| 2015/0111880 A1 | 4/2015 | Howard et al. |
| 2015/0126495 A1 | 5/2015 | Howard et al. |
| 2015/0158869 A1 | 6/2015 | Howard |
| 2015/0183883 A1 | 7/2015 | Asundi |
| 2015/0265722 A1 | 9/2015 | Van Berkel |
| 2015/0273077 A1 | 10/2015 | Van Berkel |
| 2015/0273078 A1 | 10/2015 | Van Berkel |
| 2015/0274737 A1 | 10/2015 | Howard et al. |
| 2015/0283258 A1 | 10/2015 | Van Berkel |
| 2015/0283262 A1 | 10/2015 | Van Berkel |
| 2015/0283263 A1 | 10/2015 | Van Berkel |
| 2015/0297746 A1 | 10/2015 | Van Berkel |
| 2015/0315196 A1 | 11/2015 | Howard et al. |
| 2015/0344482 A1 | 12/2015 | Howard et al. |
| 2016/0015828 A1 | 1/2016 | Torgor |
| 2016/0031887 A1 | 2/2016 | Howard et al. |

FOREIGN PATENT DOCUMENTS

| | | |
|---|---|---|
| FR | 2586683 | 3/1987 |
| GB | 1299198 | 12/1972 |
| GB | 2053894 | 2/1981 |
| JP | 53-82792 | 7/1978 |
| JP | 57131791 | 8/1982 |
| JP | 58180487 | 10/1983 |
| WO | WO 92/19620 | 11/1992 |
| WO | WO 93/18045 | 9/1993 |
| WO | WO 95/04718 | 2/1995 |
| WO | WO 00/03291 | 1/2000 |
| WO | WO 00/12506 | 3/2000 |
| WO | WO 00/12507 | 3/2000 |
| WO | WO 00/12508 | 3/2000 |
| WO | WO 00/12509 | 3/2000 |
| WO | WO 01/16104 | 3/2001 |
| WO | WO 2004/043963 | 5/2004 |
| WO | WO 2005/023814 | 3/2005 |
| WO | WO 2005/040170 | 5/2005 |
| WO | WO 2005/042535 | 5/2005 |
| WO | WO 2005/082023 | 9/2005 |
| WO | WO 2005/085177 | 9/2005 |
| WO | WO 2005/085250 | 9/2005 |
| WO | WO 2005/085251 | 9/2005 |
| WO | WO 2005/085259 | 9/2005 |
| WO | WO 2005/085260 | 9/2005 |
| WO | WO 2005/105113 | 11/2005 |
| WO | WO 2005/110423 | 11/2005 |
| WO | WO 2006/111759 | 10/2006 |
| WO | WO 2007/039752 | 4/2007 |
| WO | WO 2007/085930 | 8/2007 |
| WO | WO 2008/010101 | 1/2008 |
| WO | WO 2008/047242 | 4/2008 |
| WO | WO 2008/050140 | 5/2008 |
| WO | WO 2008/070593 | 6/2008 |
| WO | WO 2009/016516 | 2/2009 |
| WO | WO 2009/060208 | 5/2009 |
| WO | WO 2009/060215 | 5/2009 |
| WO | WO 2010/010347 | 1/2010 |
| WO | WO 2010/043877 | 4/2010 |
| WO | WO 2010/043880 | 4/2010 |
| WO | WO 2010/091150 | 8/2010 |
| WO | WO 2011/023883 | 3/2011 |
| WO | WO 2011/038159 | 3/2011 |
| WO | WO 2011/100227 | 8/2011 |
| WO | WO 2011/128650 | 10/2011 |
| WO | WO 2011/130598 | 10/2011 |
| WO | WO 2011/130613 | 10/2011 |
| WO | WO 2011/130616 | 10/2011 |
| WO | WO 2012/112708 | 8/2012 |
| WO | WO 2012/128868 | 9/2012 |
| WO | WO 2013/041606 | 3/2013 |
| WO | WO 2013/053871 | 4/2013 |
| WO | WO 2013/053872 | 4/2013 |
| WO | WO 2013/053873 | 4/2013 |
| WO | WO 2013/055987 | 4/2013 |
| WO | WO 2013/055990 | 4/2013 |
| WO | WO 2013/055993 | 4/2013 |
| WO | WO 2013/164592 | 11/2013 |
| WO | WO 2013/164593 | 11/2013 |
| WO | WO 2014/011518 | 1/2014 |
| WO | WO 2014/011519 | 1/2014 |
| WO | WO 2014/057072 | 4/2014 |
| WO | WO 2014/057073 | 4/2014 |
| WO | WO 2014/057074 | 4/2014 |
| WO | WO 2014/057113 | 4/2014 |
| WO | WO 2014/057114 | 4/2014 |
| WO | WO 2014/057115 | 4/2014 |
| WO | WO 2014/057117 | 4/2014 |
| WO | WO 2014/057118 | 4/2014 |
| WO | WO 2014/057119 | 4/2014 |
| WO | WO 2014/057120 | 4/2014 |
| WO | WO 2014/057122 | 4/2014 |
| WO | WO 2014/022679 | 6/2014 |

(56) References Cited

FOREIGN PATENT DOCUMENTS

| WO | WO 2014/096365 | 6/2014 |
|---|---|---|
| WO | WO 2014/096368 | 6/2014 |
| WO | WO 2014/130879 | 8/2014 |
| WO | WO 2014/140174 | 9/2014 |
| WO | WO 2014/140862 | 9/2014 |
| WO | WO 2014/159981 | 10/2014 |
| WO | WO 2014/174111 | 10/2014 |
| WO | WO 2015/052321 | 4/2015 |
| WO | WO 2015/052322 | 4/2015 |
| WO | WO 2015/052532 | 4/2015 |
| WO | WO 2015/052533 | 4/2015 |
| WO | WO 2015/052534 | 4/2015 |
| WO | WO 2015/052535 | 4/2015 |
| WO | WO 2015/095124 | 6/2015 |
| WO | WO 2015/159076 | 10/2015 |

OTHER PUBLICATIONS

International Search Report and Written Opinion for Application No. PCT/US2011/032664 dated Aug. 19, 2011 (13 pages).
International Search Report and Written Opinion for Application No. PCT/US2012/059867 dated Dec. 28, 2012 (7 pages).
Adair, J.R. et al., "Antibody-drug conjugates—a perfect synergy," Exp. Opin. Biol. Ther. (2012) 16 pages.
Adams et al., "Molecular modelling of a sequence-specific DNA-binding agent based on the pyrrolo [2,1-c][1,4]benzodiazepines," Pharm. Pharmacol. Commun. (1999) 5:555-560.
Aird, R.E. et al., "ABCB1 genetic polymorphism influences the pharmacology of the new pyrrolobenzodiazepine derivative SJG-136," Pharmacogenomics Journal (2008) 8(4):289-296.
Alley, M.C. et al., "SJG-136 (NSC 694501), a novel rationally designed DNA minor groove interstrand cross-linking agent with potent and broad spectrum antitumor activity. Part 2: Efficacy evaluations," Cancer Res. (2004) 64:6700-6706.
Alley, M.C., "Efficacy evaluations of SJG-136 (NSC 694501), a novel pyrrolobenzodiazepine dimer with broad spectrum antitumor activity," Proceedings of the American Association for Cancer Research Annual Meeting (Mar. 2002) 43:63.
Alley et al., 2015, http://ncbi.nlm.nih.gov/pubmed/15374987.
Althius, T. H. and Hess, H. J., "Synthesis and Identification of the Major Metabolites of Prazosin Formed in Dog and Rat," J. Medicinal Chem. (1977) 20(1):146-148.
Antonow, D. et al., "Synthesis of DNA-Interactive Pyrrolo [2,1-c][1,4] benzodiazepines (PBDs)" Chemical Reviews, 2011, 111(4):2815-2864.
Antonow, D. et al.,"Parallel synthesis of a novel C2-aryl pyrrolo [2,1-c][1,4]benzodiazepine (PBD) library," J. Comb. Chem. (2007) 9:437-445.
Arima et al., "Studies on Tomaymycin, a New Antibiotic. I. Isolation and Properties of Tomaymycin," J. Antibiotics (1972) 25:437-444.
Arnould, S., "Impact on the cell cycle and involvement of ATM, ATR, chk1 and chk2 kinases in the cytotoxicity of SJG-136, a new pyrrolobenzodiazepine dimer," Proceedings of the American Association for Cancer Research Annual Meeting (Mar. 2004) 45:1298, Abstract No. 5618.
Arnould, S., "Time-dependent cytotoxicity induced by SJG-136 (NSC 694501): influence of the rate of interstrand cross-link formation on DNA damage signaling," Mol. Canc. Therap. (2006) 5(6):1602-1609.
Banker, G.S. et al., Modern Pharmaceutics, Third edition, Marcel Dekker, New York (1996) 451 and 596.
Baraldi, P.G. et al., "[2,1-c][1,4]benzodiazepine (PBD)-distamycin hybrid inhibits DNA binding to transcription factor Sp1," Nucleotides and Nucleic Acids (2000) 19(8):1219-1229.
Berge et al., "Pharmaceutical Salts," J. Pharm. Sci. (1977) 66:1-19.
Berry, J. M. et al., "Solid-phase synthesis of DNA-interactive pyrrolo[2,1-c][1,4]benzodiazepines," Tetrahedron Letters (2000) 41:6171-6174.
Bose et al., "New Approaches to Pyrrolo[2,1-c][1,4]benzodiazepines: Synthesis, DNA-binding and cytotoxicity of DC-81," Tetrahedron, 48, 751-758 (1992).
Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.
Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).
Breast-cancer, 2015, http://www.breastcancer.org/treatment/chemotherapy/medicines.
Burrow, S.A., "LC-MS/MS assay and dog pharmacokinetics of the dimeric pyrrolobenzodiazepine SJG-136 (NSC 694501)," J. Chromat. B: Anal. Tech. Biomed. Life Sci. (2006) 840(1):56-62.
Burke, P.J. et al., "Anti-CD70 antibody-drug conjugates containing pyrrolobenzodiazepine dimers demonstrate robust antitumor activity," AACR National Meeting, Apr. 2012, Chicago, Illinois, Abstract No. 4631.
Burke, P.J. et al., "Novel immunoconjugates comprised of streptonigrin and 17-amino-geldanamycin attached via a dipeptide-p-aminobenzylamine linker system," Bioorg. Med. Chem. Lett., Apr. 2009, 19(10):2650-2653.
Calcutt, M. W., "Determination of chemically reduced pyrrolobenzodiazepine SJG-136 in human plasma by HPLC-MS/MS: application to an anticancer phase I dose escalation study," J. Mass Spectrom. (2008) 43(1):42-52.
Chen, Z. et al., "A novel approach to the synthesis of cytotoxic C2—C3 unsaturated pyrrolo[2,1-c][1,4]benzodiazepines (PBDs) with conjugated acrylyl C2-substituents," Biorg. Med. Chem. Lett. (2004) 14:1547-1549.
Cheung, A., "Direct liquid chromatography determination of the reactive imine SJG-136 (NSC 694501)," J. Chromat. B: Anal. Techn. Biomed. Life Sci. (2005) 822(1-2):10-20.
Cipolla, L., "Pyrrolo[2,1-c][1,4]benzodiazepine as a scaffold for the design and synthesis of anti-tumour drugs," Anti-Cancer Agents in Medicinal Chemistry (Jan. 2009) 9(1):1-31.
Clingen, P.H., "The role of nucleotide excision repair and homologous recomination in the sensitivity of mammalian cells to the minor groove crosslinking pyrrolo[2,1-c][1,4]benzodiazepine dimer SJG-136 (NSC694501)," Proceedings of the American Association for Cancer Research Annual Meeting (Jul. 2003) 44:524.
Clingen, P.H., "The XPF-ERCC1 endonuclease and homologous recombination contribute to the repair of minor groove DNA interstrand crosslinks in mammalian cells produced by the pyrrolo[2,1-c][1,4]benzodiazepine dimer SJG-136," Nucl. Acids Res. (2005) 33(10):3283-3291.
Cooper, N. et al., "Synthesis of novel PBDs as anti-tumour agents," Chem. Commun. (2002) 16:1764-1765.
Cooper, N., "Design, Synthesis and Evaluation of Novel C2-Aryl Pyrrolobenzodiazepines as Potential Anticancer Agents," Thesis submitted to School of Pharmacy, University of London, Dated Oct. 5, 2006.
Courtney, S. M. et al., "A new convenient procedure for the synthesis of pyrrolo[2,1-c][1,4]benzodiazepines", Tetrahedron Letters, vol. 34, No. 33, 5327-28 (1993).
Dattolo, G. et al., "Polycondensed nitrogen heterocycles. IX. 5,6-dihydro-7H-pyrrolo[1,2-d][1,4]benzodiazepin-6-one," J. Heterocyclic. Chem. (1980) 17:701-703.
Dong, Q. et al., "Reductive cleavage of TROC groups under neutral conditions with cadmium-lead couple," Tetrahedron Lett. (1995) 36(32):5681-5682.
Doronina, S.O. et al., "Development of potent monoclonal antibody auristatin conjugates for cancer therapy," Nature Biotech. (2003) 21:778-784.
Dorwald, F.Z., Side Reactions in Organic Synthesis: a Guide to Successful Synthesis Design, Weinheim: Wiley-VCH Verlag GmbH & Co., KGaA (2005) Preface.
Doyle, M., "Response of Staphylococcus aureus to subinhibitory concentrations of a sequence-selective, DNA minor groove cross-linking pyrrolobenzodiazepine dimer," J. Antimicrob. Chemo., Aug. 2009, 64(5):949-959.

(56) References Cited

OTHER PUBLICATIONS

Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem. (2002) 13, 855-869.
Dupont, C. et al., "Synthesis of rhazinilam analogue acting as an inhibitor of tubulin assembly," Tetrahedron Lett. (2000) 41:5853-5856.
Farmer, J.D. et al., "Synthesis and DNA crosslinking ability of a dimeric anthramycin analog" Tetrahedron Letters (1988) 29(40):5105-5108, Abstract only.
Farmer, J.D. et al., "DNA binding properties of a new class of linked anthramycin analogs,", Chemical Abstracts, Abstract No. 239940r, vol. 114, No. 25, 25 899-903 (1991).
Fey, T. et al., "Silica-supported TEMPO catalyst: synthesis and application in the anelli oxidation of alcohols," J. Org. Chem. (2001) 66:8154-8159.
Firsching, A. et al., "Antiproliferative and angiostatic activity of suramin analogues," Cancer Res. (1995) 55:4957-4961.
Foloppe, M.P. et al., "DNA-binding properties of pyrrolo[2,1-c][1,4]benzodiazephine N10—C11 amidines," Eur. J. Med. Chem., 31, 407-410 (1996).
Fujisawa Pharmaceutical Co., Ltd., Abstract No. 139983k, "Benzodiazepine derivatives", Chemical Abstracts, vol. 99, No. 17, 603 (1983).
Fujisawa Pharmaceutical Co., Ltd., Abstract No. 72145x, "Benzodiazepine derivatives", Chemical Abstracts, vol. 98, No. 9, 638 (1983).
Fukuyama, T. et al., "Total Synthesis of (+)-Porothramycin B," Tetrahedron Letters, vol. 34, 16, 2577-2580 (1993).
Gallmeier, E., "Targeted disruption of FANCC and FANCG in human cancer provides a preclinical model for specific therapeutic options," Gastroenterology (2006) 130(7):2145-2154.
Gavezzotti, A., "Are crystal structures predictable?" Acc. Chem. Res. (1994) 27:309-314.
Greene, T.W. And Wuts, P.G.M., *Protective Groups in Organic Synthesis*, John Wiley & Sons, 2nd ed., Ch 7, 315-345 (1991).
Greene, T.W. et al., Protective Groups in Organic Synthesis, John Wiley & Sons (1999) 3rd Edition, 23-200, 503-549, 633-647.
Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.
Gregson, S.J. et al., "Linker length modulates DNA cross-linking reactivity and cytotoxic potency of C8/C8' ether-linked C2-exo-unsaturated pyrrolo [2,1-c][1,4]benzodiazepine (PBD) dimers," J. Med. Chem. (2004) 1161-1174.
Gregson, S.J. et al., "Synthesis of the first example of a C2—C3/C2'—C3'-endo unsaturated pyrrolo [2,1-c]0 [1,4]benzodiazepine dimer," Biorg. Med. Chem. Lett. (2001) 11:2859-2862.
Gregson, S.J. et al., "Synthesis of the first examples of A-C8/C—C2 amide-linked pyrrolo [2,1-c][1,4]benzodiazepine dimers," Biorg. Med. Chem. Lett. (2003) 13:2277-2280.
Gregson, S.J. et al., "Design, Synthesis and Evaluation of a Novel Pyrrolobenzodiazepine DNA-Interactive Agent with Highly Efficient Cross-Linking Ability and Potent Cytotoxicity", J. Med. Chem., 44: 737-748 (2001).
Gregson, S.J. et al., "Effect of C2-exo Unsaturation on the Cytotoxicity and DNA-Binding Reactivity of Pyrrolo[2,1-c][1,4]benzodiazepines", Bioorganic & Medicinal Chemistry Letters, 10: 1845-1847 (2000).
Guichard, S.M., "Influence of P-glycoprotein expression on in vitro cytotoxicity and in vivo antitumour activity of the novel pyrrolobenzodiazepine dimer SJG-136," Eur. J. Cancer (2005) 41(12):1811-1818.
Guiotto, A. et al., "Synthesis of novel C7-aryl substituted pyrrolo [2,1-c][1,4]benzodiazepines (PBDs) via Pro-N10-troc protection and suzuki coupling," Bioorganic & Medicinal Chemistry Letters, 8, No. 21, 3017-3018 (1998).
Hadjivassileva, T., "Antibacterial activity of pyrrolobenzodiazepine dimers, a novel group of DNA-binding compounds," Abstracts of the Interscience Conference on Antimicrobial Agents and Chemotherapy (Oct.-Nov. 2004) 44:202.
Hadjivassileva, T., "Interactions of pyrrolobenzodiazepine dimers and duplex DNA from methicillin-resistant *Staphylococcus aureus*," Int. J. Antimicrob. Agents (2007) 29(6):672-678.
Hadjivassileva, T., "Pyrrolobenzodiazepine dimers: novel sequence-selective, DNA-interactive, cross-linking agents with activity against Gram-positive bacteria," J. Antimicrob. Chemo. (2005) 56(3):513-518.
Hamaguchi, A., "DNA cross-linking and in vivo antitumour activity of the extended pyrrolo[2,1-c][1,4]benzodiazepine dimer SG2057 (DRG-16)," EJC Supplements (Nov. 2006) 4(12):96.
Hara et al., "DC 102, a new glycosidic pyrrolo(1,4)benzodiazepine antibiotic produced by *Streptomyces* sp.", J. Antibiotics, 41, 702-704 (1988).
Hartley, J.A. et al., "SG2285, a novel C2-aryl-substituted pyrrolobenzodiazepine dimer prodrug that cross-links DNA and exerts highly potent antitumor activity," Cancer Res., Sep. 2010, 70(17):6849-6858.
Hartley, J.A. et al., "SJG-136 (NSC 694501), a novel rationally designed DNA minor groove interstrand cross-linking agent with potent and broad spectrum antitumor activity. Part 1: Cellular pharmacology, in vitro and initial in vivo antitumor activity," Cancer Res. (2004) 64:6693-6699.
Hartley, J.A., "In vitro antitumor activity and in vivo DNA interstrand crosslinking by the novel pyrrolobenzodiazepine dimer SJG-136 (NSC 694501)," Proceedings of the American Association for Cancer Research Annual Meeting (Mar. 2002) 43:489.
Hartley, J.A., "SJG-136 (NSC-D694501)—a novel DNA sequence specific minor groove crosslinking agent with significant antitumor activity," Proceedings of the American Association for Cancer Research Annual Meeting (Mar. 2000) 41:425.
Hochhauser, D., "Phase I study of sequence-selective minor groove DNA binding agent SJG-136 inpatients with advanced solid tumors," Clin. Cancer Res., Mar. 2009, 15(6):2140-2147.
Hochlowski, J. et al., "Abbeymycin, a new anthramycin-type antibiotic produced by a streptomycete," J. Antibiotics, 40, 145-148 (1987).
Howard, P.W. et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W. et al., "Synthesis of a novel C2/C2'-aryl-substituted pyrrolo [2,1-c][1,4]benzodiazepine dimer prodrug with improved water solubility and reduced DNA reaction rate," Bioorg. Med. Chem., Sep. 2009, In Press, 4 pages now: Sep. 2009, 19:6463-6466.
Howard, P.W. et al., "The design, synthesis and biological evaluation of a set of C2-aryl substituted pyrrolo [2,1-c][1,4]benzodiazepine dimers," EJC Supplements (2006) 4(12):95—Poster Abstract 301.
Howard, P.W., "Design, synthesis and biological evaluation of novel C2-aryl-substituted pyrrolo [2,1-c][1,4]benzodiazepine monomers," Proceedings of the American Association for Cancer Research Annual Meeting (Apr. 2006) 47:132.
Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," Acc. Chem. Res., 19, 230-237 (1986).
Itoh et al., "Sibanomicin, a new pyrrolo(1,4)benzodiazepine antitumor antibiotic produced by a *Micromonospora* sp." J. Antibiotics, 41, 1281-1284 (1988).
Janjigian, Y.Y., "A phase I trial of SJG-136 (NSC#694501) in advanced solid tumors," Cancer Chemotherapy and Pharmacology , Aug. 2009, 65(5):833-838.
Jeffrey, S.C. et al., "Development of Pyrrolobenzodiazepine-Based Antibody-Drug Conjugates for Cancer," AACR Annual Meeting 2013, Abstract No. 4321.

(56) References Cited

OTHER PUBLICATIONS

Jeffrey, S.C., "Design, synthesis, and in vitro evaluation of dipeptide-based antibody minor groove binder conjugates," J. Med. Chem. (2005) 48(5):1344-1358.

Jia, L., "Interspecies differences in pharmacokinetics and time-dissociated toxicokinetics of SJG-136," Proceedings of the American Association for Cancer Research Annual Meeting (Mar. 2004) 45:487.

Jia, L., "Use of the comet assay as a surrogate biomarker for the in vivo measurement of DNA damage to lymphocytes," Proceedings of the American Association for Cancer Research Annual Meeting (Mar. 2004) 45:452-453.

Jordan, V.C., "Tamoxifen: a most unlikely pioneering medicine," Nature Reviews: Drug Discovery (2003) 2:205-213.

Kamal et al., "Synthesis and DNA-binding affinity of A-C8/C—C2 alkoxyamido-linked pyrrolo [2,1-c][1,4]benzodiazepine dimers" Biorg. Med. Chem. Lett. (2003) 13(22):3955-3958.

Kamal, A. et al., "Design, synthesis and evaluation of new noncross-linking pyrrolobenzodiazepine dimers with efficient DNA binding ability and potent antitumor activity," J. Med. Chem. (2002) 45:4679-4688.

Kamal, A., "Development of pyrrolo[2,1-c][1,4]benzodiazepine beta-galactoside prodrugs for selective therapy of cancer by ADEPT and PMT," Chemmedchem (2008) 3:794-802.

Kamal, A., "Remarkable DNA binding affinity and potential anticancer activity of pyrrolo [2,1-c][1,4]benzodiazepine-naphthalamide conjugates linked through piperazine side-armed alkane spacers," Bioorg. Med. Chem. (2008) 16(15):7218-7224.

Kamal, A., "Remarkable enhancement in the DNA-binding ability of C2-fluoro substituted pyrrolo [2,1-c][1,4]benzodiazepines and their anticancer potential," Bioorg. Med. Chem., Jan. 2009, 17(4):1557-1572.

Kamal, A., "Synthesis of fluorinated analogues of SJG-136 and their DNA-binding potential," Bioorg. Med. Chem. Lett (2004) 14(22):5699-5702.

Kamal, A., et al., "An Efficient Synthesis of Pyrrolo[2,1-c][1,4] Benzodiazepine Antibiotics via Reductive Cyclization," Bioorg. Med. Chem. Ltrs, 7, No. 14, 1825-1828 (1997).

Kamal, A., et al., "Synthesis of Pyrrolo [2,1-c][1,4]-Benzodiazepene Antibiotics: Oxidation of Cyclic Secondary Amine with TPAP", Tetrahedron, v. 53, No. 9, 3223-3230 (1997).

Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.

Kaneko, T. et al., "Bicyclic and tricyclic analogues of anthramycin," J. Med. Chem. (1985) 28:388-392.

Kang, G.-D. et al., "Synthesis of a novel C2-aryl substituted 1,2-unsaturated pyrrolobenzodiazepine," Chem. Commun (2003) 1688-1689.

Kohn, K., "Anthramycin," Antibiotics III, Springer-Verlag NY, 3-11 (1975).

Konishi, M. et al., "Chicamycin, a new antitumor antibiotic II. Structure determination of chicamycins A and B," J. Antibiotics, 37, 200-206 (1984).

Kunimoto et al., "Mazethramycin, a new member of anthramycin group antibiotics," J. Antibiotics, 33, 665-667.

Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).

Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.

Leber, J.D. et al., "A revised structure for sibiromycin," J. Am. Chem. Soc., 110, 2992-2993 (1988).

Leimgruber, W. et al., "Isolation and characterization of anthramycin, a new antitumor antibiotic," J. Am. Chem. Soc., 87, 5791-5793 (1965).

Leimgruber, W. et al., "The structure of anthramycin," J. Am. Chem. Soc., 87, 5793-5795 (1965).

Leimgruber, W. et al., "Total synthesis of anthramycin," J. Am. Chem. Soc., 90, 5641-5643 (1968).

Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.

Marin, D., "Voltammetric studies of the interaction of pyrrolo [2,1-c][1,4]benzodiazepine (PBD) monomers and dimers with DNA," J. Electroanal. Chem. (2006) 593(1-2):241-246.

Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.

Mori, M. et al., "Total syntheses of prothracarcin and tomaymycin by use of palladium catalyzed carbonylation," Tetrahedron (1986) 42(14):3793-3806.

Mountzouris, J.A. et al., "Comparison of a DSB-120 DNA interstrand cross-linked adduct with the corresponding bis-Tomamycin adduct," J. Med. Chem. (1994) 37:3132-3140.

Nagasaka, T. and Koseki, Y, "Stereoselective Synthesis of Tilivalline," Journal of Organic Chemistry, vol. 63, No. 20, 6797-6801 (1998).

Nagasaka, T. et al., "Stereoselective Synthesis of Tilivalline," Tetrahedron Letters, 30:14, 1871-1872 (1989).

Narayanaswamy, M., "A novel HPLC/MS assay to measure DNA interstrand cross-linking efficacy in oligonucleotides of varying sequence," EJC Supplements (Nov. 2006) 4(12):92-93.

Narayanaswamy, M., "An assay combining high-performance liquid chromatography and mass spectrometry to measure DNA interstrand cross-linking efficiency in oligonucleotides of varying sequences," Anal. Biochem. (2008) 374(1):173-181.

Narayanaswamy, M., "Use of HPLC-MS to characterize novel mono and intrastrand cross-linked DNA adducts formed by the sequence-selective DNA-interactive agent SJG-136," Proceedings of the American Association for Cancer Research Annual Meeting (Apr. 2007) 48:760-761.

Narukawa, Y., "General and efficient synthesis of 2-alkylcarbapenems synthesis of dethia carba analogs of clinically useful carbapenems via palladium-catalyzed cross-coupling reaction," Tetrahedron (1997) 53:539-556.

O'Neil, Chemical Abstract No. 171573p, "The synthesis of Functionalized Pyrrolo-[2,1-c][1,4]-Benzodiazepines", Chemical Abstracts, vol. 126, No. 13, 618 (1997).

O'Neil, I.A., et al., "The Synthesis of Functionalized Pyrrolo-[2,1-c][1,4]-Benzodiazepines," Synlett, 75-78 (1997).

O'Neil, I.A. et al., "DPPE: A Convenient Replacement for Triphenylphosphine in the Staudinger and Mitsunobu Reactions", Tetrahedron Letters, vol. 39, No. 42, 7787-7790 (1998).

Pepper, C., "Fludarabine-mediated suppression of the excision repair enzyme ERCC1 contributes to the cytotoxic synergy with the DNA minor groove crosslinking agent SJG-136 (NSC 694501) in chronic lymphocytic leukaemia cells," Br. J. Cancer (2007) 97(2):253-259.

Pepper, C.J. et al., "The novel sequence-specific DNA cross-linking agent SJG-136 (NSC 694501) has potent and selective in vitro cytotoxicity in human B-cell chronic lymphocytic leukemia cells with evidence of a p53-independent mechanism of cell kill," Cancer Res. (2004) 64:6750-6755.

Puzanov, I., "Phase I and pharmacokinetic trial of SJG-136 administered on a daily x5 schedule," EJC Supplements (Nov. 2006) 4(12):93.

Quintas-Cardama, A., "Sequencing of subcloned PCR products facilitates earlier detetction of BCR-ABL1 and other mutants compared to direct sequencing of the ABL1 kinase domain," Leukemia (2008) 22(4):877-878.

Rahman, K.M., "Effect of microwave irradiation on covalent ligand-DNA interactions," Chem. Commun. (Cambridge, UK), Apr. 2009, 20:2875-2877.

(56) References Cited

OTHER PUBLICATIONS

Rahman, K.M., "Rules of DNA adduct formation for pyrrolobenzodiazepine (PBD) dimers," Proceedings of the American Association for Cancer Research Annual Meeting (Apr. 2010) 51:851.
Rahman, K.M., "The pyrrolobenzodiazepine dimer SJG-136 forms sequence-dependent intrastrand DNA cross-lins and monoalkylated adducts in addition to interstrand cross-links," J. Am. Chem. Soc., Sep. 2009, 131(38):13756-13766.
Reid, J.M., "LC-MS/MS assay and rat pharmacokinetics and metabolism of the dimeric pyrrolobenzodiazepine SJG-136," Proceedings of the American Association for Cancer Research Annual Meeting (Mar. 2004) 45:1248.
Rich, I.N., "Validation and development of a predictive paradigm for hemotoxicology using a multifunctional bioluminescence colony-forming proliferation assay," Toxicological Sci. (2005) 87(2):427-441.
Sagnou, M.J. et al., "Design and Synthesis of Novel Pyrrolobenzodiazepine (PDB) Prodrugs for ADEPT and GDEPT," *Bioorganic & Medicinal Chemistry Letters*, 10, 2083-2086 (2000).
Schweikart, K., "In vitro myelosuppression of SJG-136, a pyrrolobenzodiazepine dimer: comparison to bizelesin," Proceedings of the American Association for Cancer Research Annual Meeting (Mar. 2004) 45:486.
Shimizu et al., "Prothracarcin, a novel antitumor antibiotic," The Journal of Antibiotics (1982) 29, 2492-2503.
Shimizu, K et al., "Prothracarcin, a Novel Antitumor Antibiotic," *J. Antibiotics*, 35, 972-978 (1982).
Smellie, M. et al., "Cellular pharmacology of novel C8-linked anthramycin-based sequence-selective DNA minor groove cross-linking agents," Br. J. Cancer (1994) 70:48-53.
Smellie, M. et al., "Sequence selective recognition of duplex DNA through covalent interstrand cross-linking," Biochem. (2003) 42:8232-8239.
Souillac, P. et al., "Chracterization of delivery systems, differential scanning calorimetry," Encyclopedia of Controlled Drug Delivery (1999) 212-227 (pp. 217-218).
Suggitt, M., "The hollow fibre model—facilitating anti-cancer pre-clinical pharmacodynamics and improving animal welfare," Int. J. Oncol. (2006) 29(6):1493-1499.
Suggs, J.W. et al., "Synthesis and structure of anthramycin analogs via hydride reduction of dilactams," *Tetrahedron Letters*, 26, No. 40, 4871-4874 (1985).
Sutherland, M.S.K. et al., "SGN-CD33A: a novel CD33-directed antibody-drug conjugate, utilizing pyrrolobenzodiazepine dimers, demonstrates preclinical anti-tumor activity against multi-drug resistant human AML," American Society of Hematology (Dec. 8-12, 2012) Atlanta, Georgia, Abstract No. 3589.
Takeuchi, T. et al., "Neothramycins A and B, New Antitumor Antibiotics," *J. Antibiotics*, 29, 93-96 (1976).
Tercel, M. et al., "Unsymmetrical DNA cross-linking agents: combination of the CBI and PBD pharmacophores," J. Med. Chem. (2003) 46:2132-2151.
Thurston, D. E., "Advances in the study of Pyrrolo [2,1-c][1,4] benzodiazepine (PBD) Antitumour Antibiotics", *Molecular Aspects of Anticancer Drug-DNA Interaction*, Neidle, S. and Waring M.J., Eds.; Macmillan Press Ltd, 1:54-88 (1993).
Thurston, D.E. and Bose, D.S., "Synthesis of DNA-Interactive Pyrrolo[2,1-c][1,4]benzodiazepines," *Chem. Rev.*, 94:433-465 (1994).
Thurston, D.E. and Thompson, A.S., "The molecular recognition of DNA," Chem. Brit., 26, 767-772 (1990).
Thurston, D.E. et al., "Effect of A-ring modifications on the DNA-binding behavior and cytotoxicity of pyrrolo[2,1-c][1,4]benzodiazepines", *Journal of Medicinal Chemistry*, 42:1951-1964 (1999).
Thurston, D.E. et al., "Synthesis of Sequence-selective C8-linked Pyrrolo [2,1-c][1,4] Benzodiazepine DNA Interstrand Cross-linking Agent," J. Org. Chem., 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting therapeutic strategies for the 21st century," Brit. J. Cancer (1999) 80(1):65-85.
Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.
Tiberghien, A.C., "Application of the stille coupling reaction to the synthesis of C2-substituted endo-exo unsaturated pyrrolo[2,1-c][1,4]benzodiazepines (PBDs)," Bioorg. Med. Chem. Lett. (2008) 18(6):2073-2077.
Tozuka et al., "Studies on tomaymycin. II. Total synthesis of the antitumor antibiotics, E-and Z-tomaymycins," J. Antibiotics (Tokyo) (1983) 36:276-282.
Tsunakawa, M. et al., "Porothramycin, a new antibiotic of the anthramycin group: Production, isolation, structure and biological activity," *J. Antibiotics*, 41:1366-1373 (1988).
Umezawa, H. et al., Chemical Abstract No. 4427a, "Mazethramycins" *Chemical Abstracts*, vol. 90, No. 1, 428 (1979).
Vippagunta, S.R. et al., "Crystalline solids," Adv. Drug Delivery Rev. (2001) 48:3-26.
Wang, J.H., "Determination of antitumor agent MG-136 in human serum by HPLC with tandem mass spectrometric detection (HPLC-MS/MS)," Abstracts of Papers American Chemical Society (Mar. 13, 2005) 229(1):U119.
Weidner-Wells, M.A. et al., "Photochemical approach to the synthesis of the pyrrolo[1,4]benzodiazepine antibiotics," J. Org. Chem. (1989) 54:5746-5758.
Wells, G. et al., "Design, synthesis and biophysical and biological evaluation of a series of pyrrolobenzodiazepine-poly(N-methylpyrrole) conjugates," J. Med. Chem. (2006) 49:5442-5461.
Wilkinson, G.P., "Pharmacokinetics and intracellular pharmacological characteristics of the novel pyrrolobenzodiazepine (PBD) dimer SJG-136," Proceedings of the American Association for Cancer Research Annual Meeting (Jul. 2003) 44:320.
Wilkinson, G.P., "Pharmacokinetics, metabolism and glutathione reactivity of SJG-136," Br. J. Cancer (2003) 88(Supp. 1): S29.
Wilkinson, G.P., "Preliminary pharmacokinetic and bioanalytical studies of SJG-136 (NSC 694501), a sequence-selective pyrrolobenzodiazepine dimer DNA-cross-linking agent," Investigational New Drugs (2004) 22(3):231-240.
Wilson, S.C. et al., "Design and Synthesis of a Novel Epoxide-Containing Pyrrolo [2,1-c][1,4]benzodiazepine (PBD) via a New Cyclization Procedure," *Tetrahedron Letters*, 36, No. 35, 6333-6336 (1995).
Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine Systeni", *J. Med. Chem.* 42:4028-4041 (1999).
Wolff, M.E., Burger's Medicinal Chemistry, 4th Edition, Part I, Wiley: New York (1979) 336-337.
Wolff, M.E., Burger's Medicinal Chemistry, 5th Edition, Part I, John Wiley & Sons (1995) 975-977.
Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.
Xie, G. et al., "Bisindolylmaleimides linked to DNA minor groove binding lexitropsins: synthesis, inhibitory activity against topoisomeraseI, and biological evaluation," J. Med. Chem. (1996) 39:1049-1055.

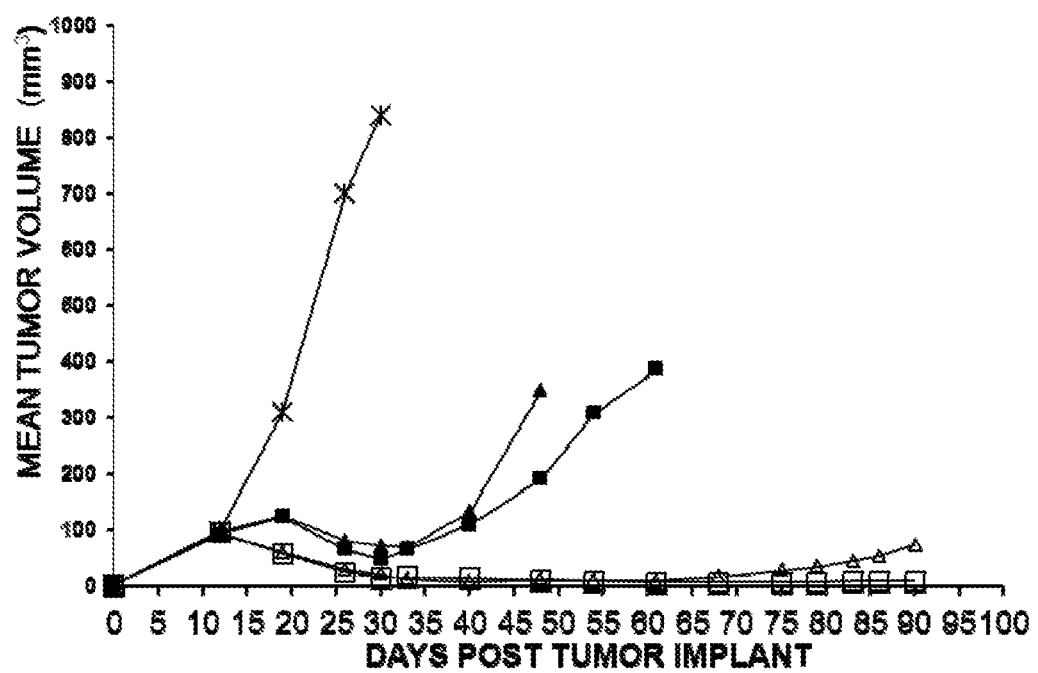

PYRROLOBENZODIAZEPINES AND TARGETED CONJUGATES

CROSS-REFERENCE TO RELATED APPLICATIONS

This is a continuation of U.S. patent application Ser. No. 15/181,900, filed on Jun. 14, 2016, which is a continuation of U.S. patent application Ser. No. 14/351,168, filed on Apr. 11, 2014, now U.S. Pat. No. 9,526,798, which is a U.S. national stage entry of International Patent Application No. PCT/US2012/059867, filed on Oct. 12, 2012, which claims priority to U.S. Provisional Patent Application No. 61/547,192, filed on Oct. 14, 2011, the entire contents of each of which are fully incorporated herein by reference.

The present invention relates to pyrrolobenzodiazepines (PBDs), in particular pyrrolobenzodiazepine dimers having a C2-C3 double bond and an aryl group at the C2 position in each monomer unit, and their inclusion in targeted conjugates.

BACKGROUND TO THE INVENTION

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and numerous synthetic routes have been developed to a variety of analogues (Thurston, et al., *Chem. Rev.* 1994, 433-465 (1994); Antonow, D. and Thurston, D. E., *Chem. Rev.* 2011 111 (4), 2815-2864). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102)(Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

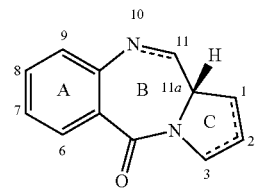

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III.* Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

It has been previously disclosed that the biological activity of these molecules can be potentiated by joining two PBD units together through their C8/C'-hydroxyl functionalities via a flexible alkylene linker (Bose, D. S., et al., *J. Am. Chem. Soc.*, 114, 4939-4941 (1992); Thurston, D. E., et al., *J. Org. Chem.*, 61, 8141-8147 (1996)). The PBD dimers are thought to form sequence-selective DNA lesions such as the palindromic 5'-Pu-GATC-Py-3' interstrand cross-link (Smellie, M., et al., *Biochemistry*, 42, 8232-8239 (2003); Martin, C., et al., *Biochemistry*, 44, 4135-4147) which is thought to be mainly responsible for their biological activity. One example of a PBD dimmer, SG2000 (SJG-136):

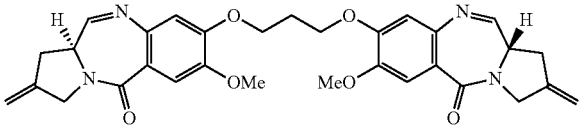

has recently entered Phase II clinical trials in the oncology area (Gregson, S., et al., *J. Med. Chem.*, 44, 737-748 (2001); Alley, M. C., et al., *Cancer Research*, 64, 6700-6706 (2004); Hartley, J. A., et al., *Cancer Research*, 64, 6693-6699 (2004)).

More recently, the present inventors have previously disclosed in WO 2005/085251, dimeric PBD compounds bearing C2 aryl substituents, such as SG2202 (ZC-207):

ZC-207

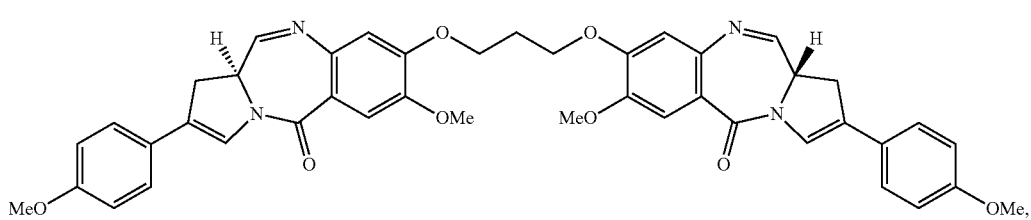

and in WO2006/111759, bisulphites of such PBD compounds, for example SG2285 (ZC-423):

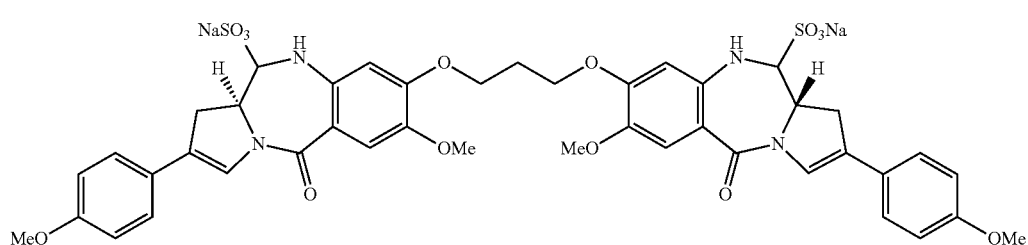

ZC-423

These compounds have been shown to be highly useful cytotoxic agents (Howard, P. W., et al., *Bioorg. Med. Chem.* (2009), 19 (22), 6463-6466, doi: 10.1016/j.bmcl.2009.09.012).

Due to the manner in which these highly potent compounds act in cross-linking DNA, these molecules have been made symmetrically. This provides for straightforward synthesis, either by constructing the PBD moieties simultaneously having already formed the dimer linkage, or by reacting already constructed PBD moieties with the dimer linking group.

WO 2010/043880 discloses unsymmetrical dimeric PBD compound bearing aryl groups in the C2 position of each monomer, where one of these aryl groups bears a substituent designed to provide an anchor for linking the compound to another moiety. Co-pending International application PCT/US2011/032664, filed 15 Apr. 2011, discloses the inclusion of these PBD dimer compounds in targeted conjugates.

DISCLOSURE OF THE INVENTION

The present inventors have developed further specific unsymmetrical dimeric PBD compounds for inclusion in targeted conjugates. These compounds may have advantages in their preparation and use, particularly in their biological properties and the synthesis of conjugates, and the biological properties of these conjugates.

The present invention comprises a compound, or a pharmaceutically acceptable salt or solvate thereof, selected from the group consisting of:

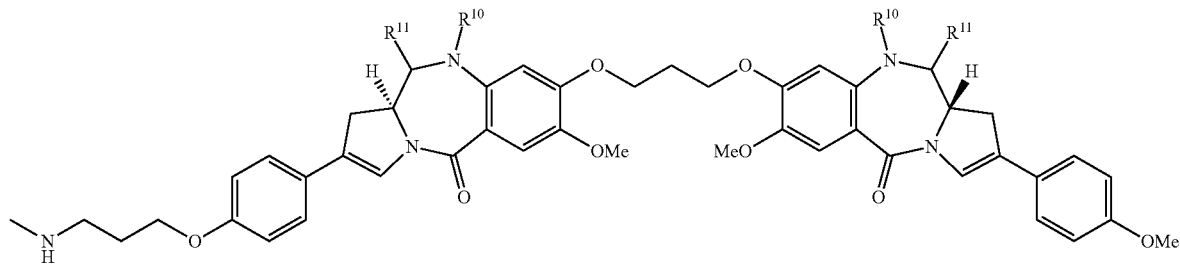

C1

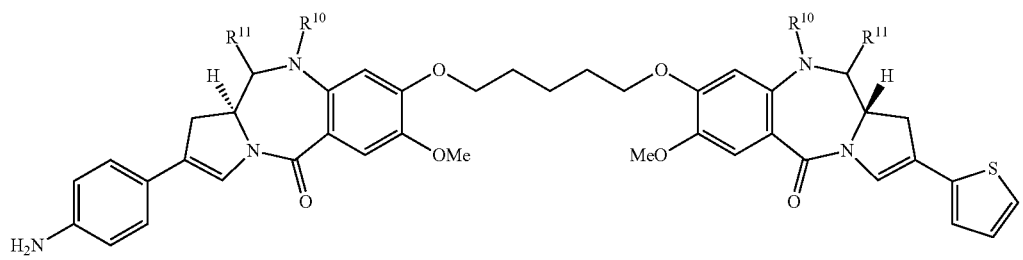

C2

-continued
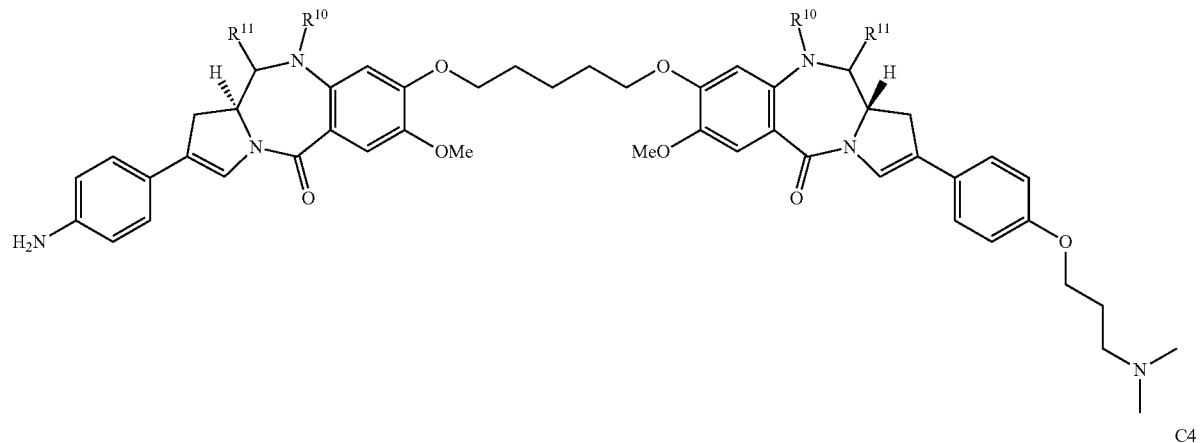
C3
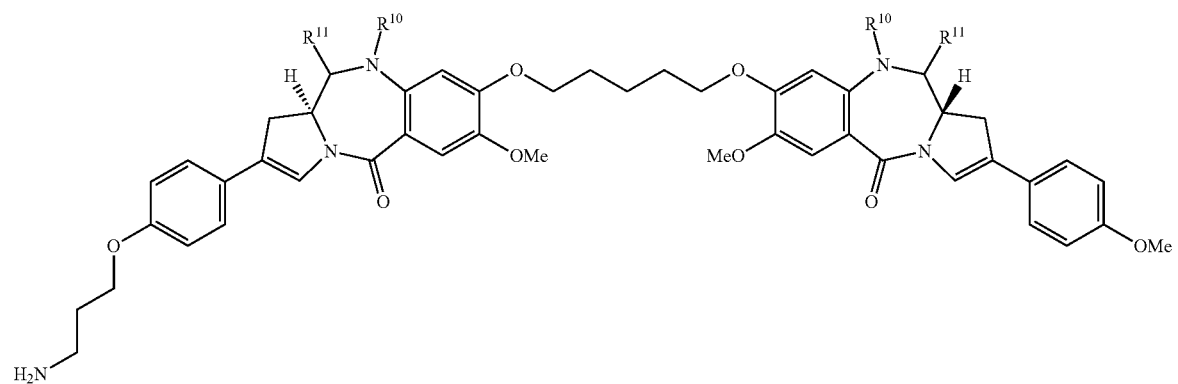
C4
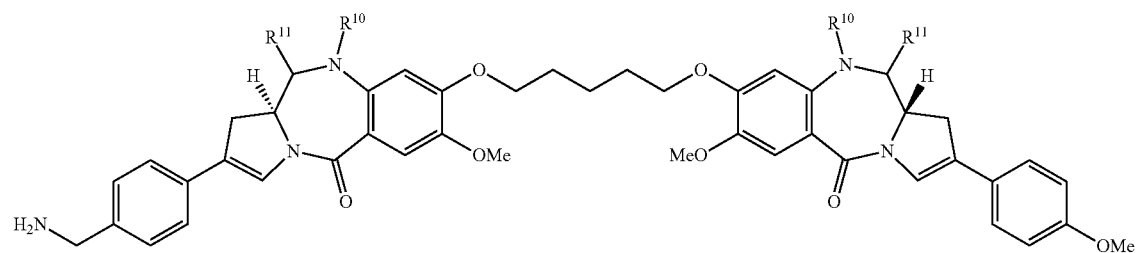
C5
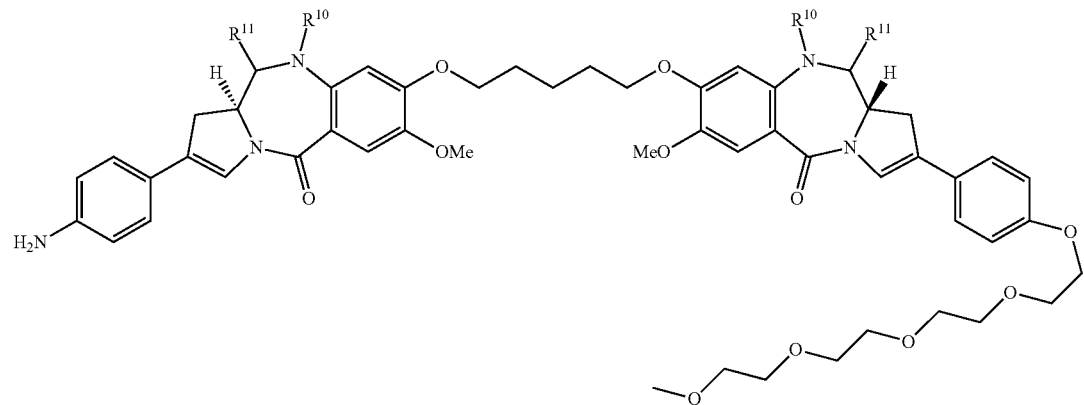
C6 wherein either:

(a) $R^{10}$ is H, and $R^{11}$ is OH or $OR^A$, where $R^A$ is saturated $C_{1-4}$ alkyl; or (b) $R^{10}$ and $R^{11}$ form a nitrogen-carbon double bond between the nitrogen and carbon atoms to which they are bound; or (c) $R^{10}$ is H and $R^{11}$ is $SO_zM$, where z is 2 or 3 and M is a monovalent pharmaceutically acceptable cation, or both M together are a divalent pharmaceutically acceptable cation.

A second aspect of the present invention provides the use of a compound of the first aspect of the invention in the manufacture of a medicament for treating a proliferative disease. The second aspect also provides a compound of the first aspect of the invention for use in the treatment of a proliferative disease.

One of ordinary skill in the art is readily able to determine whether or not a candidate conjugate treats a proliferative condition for any particular cell type. For example, assays which may conveniently be used to assess the activity offered by a particular compound are described in the examples below.

A third aspect of the present invention comprises a compound according to the first aspect of the invention, except where either:

(a) $R^{10}$ is carbamate nitrogen protecting group, and $R^{11}$ is O-Prot°, wherein Prot° is an oxygen protecting group; or (b) $R^{10}$ is a hemi-aminal nitrogen protecting group and $R^{11}$ is an oxo group.

A fourth aspect of the present invention comprises a method of making a compound of the first aspect, or a pharmaceutically acceptable salt or solvate thereof, from a compound of the third aspect, or a pharmaceutically acceptable salt or solvate thereof, by deprotection of the imine bond.

The unsymmetrical dimeric PBD compounds of the present invention are made by different strategies to those previously employed in making symmetrical dimeric PBD compounds. In particular, the present inventors have developed a method which involves adding each each C2 substituent to a symmetrical PBD dimer core in separate method steps. Accordingly, a fifth aspect of the present invention provides a method of making a compound of the first or third aspect of the invention, comprising at least one of the method steps set out below.

In a sixth aspect, the present invention relates to Conjugates comprising dimers of PBDs linked to a targeting agent, wherein the PBD dimer is a compound as described herein, or a pharmaceutically acceptable salt or solvate thereof (supra).

In some embodiments, the Conjugates have the following formula IV:

$$L\text{-}(LU\text{-}D)_p \tag{IV}$$

or a pharmaceutically acceptable salt or solvate thereof, wherein L is a Ligand unit (i.e., a targeting agent), LU is a Linker unit and D is a Drug unit that is a PBD dimer (see below). The subscript p is from 1 to 20. Accordingly, the Conjugates comprise a Ligand unit covalently linked to at least one Drug unit by a Linker unit. The Ligand unit, described more fully below, is a targeting agent that binds to a target moiety. The Ligand unit can, for example, specifically bind to a cell component (a Cell Binding Agent) or to other target molecules of interest. Accordingly, the present invention also provides methods for the treatment of, for example, various cancers and autoimmune disease. These methods encompass the use of the Conjugates wherein the Ligand unit is a targeting agent that specifically binds to a target molecule. The Ligand unit can be, for example, a protein, polypeptide or peptide, such as an antibody, an antigen-binding fragment of an antibody, or other binding agent, such as an Fc fusion protein.

In the conjugates of the present invention, the PBD dimer D is selected from the group consisting of:

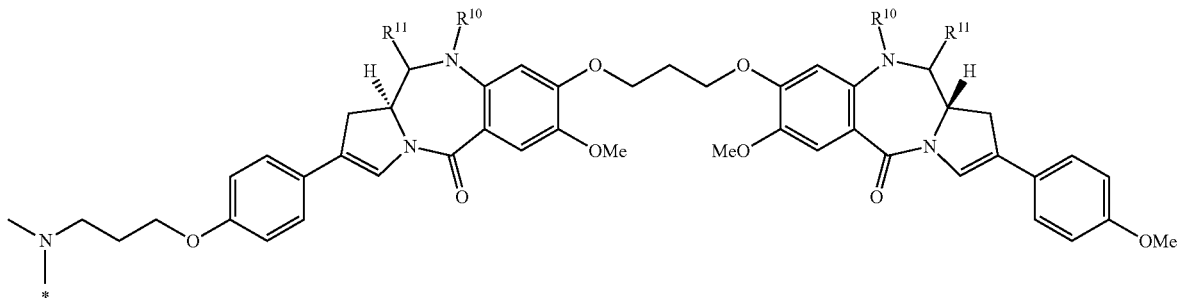

D1

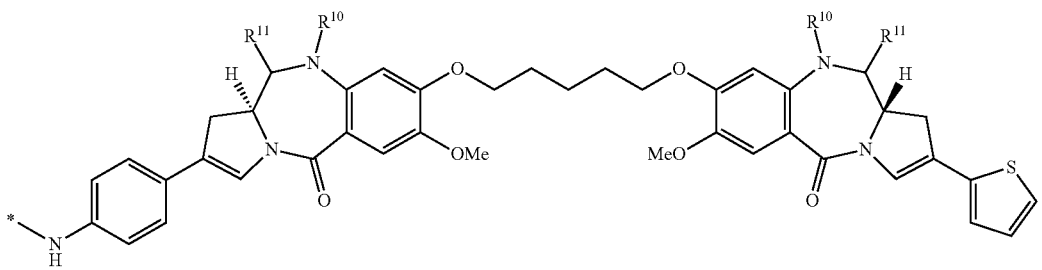

D2

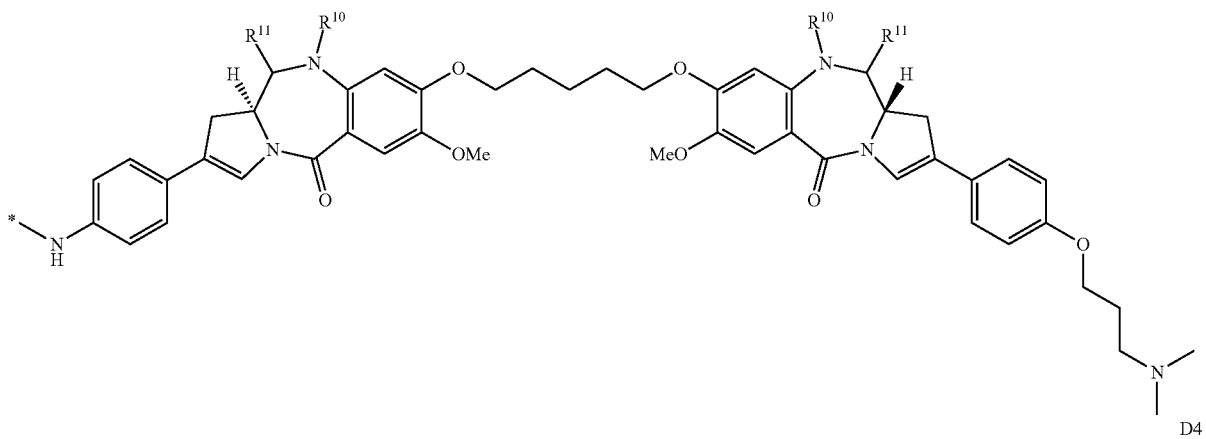
D3
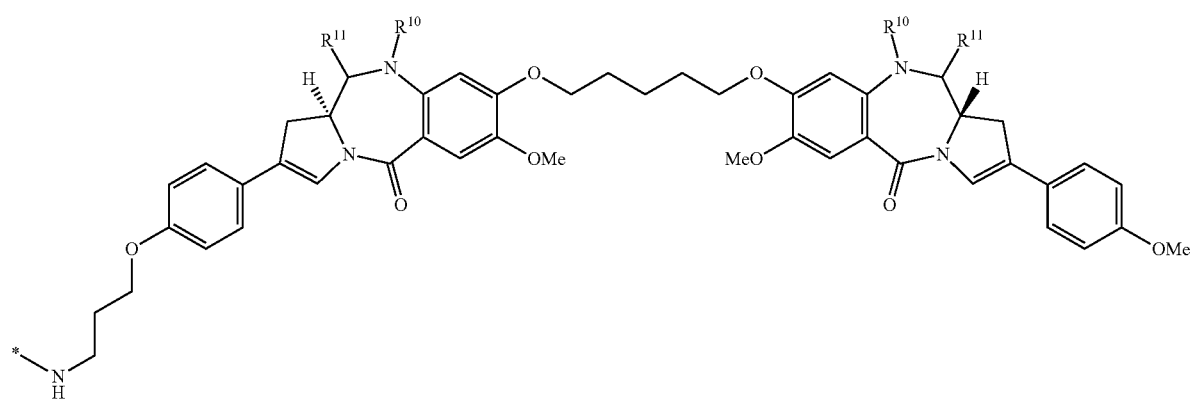
D4
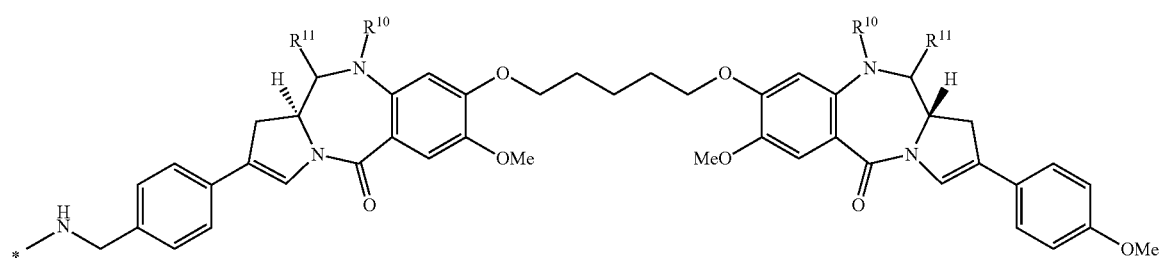
D5
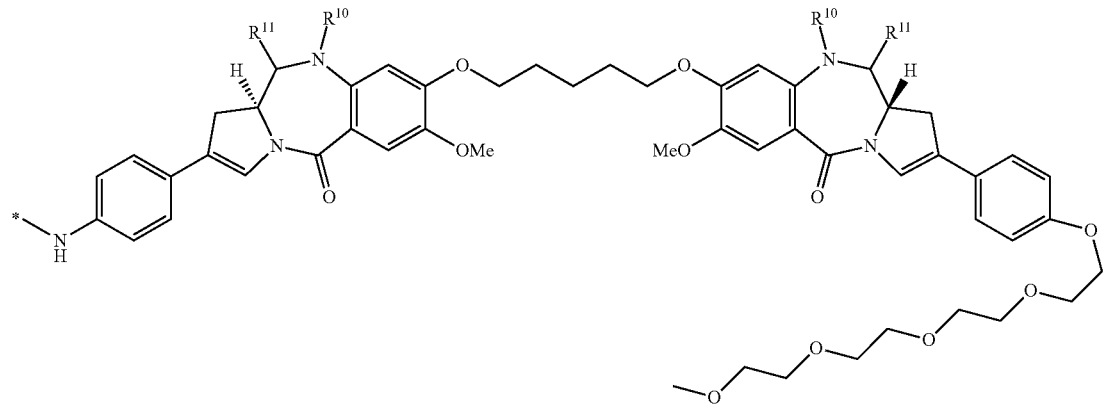
D6
or a pharmaceutically acceptable salt or solvate thereof, where $R^{10}$ and $R^{11}$ are as defined in the first aspect, and the asterix indicates the point of attachment to the Linker Unit.
The drug loading is represented by p, the number of drug molecules per Ligand unit (e.g., an antibody). Drug loading may range from 1 to 20 Drug units (D) per Ligand unit (e.g., Ab or mAb). For compositions, p represents the average drug loading of the Conjugates in the composition, and p ranges from 1 to 20.

In some embodiments, p is from about 1 to about 8 Drug units per Ligand unit. In some embodiments, p is 1. In some embodiments, p is 2. In some embodiments, p is from about 2 to about 8 Drug units per Ligand unit. In some embodiments, p is from about 2 to about 6, 2 to about 5, or 2 to about 4 Drug units per Ligand unit. In some embodiments, p is about 2, about 4, about 6 or about 8 Drug units per Ligand unit.

The average number of Drugs units per Ligand unit in a preparation from a conjugation reaction may be characterized by conventional means such as mass spectroscopy, ELISA assay, and HPLC. The quantitative distribution of Conjugates in terms of p may also be determined. In some instances, separation, purification, and characterization of homogeneous Conjugates, where p is a certain value, from Conjugates with other drug loadings may be achieved by means such as reverse phase HPLC or electrophoresis.

In a seventh aspect, the present invention relates to Linker-Drug compounds (i.e., Drug-Linkers) comprising dimers of PBDs (see above) linked to a linking unit. These Drug-linkers can be used as intermediates for the synthesis of Conjugates comprising dimers of PBDs linked to a targeting agent.

These Drug-Linkers have the following formula V:

$$LU\text{-}D \qquad (V)$$

or a pharmaceutically acceptable salt or solvate thereof, wherein LU is a Linker unit and D is a Drug unit that is a PBD dimer, as defined in the sixth aspect of the invention.

FIGURE

The FIGURE shows the effect on mean tumour volume following treatment with two conjugates of the present invention.

DEFINITIONS

Pharmaceutically Acceptable Cations

Examples of pharmaceutically acceptable monovalent and divalent cations are discussed in Berge, et al., *J. Pharm. Sci.*, 66, 1-19 (1977), which is incorporated herein by reference in its entirety and for all purposes.

The pharmaceutically acceptable cation may be inorganic or organic.

Examples of pharmaceutically acceptable monovalent inorganic cations include, but are not limited to, alkali metal ions such as $Na^+$ and $K^+$. Examples of pharmaceutically acceptable divalent inorganic cations include, but are not limited to, alkaline earth cations such as $Ca^{2+}$ and $Mg^{2+}$. Examples of pharmaceutically acceptable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Groups

The term "saturated $C_{1-4}$ alkyl" as used herein, pertains to a monovalent moiety obtained by removing a hydrogen atom from a carbon atom of a hydrocarbon compound having from 1 to 4 carbon atoms, which may be aliphatic or alicyclic. Similarly, the term "saturated $C_{1-2}$alkyl" as used herein, pertains to a monovalent moiety obtained by removing a hydrogen atom from a carbon atom of a hydrocarbon compound having from 1 to 2 carbon atoms, i.e. methyl or ethyl.

Examples of saturated alkyl groups include, but are not limited to, methyl ($C_1$), ethyl ($C_2$), propyl ($C_3$), and butyl ($C_4$)

Examples of saturated linear alkyl groups include, but are not limited to, methyl ($C_1$), ethyl ($C_2$), n-propyl ($C_3$) and n-butyl ($C_4$).

Examples of saturated branched alkyl groups include iso-propyl ($C_3$), iso-butyl ($C_4$), sec-butyl ($C_4$) and tert-butyl ($C_4$).

Oxo (keto, -one): $=O$.

Oxygen protecting group: the term "oxygen protecting group" refers to a moiety which masks a hydroxy group, and these are well known in the art. A large number of suitable groups are described on pages 23 to 200 of Greene, T. W. and Wuts, G. M., Protective Groups in Organic Synthesis, $3^{rd}$ Edition, John Wiley & Sons, Inc., 1999, which is incorporated herein by reference in its entirety and for all purposes. Classes of particular interest include silyl ethers (e.g. TMS, TBDMS), substituted methyl ethers (e.g. THP) and esters (e.g. acetate).

Carbamate nitrogen protecting group: the term "carbamate nitrogen protecting group" pertains to a moiety which masks the nitrogen in the imine bond, and these are well known in the art. These groups have the following structure:

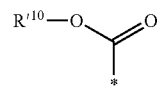

wherein $R'^{10}$ is R as defined below. A large number of suitable groups are described on pages 503 to 549 of Greene, T. W. and Wuts, G. M., Protective Groups in Organic Synthesis, $3^{rd}$ Edition, John Wiley & Sons, Inc., 1999, which is incorporated herein by reference in its entirety and for all purposes.

Hemi-aminal nitrogen protecting group: the term "hemi-aminal nitrogen protecting group" pertains to a group having the following structure:

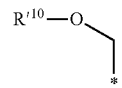

wherein $R'^{10}$ is R as defined below. A large number of suitable groups are described on pages 633 to 647 as amide protecting groups of Greene, T. W. and Wuts, G. M., Protective Groups in Organic Synthesis, $3^{rd}$ Edition, John Wiley & Sons, Inc., 1999, which is incorporated herein by reference in its entirety and for all purposes.

R

R is selected from optionally substituted $C_{1-12}$ alkyl, $C_{3-20}$ heterocyclyl and $C_{5-20}$ aryl groups.

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). The term "$C_{1-4}$ alkyl" as used herein, pertains to a monovalent moiety obtained by removing a hydrogen atom from a carbon atom of a hydrocarbon compound having from 1 to 4 carbon atoms, which may be aliphatic or alicyclic, and which may be saturated or unsaturated (e.g. partially unsaturated, fully unsaturated). Similarly, the term "$C_{1-2}$alkyl" as used herein, pertains to a monovalent moiety obtained by removing a hydrogen atom from a carbon atom of a hydrocarbon compound having from 1 to 2 carbon atoms, i.e. methyl or ethyl.

Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —C($CH_3$)=$CH_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —$CH_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);
$O_3$: trioxane ($C_6$);
$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);
$O_1S_1$: oxathiole ($C_5$) and oxathiane (thioxane) ($C_6$); and,
$N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. The term "$C_{5-7}$ aryl", as used herein, pertains to a monovalent moiety obtained by removing a hydrogen atom from an aromatic ring atom of an aromatic compound, which moiety has from 5 to 7 ring atoms and the term "$C_{5-10}$ aryl", as used herein, pertains to a monovalent moiety obtained by removing a hydrogen atom from an aromatic ring atom of an aromatic compound, which moiety has from 5 to 10 ring atoms. Preferably, each ring has from 5 to 7 ring atoms.

In this context, the prefixes (e.g. $C_{3-20}$, $C_{5-7}$, $C_{5-6}$, $C_{5-10}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.
Hydroxy: —OH.
Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH($OR^1$)($OR^2$), wherein $R^1$ and $R^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, $R^1$ and $R^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)($OR^1$), wherein $R^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR($OR^1$)($OR^2$), where $R^1$ and $R^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)($OR^1$), where $R^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.
Thione (thioketone): =S.
Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.
Acyl (keto): —C(=O)R, wherein R is an acyl substituent, for example, a $C_{1-7}$ alkyl group (also referred to as $C_{1-7}$alkylacyl or $C_{1-7}$alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.
Thiocarboxy (thiocarboxylic acid): —C(=S)SH.
Thiolocarboxy (thiolocarboxylic acid): —C(=O)SH.
Thionocarboxy (thionocarboxylic acid): —C(=S)OH.
Imidic acid: —C(=NH)OH.
Hydroxamic acid: —C(=NOH)OH.
Ester (carbon/late, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a C$_{1-7}$ alkyl group, a C$_{3-20}$ heterocyclyl group, or a C$_{5-20}$ aryl group, preferably a C$_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a C$_{1-7}$ alkyl group, a C$_{3-20}$ heterocyclyl group, or a C$_{5-20}$ aryl group, preferably a C$_{1-7}$ alkyl group.

Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a C$_{1-7}$ alkyl group (also referred to as C$_{1-7}$ alkylamino or di-C$_{1-7}$alkylamino), a C$_{3-20}$ heterocyclyl group, or a C$_{5-20}$ aryl group, preferably H or a C$_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group, and R$^2$ is an acyl substituent, for example, a C$_{1-7}$ alkyl group, a C$_{3-20}$ heterocyclyl group, or a C$_{5-20}$aryl group, preferably hydrogen or a C$_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

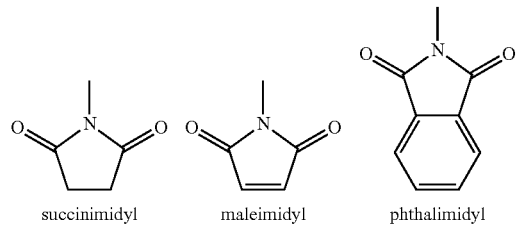

succinimidyl    maleimidyl    phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

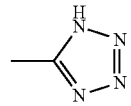

Imino: =NR, wherein R is an imino substituent, for example, for example, hydrogen, a C$_{1-7}$ alkyl group, a C$_{3-20}$ heterocyclyl group, or a C$_{5-20}$ aryl group, preferably H or a C$_{1-7}$alkyl group. Examples of imino groups include, but are not limited to, =NH, =NMe, and =NEt.

Amidine (amidino): —C(=NR)NR$_2$, wherein each R is an amidine substituent, for example, hydrogen, a C$_{1-7}$ alkyl group, a C$_{3-20}$ heterocyclyl group, or a C$_{5-20}$ aryl group, preferably H or a C$_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.
Thioether (sulfide): —SR, wherein R is a thioether substituent, for example, a C$_{1-7}$ alkyl group (also referred to as a C$_{1-7}$alkylthio group), a C$_{3-20}$ heterocyclyl group, or a C$_{5-20}$ aryl group, preferably a C$_{1-7}$ alkyl group. Examples of C$_{1-7}$alkylthio groups include, but are not limited to, —SCH$_3$ and —SCH$_2$CH$_3$.

Disulfide: —SS—R, wherein R is a disulfide substituent, for example, a C$_{1-7}$ alkyl group, a C$_{3-20}$ heterocyclyl group, or a C$_{5-20}$ aryl group, preferably a C$_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a $C_{1-7}$ alkyl group, a $C_{3-20}$ heterocyclyl group, or a $C_{5-20}$ aryl group, preferably a $C_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$ alkyl group, a $C_{3-20}$ heterocyclyl group, or a $C_{5-20}$ aryl group, preferably a $C_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$ C$_6$H$_5$.

Sulfinamino: —NR$^1$S(=O)R, wherein R$^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH$_3$ and —N(CH$_3$)S(=O) C$_6$H$_5$.

Phosphino (phosphine): —PR$_2$, wherein R is a phosphino substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$ alkyl group, a $C_{3-20}$ heterocyclyl group, or a $C_{5-20}$ aryl group, preferably a $C_{1-7}$ alkyl group or a $C_{5-20}$ aryl group. Examples of phosphinyl groups include, but are not limited to, —P(=O) (CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2{}_2$, where R$^1$ and R$^2$ are phosphoramidite substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2{}_2$, where R$^1$ and R$^2$ are phosphoramidate substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group.

Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Conjugates

The present invention provides Conjugates comprising a PBD dimer connected to a Ligand unit via a Linker unit. In one embodiment, the Linker unit includes a Stretcher unit (A), a Specificity unit ($L^1$), and a Spacer unit ($L^2$). The Linker unit is connected at one end to the Ligand unit (L) and at the other end to the PBD dimer compound (D).

In one aspect, such a Conjugate is shown below in formula IVa:

(IVa)

or a pharmaceutically acceptable salt or solvate thereof, wherein:

L is the Ligand unit; and

-$A^1_a$-$L^1_s$-$L^2_y$- is a Linker unit (LU), wherein:

-$A^1$- is a Stretcher unit, a is 1 or 2,

-$L^1$- is a Specificity unit, s is an integer ranging from 0 to 12,

-$L^2$- is a Spacer unit, y is 0, 1 or 2;

-D is a PBD dimer; and p is from 1 to 20.

In another aspect, such a Conjugate is shown below in formula IVb:

(IVb)

Also illustrated as:

(IVb)

or a pharmaceutically acceptable salt or solvate thereof, wherein:

L is the Ligand unit; and

-$A^1_a$-$L^1_s$($L^2_y$)- is a Linker unit (LU), wherein:

-$A^1$- is a Stretcher unit linked to a Stretcher unit ($L^2$), a is 1 or 2,

-$L^1$- is a Specificity unit linked to a Stretcher unit ($L^2$), s is an integer ranging from 0 to 12, -$L^2$- is a Spacer unit, y is 0, 1 or 2;

-D is a PBD dimer; and p is from 1 to 20.

Preferences

The following preferences may apply to all aspects of the invention as described above, or may relate to a single aspect. The preferences may be combined together in any combination.

In one embodiment, the Conjugate has the formula:

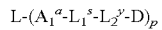

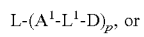

or a pharmaceutically acceptable salt or solvate thereof, wherein L, $A^1$, a, $L^1$, s, $L^2$, D, y and p are as described above.

In one embodiment, the Ligand unit (L) is a Cell Binding Agent (CBA) that specifically binds to a target molecule on the surface of a target cell. An exemplary formula is illustrated below:

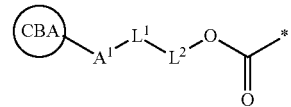

where the asterisk indicates the point of attachment to the Drug unit (D), CBA is the Cell Binding Agent, $L^1$ is a Specificity unit, $A^1$ is a Stretcher unit connecting $L^1$ to the Cell Binding Agent, $L^2$ is a Spacer unit, which is a covalent bond, a self-immolative group or together with —OC(=O)— forms a self-immolative group, and $L^2$ is optional. —OC(=O)— may be considered as being part of $L^1$ or $L^2$, as appropriate.

In another embodiment, the Ligand unit (L) is a Cell Binding Agent (CBA) that specifically binds to a target molecule on the surface of a target cell. An exemplary formula is illustrated below:

where the asterisk indicates the point of attachment to the Drug unit (D), CBA is the Cell Binding Agent, $L^1$ is a Specificity unit, $A^1$ is a Stretcher unit connecting $L^1$ to the Cell Binding Agent, $L^2$ is a Spacer unit which is a covalent bond or a self-immolative group, and a is 1 or 2, s is 0, 1 or 2, and y is 0 or 1 or 2.

In the embodiments illustrated above, $L^1$ can be a cleavable Specificity unit, and may be referred to as a "trigger" that when cleaved activates a self-immolative group (or self-immolative groups) $L^2$, when a self-immolative group(s) is present. When the Specificity unit $L^1$ is cleaved, or the linkage (i.e., the covalent bond) between $L^1$ and $L^2$ is cleaved, the self-immolative group releases the Drug unit (D).

In another embodiment, the Ligand unit (L) is a Cell Binding Agent (CBA) that specifically binds to a target molecule on the surface of a target cell. An exemplary formula is illustrated below:

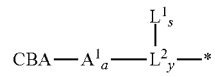

where the asterisk indicates the point of attachment to the Drug (D), CBA is the Cell Binding Agent, $L^1$ is a Specificity unit connected to $L^2$, $A^1$ is a Stretcher unit connecting $L^2$ to the Cell Binding Agent, $L^2$ is a self-immolative group, and a is 1 or 2, s is 1 or 2, and y is 1 or 2.

In the various embodiments discussed herein, the nature of $L^1$ and $L^2$ can vary widely. These groups are chosen on the basis of their characteristics, which may be dictated in part, by the conditions at the site to which the conjugate is delivered. Where the Specificity unit $L^1$ is cleavable, the structure and/or sequence of $L^1$ is selected such that it is cleaved by the action of enzymes present at the target site (e.g., the target cell). $L^1$ units that are cleavable by changes in pH (e.g. acid or base labile), temperature or upon irradiation (e.g. photolabile) may also be used. $L^1$ units that are cleavable under reducing or oxidising conditions may also find use in the Conjugates.

In some embodiments, $L^1$ may comprise one amino acid or a contiguous sequence of amino acids. The amino acid sequence may be the target substrate for an enzyme.

In one embodiment, $L^1$ is cleavable by the action of an enzyme. In one embodiment, the enzyme is an esterase or a peptidase. For example, $L^1$ may be cleaved by a lysosomal protease, such as a cathepsin.

In one embodiment, $L^2$ is present and together with —C(=O)O— forms a self-immolative group or self-immolative groups. In some embodiments, —C(=O)O— also is a self-immolative group.

In one embodiment, where $L^1$ is cleavable by the action of an enzyme and $L^2$ is present, the enzyme cleaves the bond between $L^1$ and $L^2$, whereby the self-immolative group(s) release the Drug unit.

$L^1$ and $L^2$, where present, may be connected by a bond selected from:
—C(=O)NH—,
—C(=O)O—,
—NHC(=O)—,
—OC(=O)—,
—OC(=O)O—,
—NHC(=O)O—,
—OC(=O)NH—,
—NHC(=O)NH, and
—O—(a glycosidic bond).

An amino group of $L^1$ that connects to $L^2$ may be the N-terminus of an amino acid or may be derived from an amino group of an amino acid side chain, for example a lysine amino acid side chain.

A carboxyl group of $L^1$ that connects to $L^2$ may be the C-terminus of an amino acid or may be derived from a carboxyl group of an amino acid side chain, for example a glutamic acid amino acid side chain.

A hydroxy group of $L^1$ that connects to $L^2$ may be derived from a hydroxy group of an amino acid side chain, for example a serine amino acid side chain.

In one embodiment, —C(=O)O— and $L^2$ together form the group:

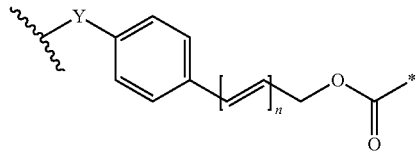

where the asterisk indicates the point of attachment to the Drug unit, the wavy line indicates the point of attachment to the $L^1$, Y is —N(H)—, —O—, —C(=O)N(H)— or —C(=O)O—, and n is 0 to 3. The phenylene ring is optionally substituted with one, two or three substituents as described herein.

In one embodiment, Y is NH.

In one embodiment, n is 0 or 1. Preferably, n is 0.

Where Y is NH and n is 0, the self-immolative group may be referred to as a p-aminobenzylcarbonyl linker (PABC).

The self-immolative group will allow for release of the Drug unit (i.e., the asymmetric PBD) when a remote site in the linker is activated, proceeding along the lines shown below (for n=0):

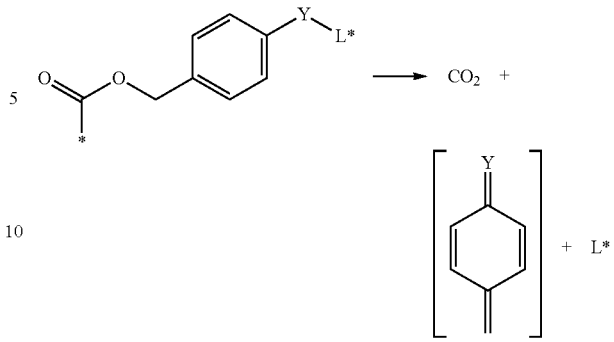

where the asterisk indicates the attachment to the Drug, L* is the activated form of the remaining portion of the linker and the released Drug unit is not shown. These groups have the advantage of separating the site of activation from the Drug.

In another embodiment, —C(=O)O— and $L^2$ together form a group selected from:

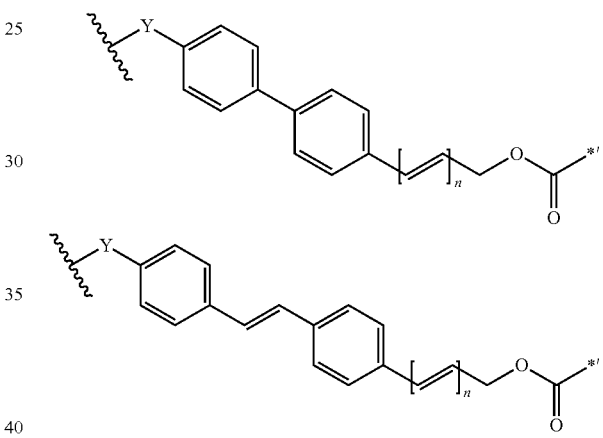

where the asterisk, the wavy line, Y, and n are as defined above. Each phenylene ring is optionally substituted with one, two or three substituents as described herein. In one embodiment, the phenylene ring having the Y substituent is optionally substituted and the phenylene ring not having the Y substituent is unsubstituted.

In another embodiment, —C(=O)O— and $L^2$ together form a group selected from:

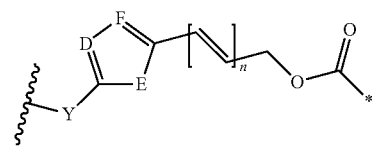

where the asterisk, the wavy line, Y, and n are as defined above, E is O, S or NR, D is N, CH, or CR, and F is N, CH, or CR.

In one embodiment, D is N.
In one embodiment, D is CH.
In one embodiment, E is O or S.
In one embodiment, F is CH.
In a preferred embodiment, the covalent bond between $L^1$ and $L^2$ is a cathepsin labile (e.g., cleavable) bond.

In one embodiment, $L^1$ comprises a dipeptide. The amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, the group —$X_1$—$X_2$— in dipeptide, —NH—$X_1$—$X_2$—CO—, is selected from:
-Phe-Lys-,
-Val-Ala-,
-Val-Lys-,
-Ala-Lys-,
-Val-Cit-,
-Phe-Cit-,
-Leu-Cit-,
-Ile-Cit-,
-Phe-Arg-, and
-Trp-Cit-;
where Cit is citrulline. In such a dipeptide, —NH— is the amino group of $X_1$, and CO is the carbonyl group of $X_2$.

Preferably, the group —$X_1$—$X_2$— in dipeptide, —NH—$X_1$—$X_2$—CO—, is selected from:
-Phe-Lys-,
-Val-Ala-,
-Val-Lys-,
-Ala-Lys-, and
-Val-Cit-.

Most preferably, the group —$X_1$—$X_2$— in dipeptide, —NH—$X_1$—$X_2$—CO—, is -Phe-Lys-, Val-Cit or -Val-Ala-.

Other dipeptide combinations of interest include:
-Gly-Gly-,
-Pro-Pro-, and
-Val-Glu-.

Other dipeptide combinations may be used, including those described by Dubowchik et al., which is incorporated herein by reference in its entirety and for all purposes.

In one embodiment, the amino acid side chain is chemically protected, where appropriate. The side chain protecting group may be a group as discussed below. Protected amino acid sequences are cleavable by enzymes. For example, a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective groups in Organic Synthesis, Greene and Wuts.

Possible side chain protecting groups are shown below for those amino acids having reactive side chain functionality:
Arg: Z, Mtr, Tos;
Asn: Trt, Xan;
Asp: Bzl, t-Bu;
Cys: Acm, Bzl, Bzl-OMe, Bzl-Me, Trt;
Glu: Bzl, t-Bu;
Gln: Trt, Xan;
His: Boc, Dnp, Tos, Trt;
Lys: Boc, Z—Cl, Fmoc, Z;
Ser: Bzl, TBDMS, TBDPS;
Thr: Bz;
Trp: Boc;
Tyr: Bzl, Z, Z—Br.

In one embodiment, —$X_2$— is connected indirectly to the Drug unit. In such an embodiment, the Spacer unit $L^2$ is present.

In one embodiment, —$X_2$— is connected directly to the Drug unit. In such an embodiment, the Spacer unit $L^2$ is absent.

In one embodiment, the dipeptide is used in combination with a self-immolative group(s) (the Spacer unit). The self-immolative group(s) may be connected to —$X_2$—.

Where a self-immolative group is present, —$X_2$— is connected directly to the self-immolative group. In one embodiment, —$X_2$— is connected to the group Y of the self-immolative group. Preferably the group —$X_2$—CO— is connected to Y, where Y is NH.

In one embodiment, —$X_1$— is connected directly to $A^1$. Preferably the group NH—$X_1$— (the amino terminus of $X_1$) is connected to $A^1$. $A^1$ may comprise the functionality —CO— thereby to form an amide link with —$X_1$—.

In one embodiment, $L^1$ and $L^2$ together with —OC(=O)— comprise the group —$X_1$—$X_2$-PABC-. The PABC group is connected directly to the Drug unit. In one example, the self-immolative group and the dipeptide together form the group -Phe-Lys-PABC-, which is illustrated below:

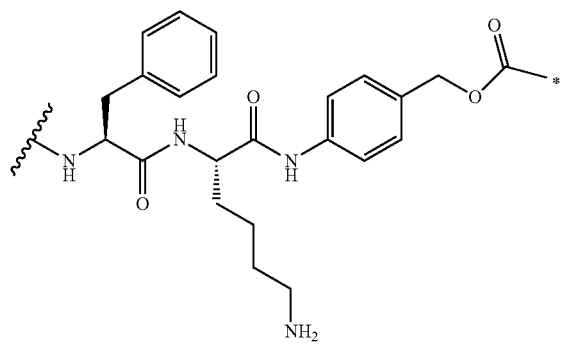

where the asterisk indicates the point of attachment to the Drug unit, and the wavy line indicates the point of attachment to the remaining portion of $L^1$ or the point of attachment to $A^1$. Preferably, the wavy line indicates the point of attachment to $A^1$.

Alternatively, the self-immolative group and the dipeptide together form the group -Val-Ala-PABC-, which is illustrated below:

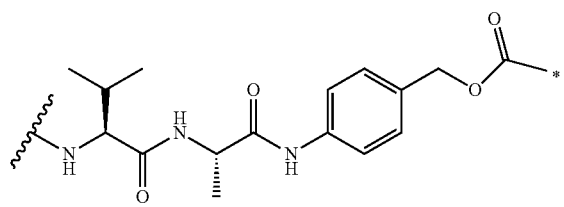 [SMILES: *N[C@H](C(=O)N[C@@H](C)C(=O)Nc1ccc(COC(C)=O)cc1)C(C)C]

where the asterisk and the wavy line are as defined above.

In another embodiment, $L^1$ and $L^2$ together with —OC(=O)— represent:

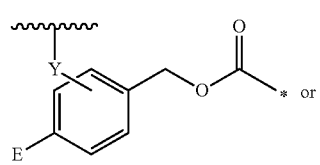

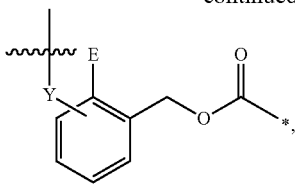

where the asterisk indicates the point of attachment to the Drug unit, the wavy line indicates the point of attachment to $A^1$, Y is a covalent bond or a functional group, and E is a group that is susceptible to cleavage thereby to activate a self-immolative group.

E is selected such that the group is susceptible to cleavage, e.g., by light or by the action of an enzyme. E may be —NO$_2$ or glucuronic acid (e.g., β-glucuronic acid). The former may be susceptible to the action of a nitroreductase, the latter to the action of a β-glucuronidase.

The group Y may be a covalent bond.

The group Y may be a functional group selected from:
—C(=O)—
—NH—
—O—
—C(=O)NH—,
—C(=O)O—,
—NHC(=O)—,
—OC(=O)—,
—OC(=O)O—,
—NHC(=O)O—,
—OC(=O)NH—,
—NHC(=O)NH—,
—NHC(=O)NH,
—C(=O)NHC(=O)—,
SO$_2$, and
—S—.

The group Y is preferably —NH—, —CH$_2$—, —O—, and —S—.

In some embodiments, $L^1$ and $L^2$ together with —OC(=O)— represent:

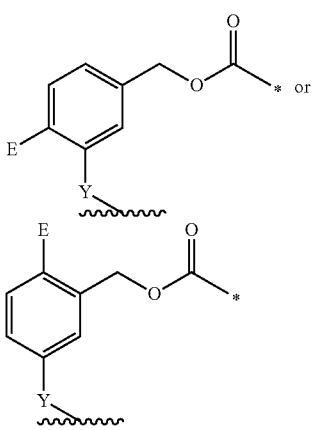

where the asterisk indicates the point of attachment to the Drug unit, the wavy line indicates the point of attachment to A, Y is a covalent bond or a functional group and E is glucuronic acid (e.g., β-glucuronic acid). Y is preferably a functional group selected from —NH—.

In some embodiments, $L^1$ and $L^2$ together represent:

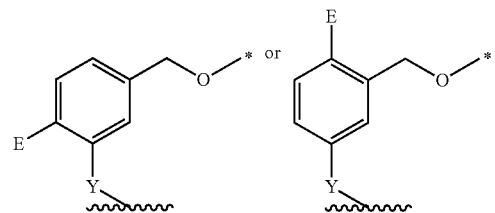

where the asterisk indicates the point of attachment to the remainder of $L^2$ or the Drug unit, the wavy line indicates the point of attachment to $A^1$, Y is a covalent bond or a functional group and E is glucuronic acid (e.g., β-glucuronic acid). Y is preferably a functional group selected from —NH—, —CH$_2$—, —O—, and —S—.

In some further embodiments, Y is a functional group as set forth above, the functional group is linked to an amino acid, and the amino acid is linked to the Stretcher unit $A^1$. In some embodiments, amino acid is β-alanine. In such an embodiment, the amino acid is equivalently considered part of the Stretcher unit.

The Specificity unit $L^1$ and the Ligand unit are indirectly connected via the Stretcher unit.

$L^1$ and $A^1$ may be connected by a bond selected from:
—C(=O)NH—,
—C(=O)O—,
—NHC(=O)—,
—OC(=O)—,
—OC(=O)O—,
—NHC(=O)O—,
—OC(=O)NH—, and
—NHC(=O)NH—.

In one embodiment, the group $A^1$ is:

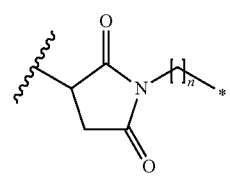

where the asterisk indicates the point of attachment to $L^1$, $L^2$ or D, the wavy line indicates the point of attachment to the Ligand unit, and n is 0 to 6. In one embodiment, n is 5.

In one embodiment, the group $A^1$ is:

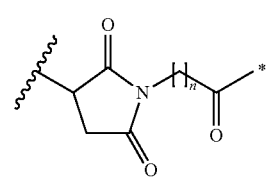

where the asterisk indicates the point of attachment to $L^1$, $L^2$ or D, the wavy line indicates the point of attachment to the Ligand unit, and n is 0 to 6. In one embodiment, n is 5.

In one embodiment, the group $A^1$ is:

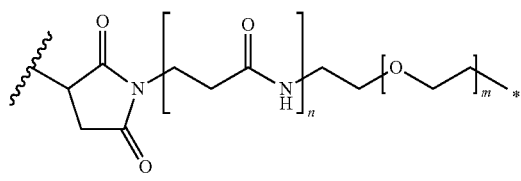

where the asterisk indicates the point of attachment to $L^1$, $L^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the group $A^1$ is:

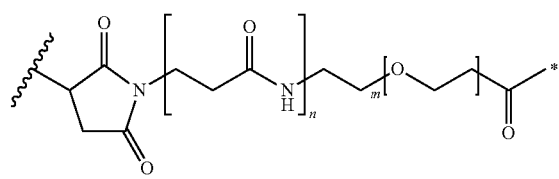

where the asterisk indicates the point of attachment to $L^1$, $L^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the group $A^1$ is:

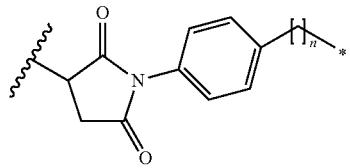

where the asterisk indicates the point of attachment to $L^1$, $L^2$ or D, the wavy line indicates the point of attachment to the Ligand unit, and n is 0 to 6. In one embodiment, n is 5.

In one embodiment, the group $A^1$ is:

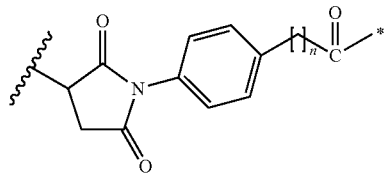

where the asterisk indicates the point of attachment to $L^1$, $L^2$ or D, the wavy line indicates the point of attachment to the Ligand unit, and n is 0 to 6. In one embodiment, n is 5.

In one embodiment, the group $A^1$ is:

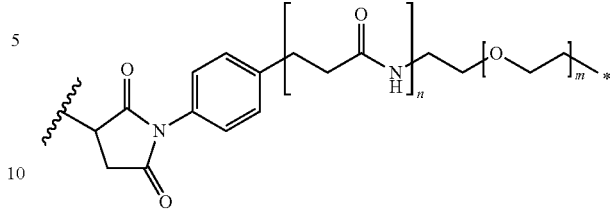

where the asterisk indicates the point of attachment to $L^1$, $L^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the group $A^1$ is:

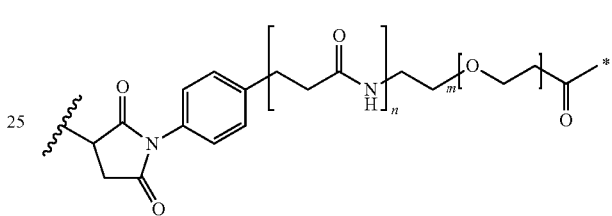

where the asterisk indicates the point of attachment to $L^1$, $L^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the connection between the Ligand unit and $A^1$ is through a thiol residue of the Ligand unit and a maleimide group of $A^1$.

In one embodiment, the connection between the Ligand unit and $A^1$ is:

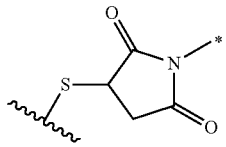 [SMILES: *SC1CC(=O)N(C)C1=O]

where the asterisk indicates the point of attachment to the remaining portion of $A^1$, $L^1$, $L^2$ or D, and the wavy line indicates the point of attachment to the remaining portion of the Ligand unit. In this embodiment, the S atom is typically derived from the Ligand unit.

In each of the embodiments above, an alternative functionality may be used in place of the malemide-derived group shown below:

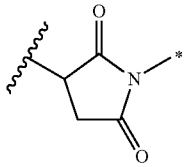

where the wavy line indicates the point of attachment to the Ligand unit as before, and the asterisk indicates the bond to the remaining portion of the $A^1$ group, or to $L^1$, $L^2$ or D.

In one embodiment, the maleimide-derived group is replaced with the group:

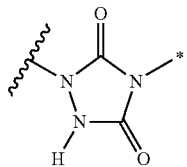 [SMILES: *n1[nH]c(=O)n(C)c1=O]

where the wavy line indicates point of attachment to the Ligand unit, and the asterisk indicates the bond to the remaining portion of the $A^1$ group, or to $L^1$, $L^2$ or D.

In one embodiment, the maleimide-derived group is replaced with a group, which optionally together with a Ligand unit (e.g., a Cell Binding Agent), is selected from:
—C(=O)NH—,
—C(=O)O—,
—NHC(=O)—,
—OC(=O)—,
—OC(=O)O—,
—NHC(=O)O—,
—OC(=O)NH—,
—NHC(=O)NH—,
—NHC(=O)NH,
—C(=O)NHC(=O)—,
—S—,
—S—S—,
—CH₂C(=O)—
—C(=O)CH₂—,
=N—NH—, and
—NH—N=.

Of these —C(=O)CH₂— may be preferred especially when the carbonyl group is bound to —NH—.

In one embodiment, the maleimide-derived group is replaced with a group, which optionally together with the Ligand unit, is selected from:

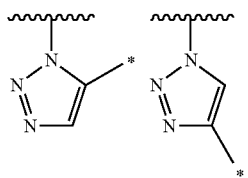

where the wavy line indicates either the point of attachment to the Ligand unit or the bond to the remaining portion of the $A^1$ group, and the asterisk indicates the other of the point of attachment to the Ligand unit or the bond to the remaining portion of the $A^1$ group.

Other groups suitable for connecting $L^1$ to the Cell Binding Agent are described in WO 2005/082023.

In one embodiment, the Stretcher unit $A^1$ is present, the Specificity unit $L^1$ is present and Spacer unit $L^2$ is absent. Thus, $L^1$ and the Drug unit are directly connected via a bond. Equivalently in this embodiment, $L^2$ is a bond.

$L^1$ and D may be connected by a bond selected from:
—C(=O)N<,
—OC(=O)N<, and
—NHC(=O)N<,
where N< is part of D.

In one embodiment, $L^1$ and D are preferably connected by a bond:
—C(=O)N<.

In one embodiment, $L^1$ comprises a dipeptide and one end of the dipeptide is linked to D. As described above, the amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, the group —$X_1$—$X_2$— in dipeptide, —NH—$X_1$—$X_2$—CO—, is selected from:
-Phe-Lys-,
-Val-Ala-,
-Val-Lys-,
-Ala-Lys-,
-Val-Cit-,
-Phe-Cit-,
-Leu-Cit-,
-Ile-Cit-,
-Phe-Arg-, and
-Trp-Cit-;
where Cit is citrulline. In such a dipeptide, —NH— is the amino group of $X_1$, and CO is the carbonyl group of $X_2$.

Preferably, the group —$X_1$—$X_2$— in dipeptide, —NH—$X_1$—$X_2$—CO—, is selected from:
-Phe-Lys-,
-Val-Ala-,
-Val-Lys-,
-Ala-Lys-, and
-Val-Cit-.

Most preferably, the group —$X_1$—$X_2$— in dipeptide, —NH—$X_1$—$X_2$—CO—, is -Phe-Lys- or -Val-Ala-.

Other dipeptide combinations of interest include:
-Gly-Gly-,
-Pro-Pro-, and
-Val-Glu-.

Other dipeptide combinations may be used, including those described above.

In one embodiment, $L^1$-D is:

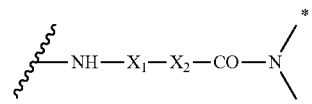

where —NH—$X_1$—$X_2$—CO is the dipeptide, —N< is part of the Drug unit, the asterisk indicates the points of attachment to the remainder of the Drug unit, and the wavy line indicates the point of attachment to the remaining portion of $L^1$ or the point of attachment to $A^1$. Preferably, the wavy line indicates the point of attachment to $A^1$.

In one embodiment, the dipeptide is valine-alanine and $L^1$-D is:

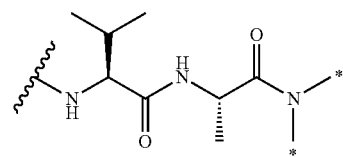 [SMILES: *N[C@H](C(=O)N[C@@H](C)C(=O)N(C)C)C(C)C]

where the asterisks, —N< and the wavy line are as defined above.

In one embodiment, the dipeptide is phenylalnine-lysine and $L^1$-D is:

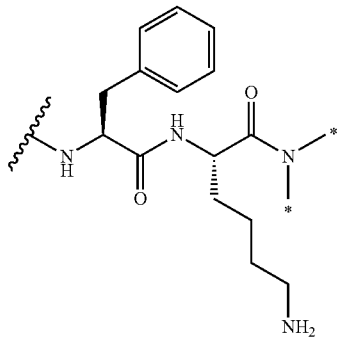 [SMILES: *N[C@@H](Cc1ccccc1)C(=O)N[C@@H](CCCCN)C(=O)N(C)C]

where the asterisks, —N< and the wavy line are as defined above.

In one embodiment, the dipeptide is valine-citrulline.

In one embodiment, the groups $A^1$-$L^1$ are:

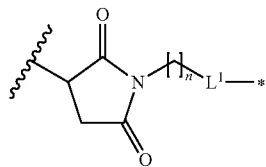

where the asterisk indicates the point of attachment to $L^2$ or D, the wavy line indicates the point of attachment to the Ligand unit, and n is 0 to 6. In one embodiment, n is 5.

In one embodiment, the groups $A^1$-$L^1$ are:

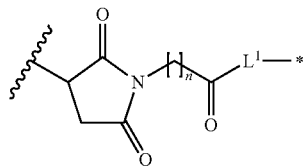

where the asterisk indicates the point of attachment to $L^2$ or D, the wavy line indicates the point of attachment to the Ligand unit, and n is 0 to 6. In one embodiment, n is 5.

In one embodiment, the groups $A^1$-$L^1$ are:

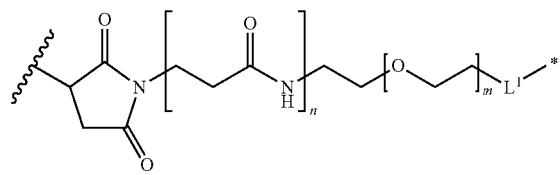

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups $A^1$-$L^1$ are:

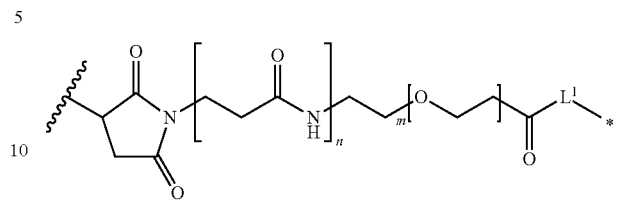

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 7, preferably 3 to 7, most preferably 3 or 7.

In one embodiment, the groups $A^1$-$L^1$ are:

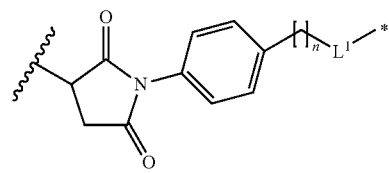

where the asterisk indicates the point of attachment to $L^2$ or D, the wavy line indicates the point of attachment to the Ligand unit, and n is 0 to 6. In one embodiment, n is 5.

In one embodiment, the groups $A^1$-$L^1$ are:

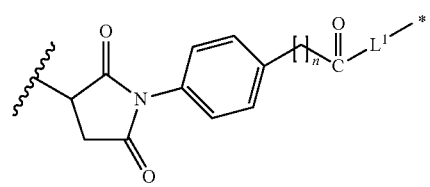

where the asterisk indicates the point of attachment to $L^2$ or D, the wavy line indicates the point of attachment to the Ligand unit, and n is 0 to 6. In one embodiment, n is 5.

In one embodiment, the groups $A^1$-$L^1$ are:

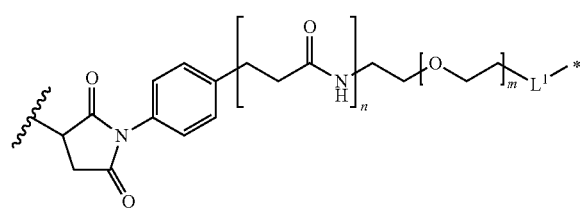

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups $A^1$-$L^1$ are:

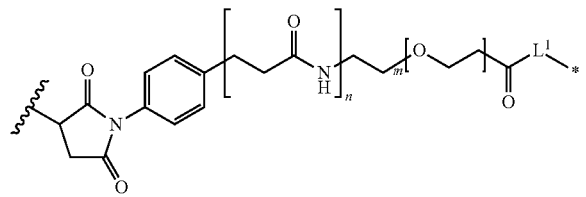

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups L-$A^1$-$L^1$ are:

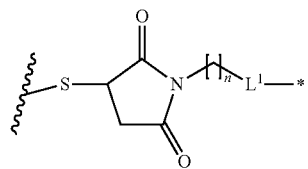

where the asterisk indicates the point of attachment to $L^2$ or D, S is a sulfur group of the Ligand unit, the wavy line indicates the point of attachment to the rest of the Ligand unit, and n is 0 to 6. In one embodiment, n is 5.

In one embodiment, the group L-$A^1$-$L^1$ are:

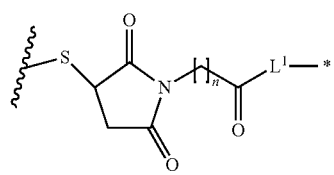

where the asterisk indicates the point of attachment to $L^2$ or D, S is a sulfur group of the Ligand unit, the wavy line indicates the point of attachment to the remainder of the Ligand unit, and n is 0 to 6. In one embodiment, n is 5.

In one embodiment, the groups L-$A^1$-$L^1$ are:

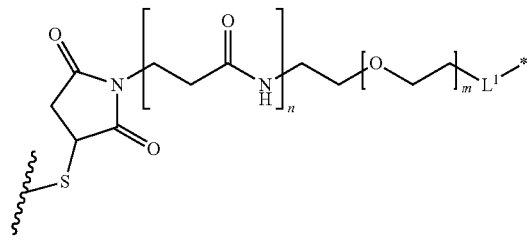

where the asterisk indicates the point of attachment to $L^2$ or D, S is a sulfur group of the Ligand unit, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups L-$A^1$-$L^1$ are:

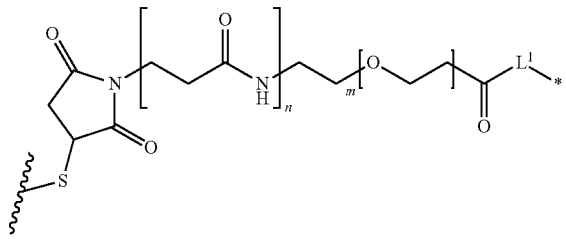

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 7, preferably 4 to 8, most preferably 4 or 8.

In one embodiment, the groups L-$A^1$-$L^1$ are:

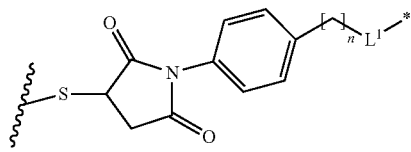

where the asterisk indicates the point of attachment to $L^2$ or D, the wavy line indicates the point of attachment to the remainder of the Ligand unit, and n is 0 to 6. In one embodiment, n is 5.

In one embodiment, the groups L-$A^1$-$L^1$ are:

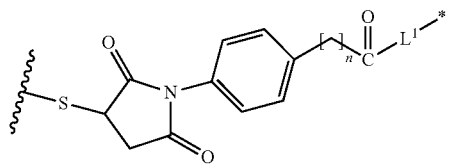

where the asterisk indicates the point of attachment to $L^2$ or D, the wavy line indicates the point of attachment to the remainder of the Ligand unit, and n is 0 to 6. In one embodiment, n is 5.

In one embodiment, the groups L-$A^1$-$L^1$ are:

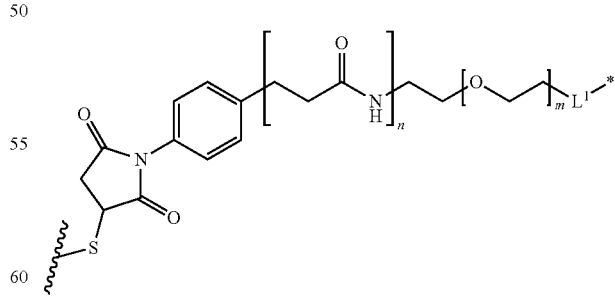

where the asterisk indicates the point of attachment to $L^2$ or D, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups L-A$^1$-L$^1$ are:

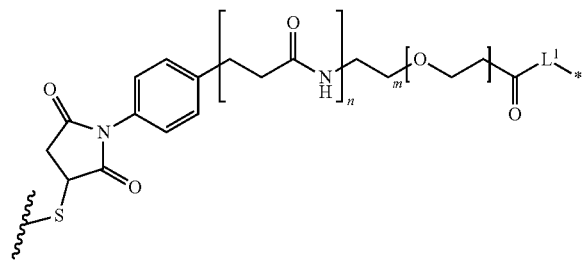

where the asterisk indicates the point of attachment to L$^2$ or D, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

In one embodiment, the Stretcher unit is an acetamide unit, having the formula:

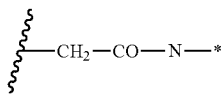

where the asterisk indicates the point of attachment to the remainder of the Stretcher unit, L$^1$ or D, and the wavy line indicates the point of attachment to the Ligand unit.

Linker-Drugs

In other embodiments, Linker-Drug compounds are provided for conjugation to a Ligand unit. In one embodiment, the Linker-Drug compounds are designed for connection to a Cell Binding Agent.

In one embodiment, the Drug Linker compound has the formula:

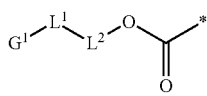

where the asterisk indicates the point of attachment to the Drug unit (D, as defined above), G$^1$ is a Stretcher group (A$^1$) to form a connection to a Ligand unit, L$^1$ is a Specificity unit, L$^2$ (a Spacer unit) is a covalent bond or together with —OC(=O)— forms a self-immolative group(s).

In another embodiment, the Drug Linker compound has the formula:

G$^1$-L$^1$-L$^2$-* where the asterisk indicates the point of attachment to the Drug unit (D), G$^1$ is a Stretcher unit (A$^1$) to form a connection to a Ligand unit, L$^1$ is a Specificity unit, L$^2$ (a Spacer unit) is a covalent bond or a self-immolative group(s).

L$^1$ and L$^2$ are as defined above. References to connection to A$^1$ can be construed here as referring to a connection to G$^1$.

In one embodiment, where L$^1$ comprises an amino acid, the side chain of that amino acid may be protected. Any suitable protecting group may be used. In one embodiment, the side chain protecting groups are removable with other protecting groups in the compound, where present. In other embodiments, the protecting groups may be orthogonal to other protecting groups in the molecule, where present.

Suitable protecting groups for amino acid side chains include those groups described in the Novabiochem Catalog 2006/2007. Protecting groups for use in a cathepsin labile linker are also discussed in Dubowchik et al.

In certain embodiments of the invention, the group L$^1$ includes a Lys amino acid residue. The side chain of this amino acid may be protected with a Boc or Alloc protected group. A Boc protecting group is most preferred.

The functional group G$^1$ forms a connecting group upon reaction with a Ligand unit (e.g., a cell binding agent.

In one embodiment, the functional group G$^1$ is or comprises an amino, carboxylic acid, hydroxy, thiol, or maleimide group for reaction with an appropriate group on the Ligand unit. In a preferred embodiment, G$^1$ comprises a maleimide group.

In one embodiment, the group G$^1$ is an alkyl maleimide group. This group is suitable for reaction with thiol groups, particularly cysteine thiol groups, present in the cell binding agent, for example present in an antibody.

In one embodiment, the group G$^1$ is:

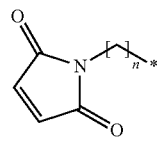

where the asterisk indicates the point of attachment to L$^1$, L$^2$ or D, and n is 0 to 6. In one embodiment, n is 5.

In one embodiment, the group G$^1$ is:

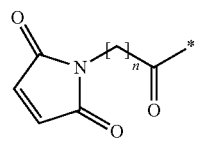

where the asterisk indicates the point of attachment to L$^1$, L$^2$ or D, and n is 0 to 6. In one embodiment, n is 5.

In one embodiment, the group G$^1$ is:

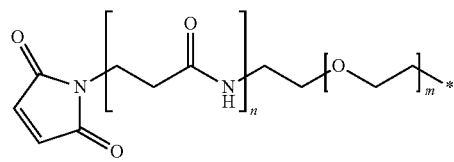

where the asterisk indicates the point of attachment to L$^1$, L$^2$ or D n is 0 or 1, and m is 0 to 30. In a preferred embodiment, n is 1 and m is 0 to 10, 1 to 2, preferably 4 to 8, and most preferably 4 or 8.

In one embodiment, the group $G^1$ is:

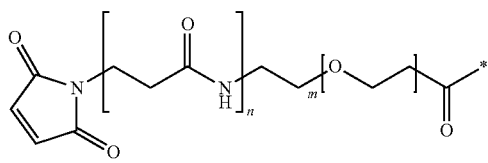

where the asterisk indicates the point of attachment to $L^1$, $L^1$, $L^2$ or D, n is 0 or 1, and m is 0 to 30. In a preferred embodiment, n is 1 and m is 0 to 10, 1 to 8, preferably 4 to 8, and most preferably 4 or 8.

In one embodiment, the group $G^1$ is:

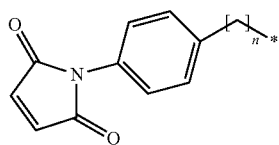

where the asterisk indicates the point of attachment to $L^1$, $L^2$ or D, and n is 0 to 6. In one embodiment, n is 5.

In one embodiment, the group $G^1$ is:

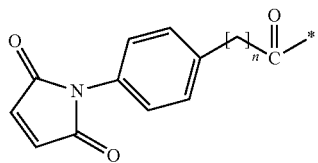

where the asterisk indicates the point of attachment to $L^1$, $L^2$ or D, and n is 0 to 6. In one embodiment, n is 5.

In one embodiment, the group $G^1$ is:

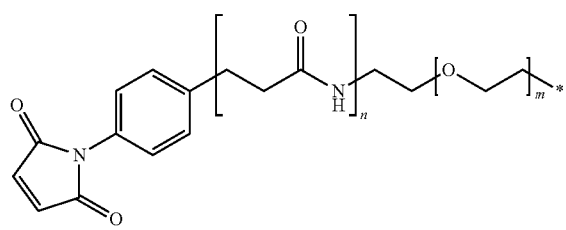

where the asterisk indicates the point of attachment to $L^1$, $L^2$ or D, n is 0 or 1, and m is 0 to 30. In a preferred embodiment, n is 1 and m is 0 to 10, 1 to 2, preferably 4 to 8, and most preferably 4 or 8.

In one embodiment, the group $G^1$ is:

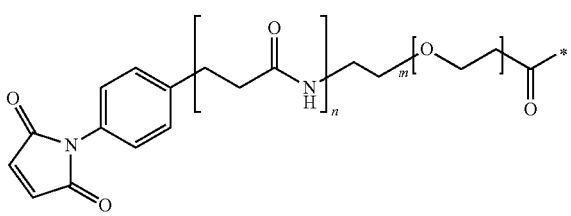

where the asterisk indicates the point of attachment to $L^1$, $L^2$ or D, n is 0 or 1, and m is 0 to 30. In a preferred embodiment, n is 1 and m is 0 to 10, 1 to 8, preferably 4 to 8, and most preferably 4 or 8.

In each of the embodiments above, an alternative functionality may be used in place of the malemide group shown below:

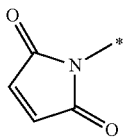

where the asterisk indicates the bond to the remaining portion of the G group.

In one embodiment, the maleimide-derived group is replaced with the group:

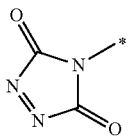

where the asterisk indicates the bond to the remaining portion of the G group.

In one embodiment, the maleimide group is replaced with a group selected from:
—C(=O)OH,
—OH,
—NH$_2$,
—SH,
—C(=O)CH$_2$X, where X is Cl, Br or I,
—CHO,
—NHNH$_2$
—C≡CH, and
—N$_3$ (azide).

Of these, —C(=O)CH$_2$X may be preferred, especially when the carbonyl group is bound to —NH—.

In one embodiment, $L^1$ is present, and $G^1$ is —NH$_2$, —NHMe, —COOH, —OH or —SH.

In one embodiment, where $L^1$ is present, $G^1$ is —NH$_2$ or —NHMe. Either group may be the N-terminal of an $L^1$ amino acid sequence.

In one embodiment, $L^1$ is present and $G^1$ is —NH$_2$, and $L^1$ is an amino acid sequence —X$_1$—X$_2$—, as defined above.

In one embodiment, $L^1$ is present and $G^1$ is COOH. This group may be the C-terminal of an $L^1$ amino acid sequence.

In one embodiment, $L^1$ is present and $G^1$ is OH.

In one embodiment, $L^1$ is present and $G^1$ is SH.

The group $G^1$ may be convertable from one functional group to another. In one embodiment, $L^1$ is present and $G^1$ is —NH$_2$. This group is convertable to another group $G^1$ comprising a maleimide group. For example, the group —NH$_2$ may be reacted with an acids or an activated acid (e.g., N-succinimide forms) of those $G^1$ groups comprising maleimide shown above.

The group $G^1$ may therefore be converted to a functional group that is more appropriate for reaction with a Ligand unit.

As noted above, in one embodiment, $L^1$ is present and $G^1$ is —NH$_2$, —NHMe, —COOH, —OH or —SH. In a further embodiment, these groups are provided in a chemically protected form. The chemically protected form is therefore a precursor to the linker that is provided with a functional group.

In one embodiment, G¹ is —NH₂ in a chemically protected form. The group may be protected with a carbamate protecting group. The carbamate protecting group may be selected from the group consisting of:

Alloc, Fmoc, Boc, Troc, Teoc, Cbz and PNZ.

Preferably, where G¹ is —NH₂, it is protected with an Alloc or Fmoc group.

In one embodiment, where G¹ is —NH₂, it is protected with an Fmoc group.

In one embodiment, the protecting group is the same as the carbamate protecting group of the capping group.

In one embodiment, the protecting group is not the same as the carbamate protecting group of the capping group. In this embodiment, it is preferred that the protecting group is removable under conditions that do not remove the carbamate protecting group of the capping group.

The chemical protecting group may be removed to provide a functional group to form a connection to a Ligand unit. Optionally, this functional group may then be converted to another functional group as described above.

In one embodiment, the active group is an amine. This amine is preferably the N-terminal amine of a peptide, and may be the N-terminal amine of the preferred dipeptides of the invention.

The active group may be reacted to yield the functional group that is intended to form a connection to a Ligand unit.

In other embodiments, the Linker unit is a precursor to the Linker unit having an active group. In this embodiment, the Linker unit comprises the active group, which is protected by way of a protecting group. The protecting group may be removed to provide the Linker unit having an active group.

Where the active group is an amine, the protecting group may be an amine protecting group, such as those described in Green and Wuts.

The protecting group is preferably orthogonal to other protecting groups, where present, in the Linker unit.

In one embodiment, the protecting group is orthogonal to the capping group. Thus, the active group protecting group is removable whilst retaining the capping group. In other embodiments, the protecting group and the capping group is removable under the same conditions as those used to remove the capping group.

In one embodiment, the Linker unit is:

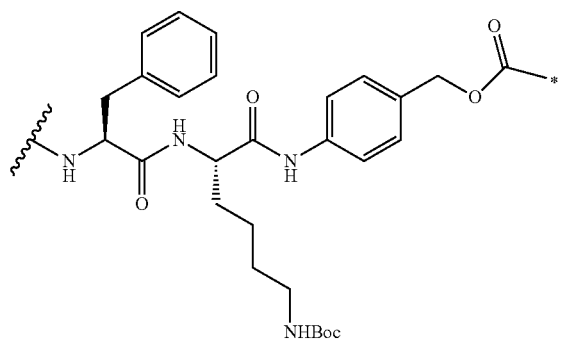 [SMILES: *N[C@@H](Cc1ccccc1)C(=O)N[C@@H](CCCCNC(=O)OC(C)(C)C)C(=O)Nc1ccc(COC(C)=O)cc1]

NHBoc where the asterisk indicates the point of attachment to the Drug unit, and the wavy line indicates the point of attachment to the remaining portion of the Linker unit, as applicable or the point of attachment to G¹. Preferably, the wavy line indicates the point of attachment to G¹.

In one embodiment, the Linker unit is:

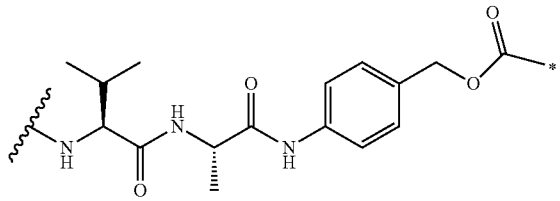 [SMILES: *N[C@H](C(=O)N[C@@H](C)C(=O)Nc1ccc(COC(C)=O)cc1)C(C)C]

where the asterisk and the wavy line are as defined above.

Other functional groups suitable for use in forming a connection between L¹ and the Cell Binding Agent are described in WO 2005/082023.

Ligand Unit

The Ligand Unit may be of any kind, and include a protein, polypeptide, peptide and a non-peptidic agent that specifically binds to a target molecule. In some embodiments, the Ligand unit may be a protein, polypeptide or peptide. In some embodiments, the Ligand unit may be a cyclic polypeptide. These Ligand units can include antibodies or a fragment of an antibody that contains at least one target molecule-binding site, lymphokines, hormones, growth factors, or any other cell binding molecule or substance that can specifically bind to a target. The ligand Unit is also referred to herein as a "binding agent" or "targeting agent".

The terms "specifically binds" and "specific binding" refer to the binding of an antibody or other protein, polypeptide or peptide to a predetermined molecule (e.g., an antigen). Typically, the antibody or other molecule binds with an affinity of at least about $1 \times 10^7$ M$^{-1}$, and binds to the predetermined molecule with an affinity that is at least two-fold greater than its affinity for binding to a non-specific molecule (e.g., BSA, casein) other than the predetermined molecule or a closely-related molecule.

Examples of Ligand units include those agents described for use in WO 2007/085930, which is incorporated herein in its entirety and for all purposes.

In some embodiments, the Ligand unit is a Cell Binding Agent that binds to an extracellular target on a cell. Such a Cell Binding Agent can be a protein, polypeptide, peptide or a non-peptidic agent. In some embodiments, the Cell Binding Agent may be a protein, polypeptide or peptide. In some embodiments, the Cell Binding Agent may be a cyclic polypeptide. The Cell Binding Agent also may be antibody or an antigen-binding fragment of an antibody. Thus, in one embodiment, the present invention provides an antibody-drug conjugate (ADC).

In one embodiment the antibody is a monoclonal antibody; chimeric antibody; humanized antibody; fully human antibody; or a single chain antibody. One embodiment the antibody is a fragment of one of these antibodies having biological activity. Examples of such fragments include Fab, Fab', F(ab')₂ and Fv fragments.

The antibody may be a diabody, a domain antibody (DAB) or a single chain antibody.

In one embodiment, the antibody is a monoclonal antibody.

Antibodies for use in the present invention include those antibodies described in WO 2005/082023 which is incorporated by reference herein in its entirety and for all purposes. Particularly preferred are those antibodies for tumour-associated antigens.

Examples of those antigens known in the art include, but are not limited to, those tumour-associated antigens set out in WO 2005/082023. See, for instance, pages 41-55.

In some embodiments, the conjugates are designed to target tumour cells via their cell surface antigens. The antigens may be cell surface antigens which are either over-expressed or expressed at abnormal times or cell types. Preferably, the target antigen is expressed only on proliferative cells (preferably tumour cells); however this is rarely observed in practice. As a result, target antigens are usually selected on the basis of differential expression between proliferative and healthy tissue.

Antibodies have been raised to target specific tumour related antigens including:

Cripto, CD19, CD20, CD22, CD30, CD33, Glycoprotein NMB, CanAg, Her2 (ErbB2/Neu), CD56 (NCAM), CD70, CD79, CD138, PSCA, PSMA (prostate specific membrane antigen), BCMA, E-selectin, EphB2, Melanotransferin, Muc16 and TMEFF2. In any of the embodiments provided herein, the Ligand unit can be a monoclonal antibody that specifically binds to the Cripto antigen, CD19 antigen, CD20 antigen, CD22 antigen, CD30 antigen, CD33 antigen, Glycoprotein NMB, CanAg antigen, Her2 (ErbB2/Neu) antigen, CD56 (NCAM) antigen, CD70 antigen, CD79 antigen, CD138 antigen, PSCA, PSMA (prostate specific membrane antigen), BCMA, E-selectin, EphB2, Melanotransferin, Muc16 antigen or TMEFF2 antigen.

The Ligand unit is connected to the Linker unit. In one embodiment, the Ligand unit is connected to A, where present, of the Linker unit.

In one embodiment, the connection between the Ligand unit and the Linker unit is through a thioether bond.

In one embodiment, the connection between the Ligand unit and the Linker unit is through a disulfide bond.

In one embodiment, the connection between the Ligand unit and the Linker unit is through an amide bond.

In one embodiment, the connection between the Ligand unit and the Linker unit is through an ester bond.

In one embodiment, the connection between the Ligand unit and the Linker is formed between a thiol group of a cysteine residue of the Ligand unit and a maleimide group of the Linker unit.

The cysteine residues of the Ligand unit may be available for reaction with the functional group of the Linker unit to form a connection. In other embodiments, for example where the Ligand unit is an antibody, the thiol groups of the antibody may participate in interchain disulfide bonds. These interchain bonds may be converted to free thiol groups by e.g. treatment of the antibody with DTT prior to reaction with the functional group of the Linker unit.

In some embodiments, the cysteine residue is introduced into the heavy or light chain of an antibody. Positions for cysteine insertion by substitution in antibody heavy or light chains include those described in Published U.S. Application No. 2007-0092940 and International Patent Publication WO2008/070593, which are herein incorporated by reference in their entirety and for all purposes.

Methods of Treatment

The compounds and conjugates of the present invention may be used in a method of therapy. Also provided is a method of treatment, comprising administering to a subject in need of treatment a therapeutically-effective amount of a compound or conjugate disclosed herein. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound or conjugate may be administered alone or in combination with other treatments, either simultaneously or sequentially dependent upon the condition to be treated. Examples of treatments and therapies include, but are not limited to, chemotherapy (the administration of active agents, including, e.g. drugs; surgery; and radiation therapy.

Pharmaceutical compositions according to the present invention, and for use in accordance with the present invention, may comprise, in addition to the active ingredient, i.e. a compound or conjugate disclosed herein, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The Compounds and Conjugates can be used to treat proliferative disease and autoimmune disease. The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreatic cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Other cancers of interest include, but are not limited to, haematological; malignancies such as leukemias and lymphomas, such as non-Hodgkin lymphoma, and subtypes such as DLBCL, marginal zone, mantle zone, and follicular, Hodgkin lymphoma, AML, and other cancers of B or T cell origin.

Examples of autoimmune disease include the following: rheumatoid arthritis, autoimmune demyelinative diseases (e.g., multiple sclerosis, allergic encephalomyelitis), psoriatic arthritis, endocrine ophthalmopathy, uveoretinitis, systemic lupus erythematosus, myasthenia gravis, Graves' disease, glomerulonephritis, autoimmune hepatological disorder, inflammatory bowel disease (e.g., Crohn's disease), anaphylaxis, allergic reaction, Sjögren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, antiphospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, and autoimmune gonadal failure.

In some embodiments, the autoimmune disease is a disorder of B lymphocytes (e.g., systemic lupus erythematosus, Goodpasture's syndrome, rheumatoid arthritis, and type I diabetes), Th1-lymphocytes (e.g., rheumatoid arthritis, multiple sclerosis, psoriasis, Sjögren's syndrome, Hashimoto's thyroiditis, Graves' disease, primary biliary cirrhosis, Wegener's granulomatosis, tuberculosis, or graft versus host disease), or Th2-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of Th1-lymphocytes or Th2-lymphocytes. In some embodiments, the autoimmune disorder is a T cell-mediated immunological disorder.

In some embodiments, the amount of the Conjugate administered ranges from about 0.01 to about 10 mg/kg per dose. In some embodiments, the amount of the Conjugate administered ranges from about 0.01 to about 5 mg/kg per dose. In some embodiments, the amount of the Conjugate administered ranges from about 0.05 to about 5 mg/kg per dose. In some embodiments, the amount of the Conjugate administered ranges from about 0.1 to about 5 mg/kg per dose. In some embodiments, the amount of the Conjugate administered ranges from about 0.1 to about 4 mg/kg per dose. In some embodiments, the amount of the Conjugate administered ranges from about 0.05 to about 3 mg/kg per dose. In some embodiments, the amount of the Conjugate administered ranges from about 0.1 to about 3 mg/kg per dose. In some embodiments, the amount of the Conjugate administered ranges from about 0.1 to about 2 mg/kg per dose.

Includes Other Forms

Unless otherwise specified, included in the above are the well known ionic, salt, solvate, and protected forms of these substituents. For example, a reference to carboxylic acid (—COOH) also includes the anionic (carbon/late) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Carbinolamines

The invention includes compounds where a solvent adds across the imine bond of the PBD moiety, which is illustrated below where the solvent is water or an alcohol ($R^AOH$, where $R^A$ is $C_{1-4}$ alkyl):

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

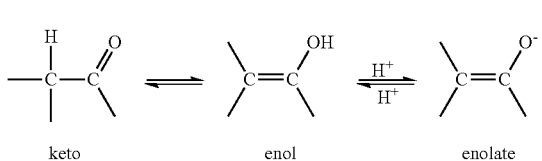

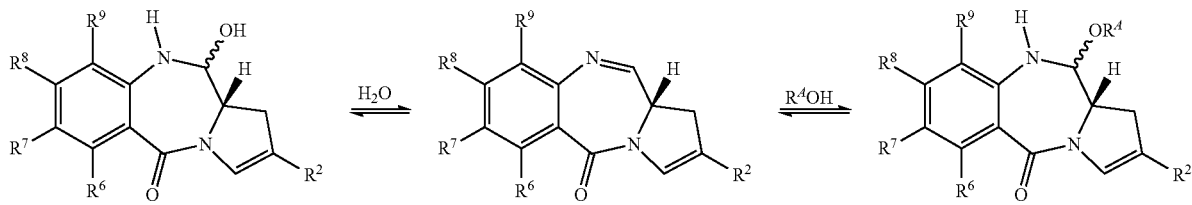

These forms can be called the carbinolamine and carbinolamine ether forms of the PBD. The balance of these equilibria depend on the conditions in which the compounds are found, as well as the nature of the moiety itself.

These particular compounds may be isolated in solid form, for example, by lyophilisation.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r- forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; 0 may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

General Synthetic Routes

The synthesis of PBD compounds is extensively discussed in the following references, which discussions are incorporated herein by reference in their entirety and for all purposes:

a) WO 00/12508 (pages 14 to 30);

b) WO 2005/023814 (pages 3 to 10);

c) WO 2004/043963 (pages 28 to 29); and d) WO 2005/085251 (pages 30 to 39).

Synthesis Route

The compounds of the present invention, where $R^{10}$ and $R^{11}$ form a nitrogen-carbon double bond between the nitrogen and carbon atoms to which they are bound, can be synthesised from a compound of Formula 2:

Formula 2
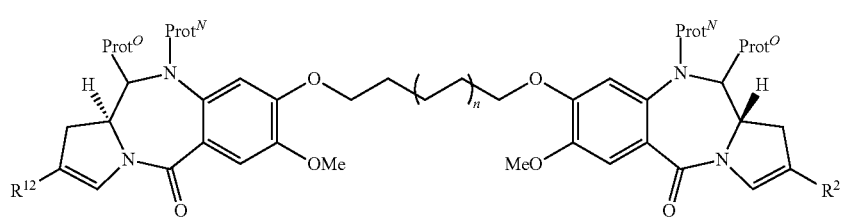
where n is 0 or 1, and $R^2$ and $R^{12}$ represent the C2 aromatic groups of the compounds of the present invention, as shown in the table below:
| | $R^2$ | $R^{12}$ | n |
|---|---|---|---|
| C1 | 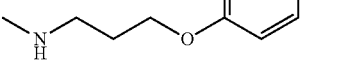 | 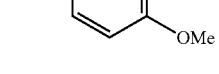 | 0 |
| C2 | 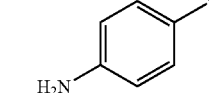 | 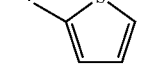 | 1 |
| C3 | 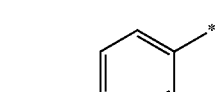 | 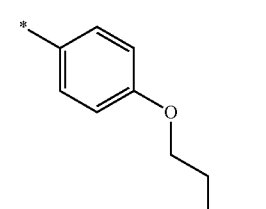 | 1 |
| C4 |  |  | 1 |
| C5 | 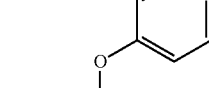 | 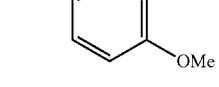 | 1 |
| C6 |  | 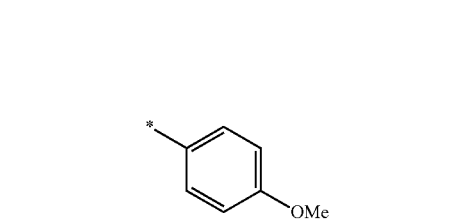 [SMILES: *c1ccc(OC)cc1] | 1 |

Prot$^N$ is a nitrogen protecting group for synthesis and Prot$^O$ is a protected oxygen group for synthesis or an oxo group, by deprotecting the imine bond by standard methods.

The compound produced may be in its carbinolamine or carbinolamine ether form depending on the solvents used. For example if Prot$^N$ is Troc and Prot$^O$ is an oxygen protecting group for synthesis, then the deprotection is carried out using a Cd/Pb couple to yield the compound of the present invention. If Prot$^N$ is SEM, or an analogous group, and Prot$^O$ is an oxo group, then the oxo group can be removed by reduction, which leads to a protected carbinolamine intermediate, which can then be treated to remove the SEM protecting group, followed by the elimination of water. The reduction of the compound of Formula 2 can be accomplished by, for example, superhydride or lithium tetraborohydride, whilst a suitable means for removing the SEM protecting group is treatment with silica gel.

Compounds of formula 2 can be synthesised from a compound of formula 3a:

Formula 3

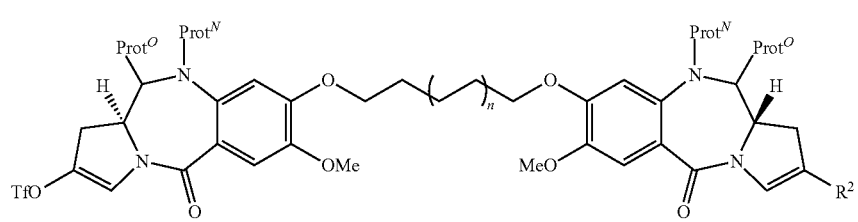

where R$^2$, Prot$^N$ and Prot$^O$ are as defined for compounds of formula 2, by coupling an organometallic derivative comprising R$^{12}$, such as an organoboron derivative. The organoboron derivative may be a boronate or boronic acid.

Compounds of formula 2 can be synthesised from a compound of formula 3b:

Formula 3b

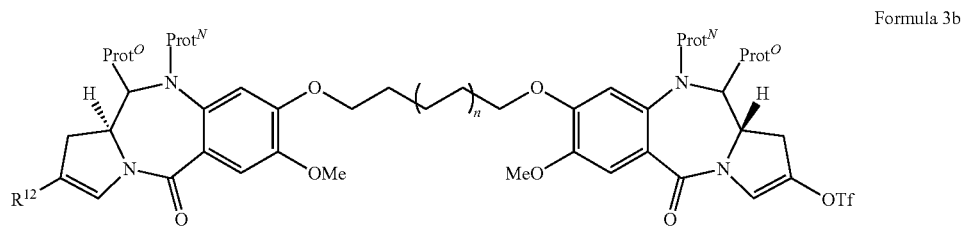

where R$^{12}$, Prot$^N$ and Prot$^O$ are as defined for compounds of formula 2, by coupling an organometallic derivative comprising R$^2$, such as an organoboron derivative. The organoboron derivative may be a boronate or boronic acid.

Compounds of formulae 3a and 3b can be synthesised from a compound of formula 4:

Formula 4

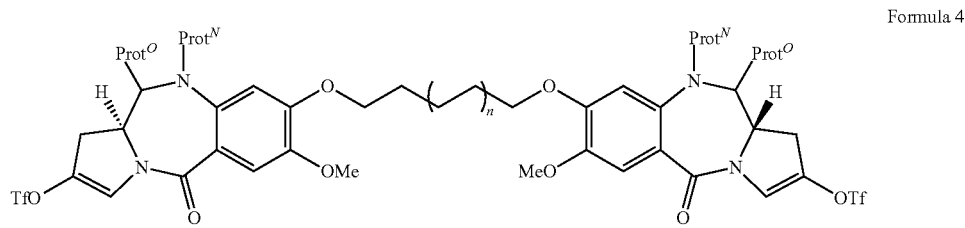

where Prot$^N$ and Prot$^O$ are as defined for compounds of formula 2, by coupling about a single equivalent (e.g. 0.9 or 1 to 1.1 or 1.2) of an organometallic derivative, such as an organoboron derivative, comprising R$^2$ or R$^{12}$.

The couplings described above are usually carried out in the presence of a palladium catalyst, for example Pd(PPh$_3$)$_4$, Pd(OCOCH$_3$)$_2$, PdCl$_2$, Pd$_2$(dba)$_3$. The coupling may be carried out under standard conditions, or may also be carried out under microwave conditions.

The two coupling steps are usually carried out sequentially. They may be carried out with or without purification between the two steps. If no purification is carried out, then the two steps may be carried out in the same reaction vessel. Purification is usually required after the second coupling step. Purification of the compound from the undesired by-products may be carried out by column chromatography or ion-exchange separation.

The synthesis of compounds of formula 4 where Prot$^{602}$ is an oxo group and Prot$^N$ is SEM are described in detail in WO 00/12508, which is incorporated herein by reference in its entirety and for all purposes. In particular, reference is made to scheme 7 on page 24, where the above compound is designated as intermediate P. This method of synthesis is also described in WO 2004/043963. Further reference is also made to the synthesis of compounds 8a and 8b in WO 2010/043880 (pages 36 to 45), which is incorporated herein by reference in its entirety and for all purposes.

The synthesis of compounds of formula 4 where Prot$^O$ is a protected oxygen group for synthesis are described in WO 2005/085251, which synthesis is herein incorporated by reference in its entirety and for all purposes.

Compounds of the present invention where R$^{10}$ and R$^{10'}$ are H and R$^{11}$ and R$^{11'}$ are SO$_z$M, can be synthesised from compounds of the present invention where R$^{10}$ and R$^{11}$ form a nitrogen-carbon double bond between the nitrogen and carbon atoms to which they are bound, by the addition of the appropriate bisulphite salt or sulphinate salt, followed by an appropriate purification step. Further methods are described in GB 2 053 894, which is herein incorporated by reference.

In some embodiments of the invention, it may be that the compounds of Formula 2 are used in the synthesis of the drug linker compounds. In these embodiments, the removal of the N10/C11 protecting groups may occur during the synthesis of the drug linker compounds.

Nitrogen Protecting Groups for Synthesis

Nitrogen protecting groups for synthesis are well known in the art. In the present invention, the protecting groups of particular interest are carbamate nitrogen protecting groups and hemi-aminal nitrogen protecting groups.

Carbamate nitrogen protecting groups have the following structure:

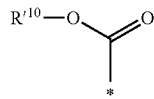

wherein R$'^{10}$ is R as defined above. A large number of suitable groups are described on pages 503 to 549 of Greene, T. W. and Wuts, G. M., Protective Groups in Organic Synthesis, 3$^{rd}$ Edition, John Wiley & Sons, Inc., 1999, which is incorporated herein by reference in its entirety and for all purposes.

Particularly preferred protecting groups include Troc, Teoc, Fmoc, BOC, Doc, Hoc, TcBOC, 1-Adoc and 2-Adoc.

Other possible groups are nitrobenzyloxycarbonyl (e.g. 4-nitrobenzyloxycarbonyl) and 2-(phenylsulphonyl)ethoxycarbonyl.

Those protecting groups which can be removed with palladium catalysis are not preferred, e.g. Alloc.

Hemi-aminal nitrogen protecting groups have the following structure:

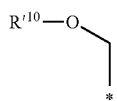

wherein R$'^{10}$ is R as defined above. A large number of suitable groups are described on pages 633 to 647 as amide protecting groups of Greene, T. W. and Wuts, G. M., Protective Groups in Organic Synthesis, 3$^{rd}$ Edition, John Wiley & Sons, Inc., 1999, which is incorporated herein by reference in its entirety and for all purposes. The groups disclosed herein can be applied to compounds of the present invention. Such groups include, but are not limited to, SEM, MOM, MTM, MEM, BOM, nitro or methoxy substituted BOM, Cl$_3$CCH$_2$OCH$_2$—.

Protected Oxygen Group for Synthesis

Protected oxygen group for synthesis are well known in the art. A large number of suitable oxygen protecting groups are described on pages 23 to 200 of Greene, T. W. and Wuts, G. M., Protective Groups in Organic Synthesis, 3$^{rd}$ Edition, John Wiley & Sons, Inc., 1999, which is incorporated herein by reference in its entirety and for all purposes.

Classes of particular interest include silyl ethers, methyl ethers, alkyl ethers, benzyl ethers, esters, acetates, benzoates, carbonates, and sulfonates.

Preferred oxygen protecting groups include acetates, TBS and THP.

Synthesis of Drug Conjugates

Conjugates comprising PBD dimers as described herein can be prepared using the knowledge of the skilled artisan in combination with the teachings provided herein. For example, linkers are described in U.S. Pat. No. 6,214,345, U.S. Pat. No. 7,498,298 as well as WO 2009/0117531, each of which is incorporated herein by reference in their entirety and for all purposes. Other linkers can be prepared according to the references cited herein or as known to the skilled artisan.

Linker-Drug compounds can be prepared according to methods known in the art in combination with the teachings provided herein. For example, linkage of amine-based X substituents (of the PBD dimer Drug unit) to active groups of the Linker units can be performed according to methods generally described in U.S. Pat. Nos. 6,214,345 and 7,498,298; and WO 2009-0117531, or as otherwise known to the skilled artisan.

Antibodies can be conjugated to Linker-Drug compounds as described in Doronina et al., Nature Biotechnology, 2003, 21, 778-784). Briefly, antibodies (4-5 mg/mL) in PBS containing 50 mM sodium borate at pH 7.4 are reduced with tris(carboxyethyl)phosphine hydrochloride (TCEP) at 37° C. The progress of the reaction, which reduces interchain disulfides, is monitored by reaction with 5,5'-dithiobis(2-nitrobenzoic acid) and allowed to proceed until the desired level of thiols/mAb is achieved. The reduced antibody is then cooled to 0° C. and alkylated with 1.5 equivalents of maleimide drug-linker per antibody thiol. After 1 hour, the reaction is quenched by the addition of 5 equivalents of N-acetyl cysteine. Quenched drug-linker is removed by gel filtration over a PD-10 column. The ADC is then sterile-filtered through a 0.22 μm syringe filter. Protein concentration can be determined by spectral analysis at 280 nm and 329 nm, respectively, with correction for the contribution of drug absorbance at 280 nm. Size exclusion chromatography can be used to determine the extent of antibody aggregation, and RP-HPLC can be used to determine the levels of remaining NAC-quenched drug-linker.

Antibodies with introduced cysteine residues can be conjugated to Linker-Drug compounds as described in International Patent Publication WO2008/070593, which is incorporated herein by reference in its entirety and for all purposes or as follows. Antibodies containing an introduced cysteine residue in the heavy chain are fully reduced by adding 10 equivalents of TCEP and 1 mM EDTA and adjusting the pH to 7.4 with 1M Tris buffer (pH 9.0). Following a 1 hour incubation at 37° C., the reaction is cooled to 22° C. and 30 equivalents of dehydroascorbic acid is added to selectively reoxidize the native disulfides, while leaving the introduced cysteine in the reduced state. The pH is adjusted to 6.5 with 1M Tris buffer (pH 3.7) and the reaction is allowed to proceed for 1 hour at 22° C. The pH of the solution is then raised again to 7.4 by addition of 1 M Tris buffer (pH 9.0). 3.5 equivalents of the PBD drug linker in DMSO is placed in a suitable container for dilution with propylene glycol prior to addition to the reaction. To maintain solubility of the PBD drug linker, the antibody itself is first diluted with propylene glycol to a final concentration of 33% (e.g., if the antibody solution was in a 60 mL reaction volume, 30 mL of propylene glycol was added). This same volume of propylene glycol (30 mL in this example) is added to the PBD drug linker as a diluent. After mixing, the solution of PBD drug linker in propylene glycol is added to the antibody solution to effect the conjugation; the final concentration of propylene glycol is 50%. The reaction is allowed to proceed for 30 minutes and then quenched by addition of 5 equivalents of N-acetyl cysteine. The ADC is purified by ultrafiltration through a 30 kD membrane. (Note that the concentration of propylene glycol used in the reaction can be reduced for any particular PBD, as its sole purpose is to maintain solubility of the drug linker in the aqueous media.)

For halo-acetamide-based Linker-Drug compounds, conjugation can be performed generally as follows. To a solution of reduced and reoxidized antibodies (having introduced cysteines in the heavy chain) in 10 mM Tris (pH 7.4), 50 mM NaCl, and 2 mM DTPA is added 0.5 volumes of propylene glycol. A 10 mM solution of acetamide-based Linker-Drug compound in dimethylacetamide is prepared immediately prior to conjugation. An equivalent amount of propylene glycol as added to the antibody solution is added to a 6-fold molar excess of the Linker-Drug compound. The dilute Linker-Drug solution is added to the antibody solution and the pH is adjusted to 8-8.5 using 1 M Tris (pH 9). The conjugation reaction is allowed to proceed for 45 minutes at 37° C. The conjugation is verified by reducing and denaturing reversed phase PLRP-S chromatography. Excess Linker-Drug compound is removed with Quadrasil MP resin and the buffer is exchanged into 10 mM Tris (pH 7.4), 50 mM NaCl, and 5% propylene glycol using a PD-10 desalting column.

Illustrative Synthesis Schemes for Drug Linkers

The following scheme is illustrative of routes for synthesising drug linkers.

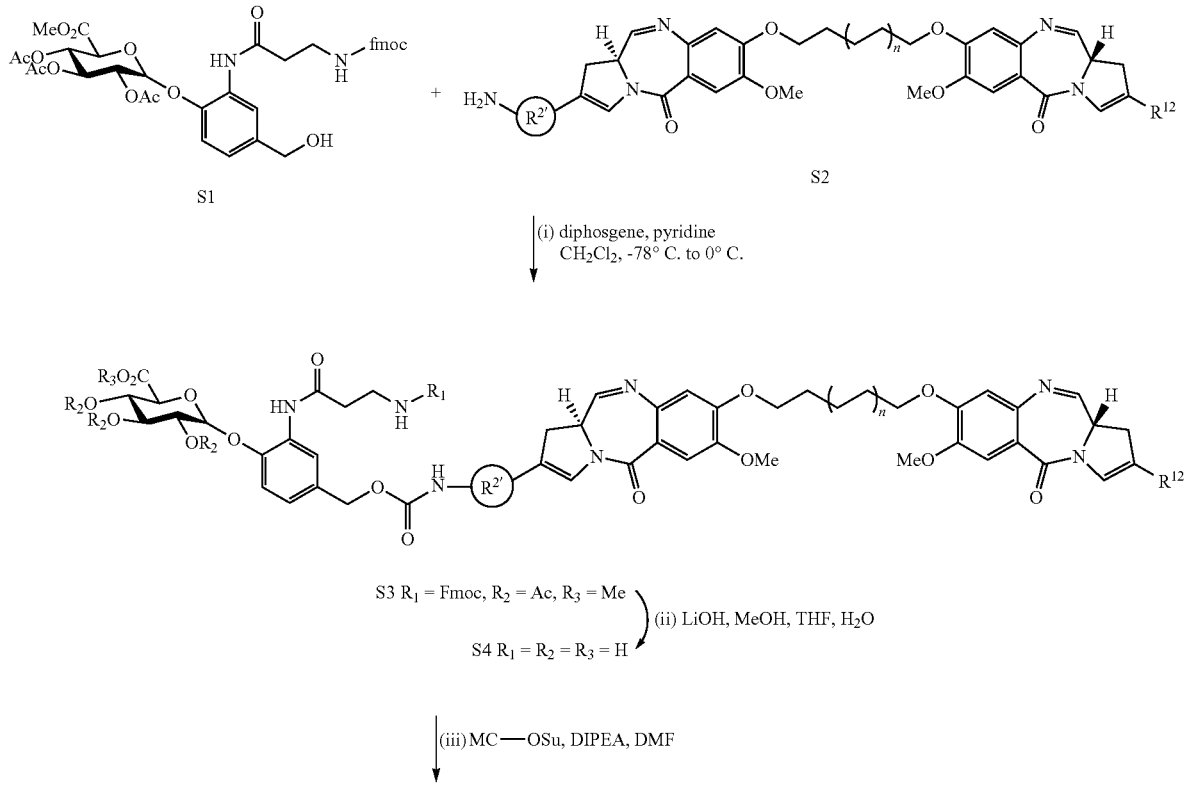

-continued

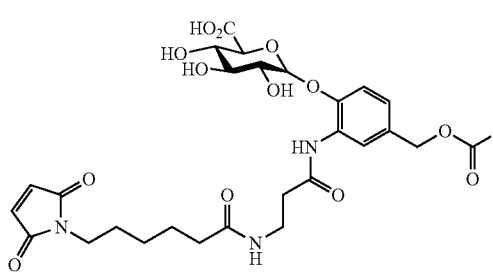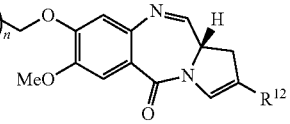

S5

R[2'] represents the part of R[2] (as defined above) which links the PBD core to the NH$_2$ group (for compound C1, the NH$_2$ group is replaced by NHMe). n is as defined above.

The glucuronide linker intermediate S1 (reference: Jeffrey et al., Bioconjugate Chemistry, 2006, 17, 831-840) can be treated with diphosgene in dichlroromethane at −78° C. to afford the glucuronide chloroformate, which is then reacted with the PBD dimer S2 dissolved in CH$_2$Cl$_2$ by dropwise addition. Warming the reaction to 0° C. over 2 hours followed by extraction will yield the compound S3. Treating a solution of S3 in an equal solvent mixture of MeOH, tetrahydrofuran, and water (cooled to 0° C.) with lithium hydroxide monohydrate for 4 hours, followed by reaction with glacial acetic acid will yield the compound S4. Adding maleimidocaproyl NHS ester to a solution of S4 in DMF, followed by diisopropylethylamine and stirring at room temperature under nitrogen for 2 hours will yield the desired drug linker S5.

The methods of Examples 2, 3, 4, 6, 7 and 8 could be adapted for all the PBD compounds of the present invention.

Further Preferences

The following preferences may apply to all aspects of the invention as described above, or may relate to a single aspect. The preferences may be combined together in any combination.

When R[10] is carbamate nitrogen protecting group, it may preferably be Teoc, Fmoc and Troc, and may more preferably be Troc.

When R[11] is O-Prot°, wherein Prot° is an oxygen protecting group, Prot° may preferably be TBS or THP, and may more preferably be TBS.

When R[10] is a hemi-aminal nitrogen protecting group, it may preferably be MOM, BOM or SEM, and may more preferably be SEM.

Conjugates (a) Conjugates of the present invention include, for example, those of the formula:

CBA-A[1]-L[1]-* where the asterisk indicates the point of attachment to the PBD dimer (D), or the Spacer Unit, CBA is the Cell Binding Agent, L[1] is a Specificity unit that is cleavable by the action of an enzyme, and A[1] is a Stretcher unit connecting L[1] to the Cell Binding Agent.

(b) Conjugates of the present invention include, for example, those of the formula:

CBA-A[1]-L[1]-* where the asterisk indicates the point of attachment to the PBD dimer (D), CBA is the Cell Binding Agent, A[1] is a Stretcher unit connecting L[1] to the Cell Binding Agent and L[1] is a Specificity unit that is cleavable by the action of cathepsin, L[1] is a dipeptide, L[1] is a dipeptide that is cleavable by the action of cathepsin or L[1] is a dipeptide selected from -Phe-Lys-, -Val-Ala-, -Val-Lys-, -Ala-Lys-, and -Val-Cit-.

Preferred conjugates of the present invention include any of those described in (a) and (b) wherein A[1] is

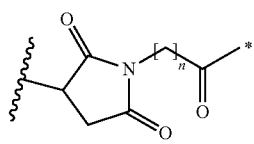

where the asterisk indicates the point of attachment to L[1], the wavy line indicates the point of attachment to CBA, and n is 0 to 6 (preferably n is 5).

Preferred conjugates of the present invention include those wherein the Linker Unit is

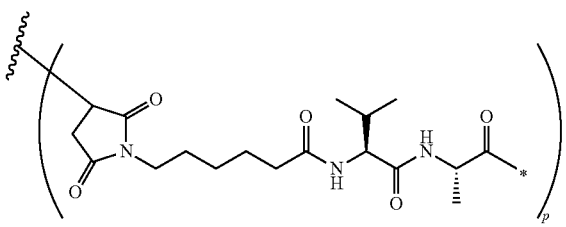

wherein the wavy line indicates the point of attachment to the Ligand unit (e.g., antibody) and the asterisk indicates the point of attachment to D.

In a particularly preferred embodiment, for all of the conjugates, the connection between the antibody and the Linker unit is formed between a thiol group of a cysteine residue of the antibody and a maleimide group of the Linker unit.

In a particularly preferred embodiment, for all of the preferred conjugates, the antibody is a monoclonal antibody that specifically binds to the Cripto antigen, CD19 antigen, CD20 antigen, CD22 antigen, CD30 antigen, CD33 antigen, Glycoprotein NMB, CanAg antigen, Her2 (ErbB2/Neu) antigen, CD56 (NCAM) antigen, CD70 antigen, CD79 antigen, CD138 antigen, PSCA, PSMA (prostate specific membrane antigen), BCMA, E-selectin, EphB2, Melanotransferin, Muc16 antigen or TMEFF2 antigen.

EXAMPLES

General Experimental Methods for Example 1

Optical rotations were measured on an ADP 220 polarimeter (Bellingham Stanley Ltd.) and concentrations (c) are given in g/100 mL. Melting points were measured using a digital melting point apparatus (Electrothermal). IR spectra were recorded on a Perkin-Elmer Spectrum 1000 FT IR Spectrometer. $^1H$ and $^{13}C$ NMR spectra were acquired at 300 K using a Bruker Avance NMR spectrometer at 400 and 100 MHz, respectively. Chemical shifts are reported relative to TMS ($\delta$=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, $F_{254}$), and flash chromatography utilised silica gel (Merck 60, 230-400 mesh ASTM). Except for the HOBt (NovaBiochem) and solid-supported reagents (Argonaut), all other chemicals and solvents were purchased from Sigma-Aldrich and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40-60° C.

General LC/MS conditions: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B within 3 min. The composition was held for 0.5 min at 95% B, and then returned to 5% B in 0.3 minutes. Total gradient run time equals 5 min. Flow rate 3.0 mi./min, 400 µL was split via a zero dead volume tee piece which passes into the mass spectrometer. Wavelength detection range: 220 to 400 nm. Function type: diode array (535 scans). Column: Phenomenex® Onyx Monolithic C18 50×4.60 mm

Example 1

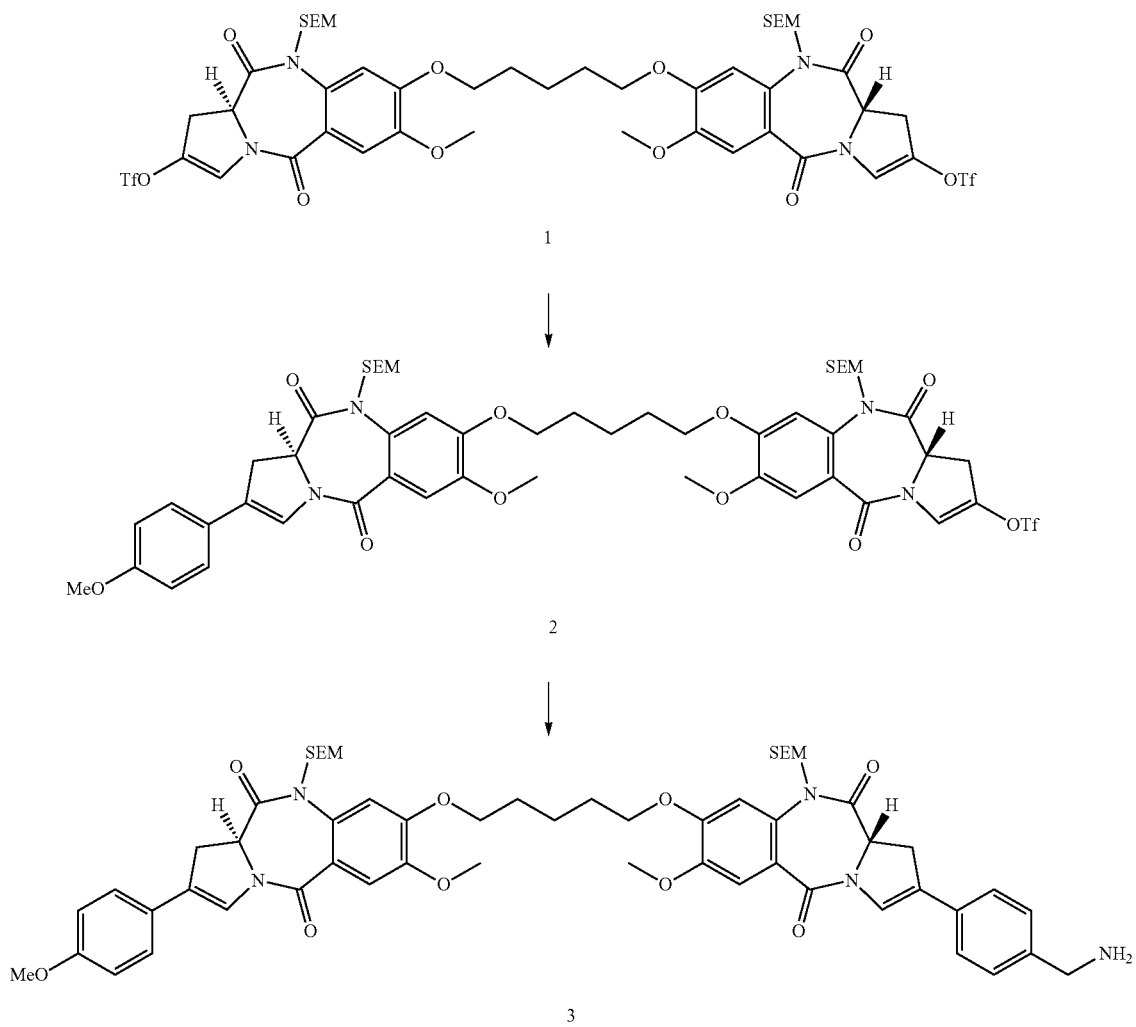

(a) (S)-2-(4-methoxyphenyl)-7-methoxy-8-(3-((S)-7-methoxy-2-(trifluoromethylsulfonyl)-5,11-dioxo-10-((2-(trimethylsilyl)ethoxy)methyl)-5,10,11,11a-tetrahydro-1H-pyrrolo[2,1-c][1,4]benzodiazepin-8-yloxy)pentoxyoxy)-10-((2-(trimethylsilyl)ethoxy)methyl)-1H-pyrrolo[2,1-c][1,4]benzodiazepine-5,11(10H,11aH)-dione (2)

Tetrakis-tris-phenylphosphine palladium complex (38 mg, $3.23 \times 10^{-5}$ mol, 0.02 eq) was added to a stirred, degassed mixture of 1,1'-[[(Pentane-1,5-diyl)dioxy]bis(11aS)-7-methoxy-2-[[(trifluoromethyl)sulfonyl]oxy]-10-((2-(trimethylsilyl)ethoxy)methyl)-1,10,11,11a-tetrahydro-5H-pyrrolo[2,1-c][1,4]-benzodiazepin-5,11-dione] (1) (Compound 8b in WO 2010/043880) (185 mg, 1.62 mmol, 1.0 eq.), 4-methoxyphenyl boronic acid (234 mg, 1.54 mmol, 0.95 eq.) and $Na_2CO_3$ (274 mg, 2.59 mmol, 1.6 eq.) in toluene/ethanol/water (10 mL/5 mL/5 mL). The reaction mixture was allowed to stir at room temperature under an argon atmosphere for 3 hours. The reaction mixture was diluted with ethylacetate and the aqueous portion was separated. The organic portion was washed with water, saturated brine, dried ($MgSO_4$) and evaporated under reduced pressure. Purification by flash column chromatography [gradient elution, ethylacetate 30%/n-hexane 70% to ethylacetate 80%/n-hexane 20%] afforded the product as a yellow foam (0.7 g, 39%). Analytical Data: RT 3.97 min; MS ($ES^+$) m/z (relative intensity) 1103 ([M+H]$^+$, 100), (b) (S)-2-(4-(aminomethyl)phenyl)-7-methoxy-8-((5-(((S)-7-methoxy-2-(4-methoxyphenyl)-5,11-dioxo-10-((2-(trimethylsilyl)ethoxy)methyl)-5,10,11,11a-tetrahydro-1H-benzo[e]pyrrolo[1,2-a][1,4]diazepin-8-yl)oxy)pentyl)oxy)-10-((2-(trimethylsilyl)ethoxy)methyl)-1H-benzo[e]pyrrolo[1,2-a][1,4]diazepine-5,11(10H,11aH)-dione (3)

Tetrakis-tris-phenylphosphine palladium complex (30 mg, $2.5 \times 10^{-5}$ mol, 0.04 eq) was added to a stirred, degassed mixture of the methoxy triflate (2) (700 mg, 0.63 mmol, 1.0 eq.), 4-aminomethylphenyl boronic acid (190 mg, 1.015 mmol, 1.6 eq.) and $Na_2CO_3$ (303 mg, 2.85 mmol, 4.5 eq.) in toluene/ethanol/water (20 mL/10 mL/10 mL). The reaction mixture was heated at 75° C. under an argon atmosphere for 3 hours. The reaction mixture was diluted with ethylacetate and the aqueous portion was separated. The organic portion was washed with water, saturated brine, dried ($MgSO_4$) and evaporated under reduced pressure gave the crude product as a brown foam. Purification by flash column chromatography [gradient elution, ethylacetate 50%/n-hexane 50% to ethylacetate 100%] afforded the product (0.55 g, 82%). Analytical Data: RT 3.48 min; MS ($ES^+$) m/z (relative intensity) 1060 ([M+H]$^+$, 100).

General Experimental Methods for Example 2

All commercially available anhydrous solvents were used without further purification. Analytical thin layer chromatography was performed on silica gel 60 F254 aluminum sheets (EMD Chemicals, Gibbstown, N.J.). Radial chromatography was performed on Chromatotron apparatus (Harris Research, Palo Alto, Calif.). Analytical HPLC was performed on a Varian ProStar 210 solvent delivery system configured with a Varian ProStar 330 PDA detector. Samples were eluted over a C12 Phenomenex Synergi 2.0×150 mm, 4 µm, 80 Å reverse-phase column. The acidic mobile phase consisted of acetonitrile and water both containing either 0.05% trifluoroacetic acid or 0.1% formic acid (denoted for each compound). Compounds were eluted with a linear gradient of acidic acetonitrile from 5% at 1 min post injection, to 95% at 11 min, followed by isocratic 95% acetonitrile to 15 min (flow rate=1.0 mL/min). LC-MS was performed on a ZMD Micromass mass spectrometer interfaced to an HP Agilent 1100 HPLC instrument equipped with a C12 Phenomenex Synergi 2.0×150 mm, 4 µm, 80 Å reverse phase column. The acidic eluent consisted of a linear gradient of acetonitrile from 5% to 95% in 0.1% aqueous formic acid over 10 min, followed by isocratic 95% acetonitrile for 5 min (flow rate=0.4 mL/min). Preparative HPLC was carried out on a Varian ProStar 210 solvent delivery system configured with a Varian ProStar 330 PDA detector. Products were purified over a C12 Phenomenex Synergi 10.0×250 mm, 4 µm, 80 Å reverse phase column eluting with 0.1% formic acid in water (solvent A) and 0.1% formic acid in acetonitrile (solvent B). The purification method consisted of the following gradient of solvent A to solvent B: 90:10 from 0 to 5 min; 90:10 to 10:90 from 5 min to 80 min; followed by isocratic 10:90 for 5 min. The flow rate was 4.6 mL/min with monitoring at 254 nm. NMR spectral data were collected on a Varian Mercury 400 MHz spectrometer. Coupling constants (J) are reported in hertz.

Example 2

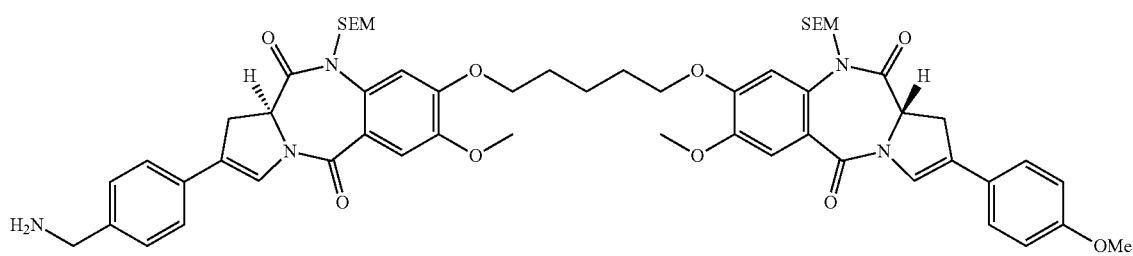

3

↓

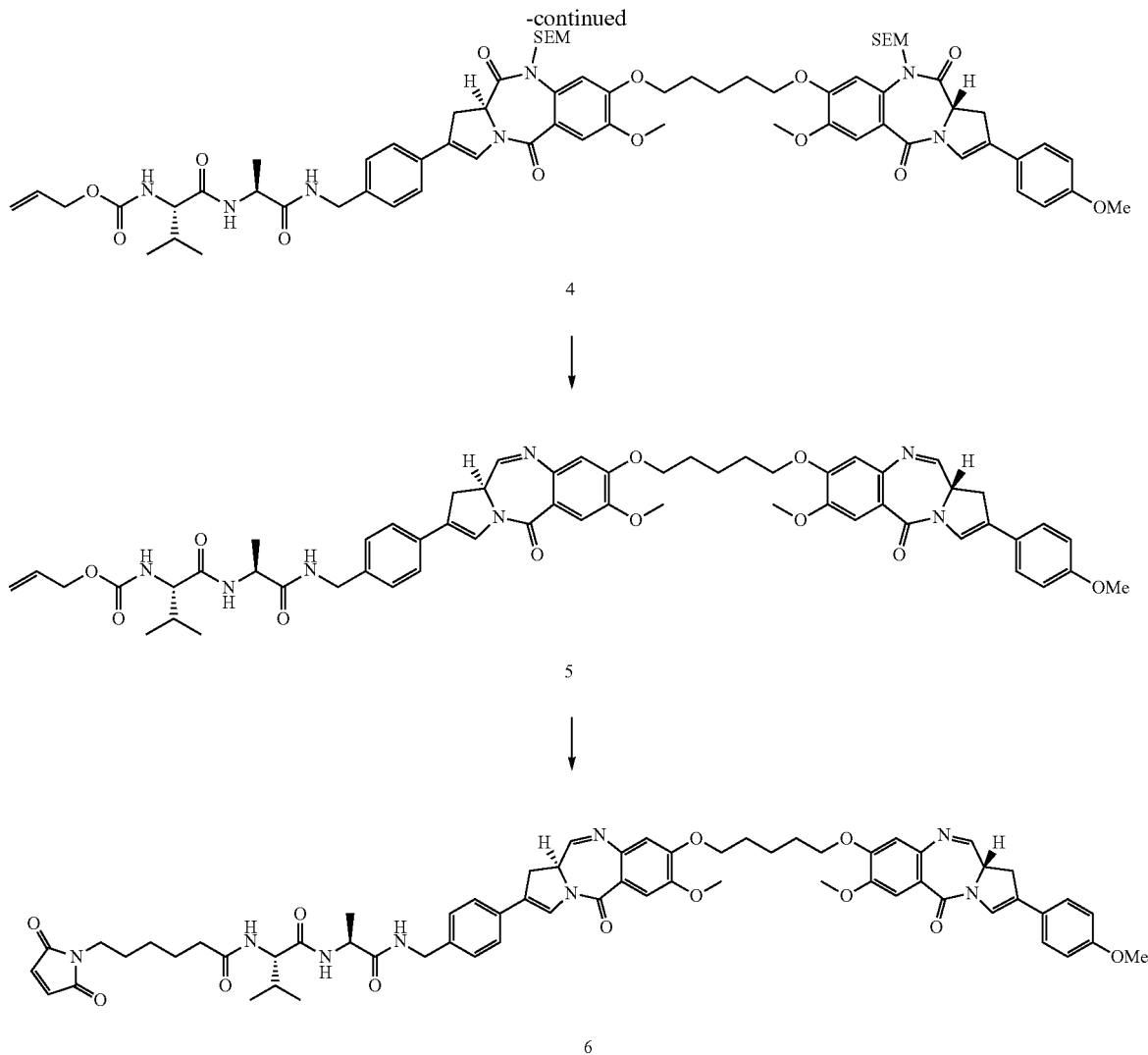

(a) Allyl ((S)-1-((4(S)-1-((4-((S)-7-methoxy-8-((5-(((S)-7-methoxy-2-(4-methoxyphenyl)-5,11-dioxo-10-((2-(trimethylsilyl)ethoxy)methyl)-5,10,11,11a-tetrahydro-1H-benzo[e]pyrrolo[1,2-a][1,4]diazepin-8-yl)oxy)pentyl)oxy)-5,11-dioxo-10-((2-(trimethylsilyl)ethoxy)methyl)-5,10,11,11a-tetrahydro-1H-benzo[e]pyrrolo[1,2-a][1,4]diazepin-2-yl)benzyl)amino)-1-oxopropan-2-yl)amino)-3-methyl-1-oxobutan-2-yl)carbamate (4)

A 10 mL flask was charged with alloc-Val-Ala (15 mg, 57 μmol), EEDQ (17 mg, 69 μmol), and 0.72 mL anhydrous CH$_2$Cl$_2$. Methanol (40 μL) was added to facilitate dissolution and the mixture was stirred under nitrogen for 15 minutes. SEM-dilactam benzylamine 3 (40 mg, 38 μmol) was then added and the reaction was stirred at room temperature for 4 hours, at which time LC-MS revealed conversion to product. The reaction was concentrated, dissolved in minimal CH$_2$Cl$_2$, and purified by radial chromatography on a 1 mm chromatotron plate eluted with CH$_2$Cl$_2$/MeOH mixtures (100:0 to 90:10 CH$_2$Cl$_2$/MeOH) to provide 4 (42 mg, 85%). LC-MS: t$_R$ 15.50 min, m/z (ES$^+$) found 1315.1 (M+H)$^+$.

(b) Allyl ((S)-1-(((S)-1-((4-((S)-7-methoxy-8-((5-(((S)-7-methoxy-2-(4-methoxyphenyl)-5-oxo-5,11a-dihydro-1H-benzo[e]pyrrolo[1,2-a][1,4]diazepin-8-yl)oxy)pentyl)oxy)-5-oxo-5,11a-dihydro-1H-benzo[e]pyrrolo[1,2-a][1,4]diazepin-2-yl)benzyl)amino)-1-oxopropan-2-yl)amino)-3-methyl-1-oxobutan-2-yl)carbamate (5)

A 10 mL flame-dried flask was charged with 4 (40 mg, 30 μmol) and anhydrous THF (0.6 mL), and cooled to −78° C. Lithium triethylborohydride (60 μL of a 1 M THF solution) was added dropwise and the reaction was stirred under nitrogen at −78 C for 2 h, at which time LC-MS revealed roughly 50% conversion. An additional 30 μl of reductant was then added and stirring continued for two additional hours, at which time the reaction was complete. The reaction was then quenched via addition of 1 mL water and warmed to room temperature, then diluted with 25 mL brine and extracted three times with 25 mL dichloromethane. The combined organics were washed with brine, dried over sodium sulfate, and concentrated to dryness. The residue obtained was dissolved in chloroform (0.75 mL), ethanol (2 mL, and water (0.3 mL), and 800 mg of silica gel was added, providing a thick slurry that was sealed and stirred at room temperature for four days. TLC analysis at that time revealed conversion to imine 5. The silica gel was then filtered and washed multiple times with 10% methanol in chloroform until no further PBD absorbance was observed in the filtrate. The combined organics were then washed with brine, dried over sodium sulfate, and concentrated to dryness. The residue was then dissolved in minimal $CH_2Cl_2$, and purified by radial chromatography on a 1 mm chromatotron plate eluted with $CH_2Cl_2$/MeOH mixtures (100:0 to 90:10 $CH_2Cl_2$/MeOH) to provide 3 (19 mg, 61%). Analytical HPLC: $t_R$ 11.99 min. LC-MS: $t_R$ 12.76 min, m/z ($ES^+$) found 1022.4 $(M+H)^+$.

(c) 6-(2,5-Dioxo-2,5-dihydro-1H-pyrrol-1-yl)-N—((S)-1-(((S)-1-((4-((S)-7-methoxy-8-((5-(((S)-7-methoxy-2-(4-methoxyphenyl)-5-oxo-5,11a-dihydro-1H-benzo[e]pyrrolo[1,2-a][1,4]diazepin-8-yl)oxy)pentyl)oxy)-5-oxo-5,11a-dihydro-1H-benzo[e]pyrrolo[1,2-a][1,4]diazepin-2-yl)benzyl)amino)-1-oxopropan-2-yl)amino)-3-methyl-1-oxobutan-2-yl)hexanamide (6)

Alloc-protected di-imine PBD 5 (19 mg, 19 μmol) was added to a flame-dried flask and dissolved in anhydrous dichloromethane (1.9 mL). Triphenylphosphine (0.25 mg, 1 μmol), pyrollidine (3.1 μL, 38 μL), and tetrakis(triphenylphosphine)palladium(0) (0.5 mg, 0.5 μmol) were added, the reaction was then stirred under nitrogen for 30 minutes at room temperature, at which time LC-MS revealed complete alloc-deprotection. The reaction was loaded directly onto a 1 mm chromatotron plate eluted with $CH_2Cl_2$/MeOH mixtures (100:0 to 80:20 $CH_2Cl_2$/MeOH) to provide the free amine (14 mg, 79%). Analytical HPLC: $t_R$ 9.32 min. LC-MS: $t_R$ 11.61 min, m/z ($ES^+$) found 938.5 $(M+H)^+$. The free amine was then dissolved in anhydrous DMF (0.37 mL) and maleimidocaproyl NHS ester was added (6.9 mg, 22 μmol), followed by diisopropylethylamine (13 μL, 75 μL). The reaction was stirred at room temperature for three hours, at which time LC-MS revealed complete consumption of starting material. The reaction mixture was diluted with dichloromethane and purified by radial chromatography on a 1 mm chromatotron plate eluted with $CH_2Cl_2$/MeOH mixtures (100:0 to 90:10 $CH_2Cl_2$/MeOH) to provide 4 (15 mg, 89%). Analytical HPLC: $t_R$ 11.63 min. LC-MS: $t_R$ 12.73 min, m/z ($ES^+$) found 1132.1 $(M+H)^+$.

General Experimental Methods for Examples 3-7.

All commercially available anhydrous solvents were used without further purification. Analytical thin layer chromatography was performed on silica gel 60 F254 aluminum sheets (EMD Chemicals, Gibbstown, N.J.). Radial chromatography was performed on Chromatotron apparatus (Harris Research, Palo Alto, Calif.). Analytical HPLC was performed on a Varian ProStar 210 solvent delivery system configured with a Varian ProStar 330 PDA detector. Samples were eluted over a C12 Phenomenex Synergi 2.0×150 mm, 4 μm, 80 Å reverse-phase column. The acidic mobile phase consisted of acetonitrile and water both containing either 0.05% trifluoroacetic acid or 0.1% formic acid (denoted for each compound). Compounds were eluted with a linear gradient of acidic acetonitrile from 5% at 1 min post injection, to 95% at 11 min, followed by isocratic 95% acetonitrile to 15 min (flow rate=1.0 mL/min). LC-MS was performed on a ZMD Micromass mass spectrometer interfaced to an HP Agilent 1100 HPLC instrument equipped with a C12 Phenomenex Synergi 2.0×150 mm, 4 μm, 80 Å reverse phase column. The acidic eluent consisted of a linear gradient of acetonitrile from 5% to 95% in 0.1% aqueous formic acid over 10 min, followed by isocratic 95% acetonitrile for 5 min (flow rate=0.4 mL/min). Preparative HPLC was carried out on a Varian ProStar 210 solvent delivery system configured with a Varian ProStar 330 PDA detector. Products were purified over a C12 Phenomenex Synergi 10.0×250 mm, 4 μm, 80 Å reverse phase column eluting with 0.1% formic acid in water (solvent A) and 0.1% formic acid in acetonitrile (solvent B). The purification method consisted of the following gradient of solvent A to solvent B: 90:10 from 0 to 5 min; 90:10 to 10:90 from 5 min to 80 min; followed by isocratic 10:90 for 5 min. The flow rate was 4.6 mL/min with monitoring at 254 nm. NMR spectral data were collected on a Varian Mercury 400 MHz spectrometer. Coupling constants (J) are reported in hertz.

Example 3

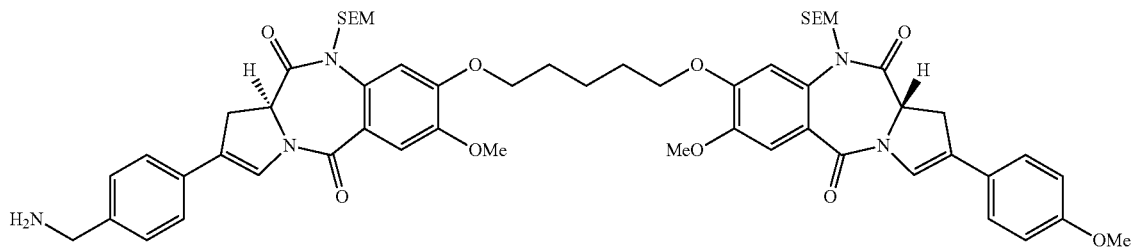

3

↓

-continued

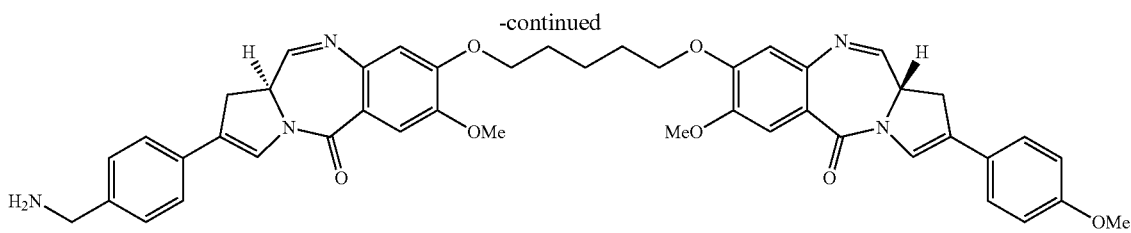

7

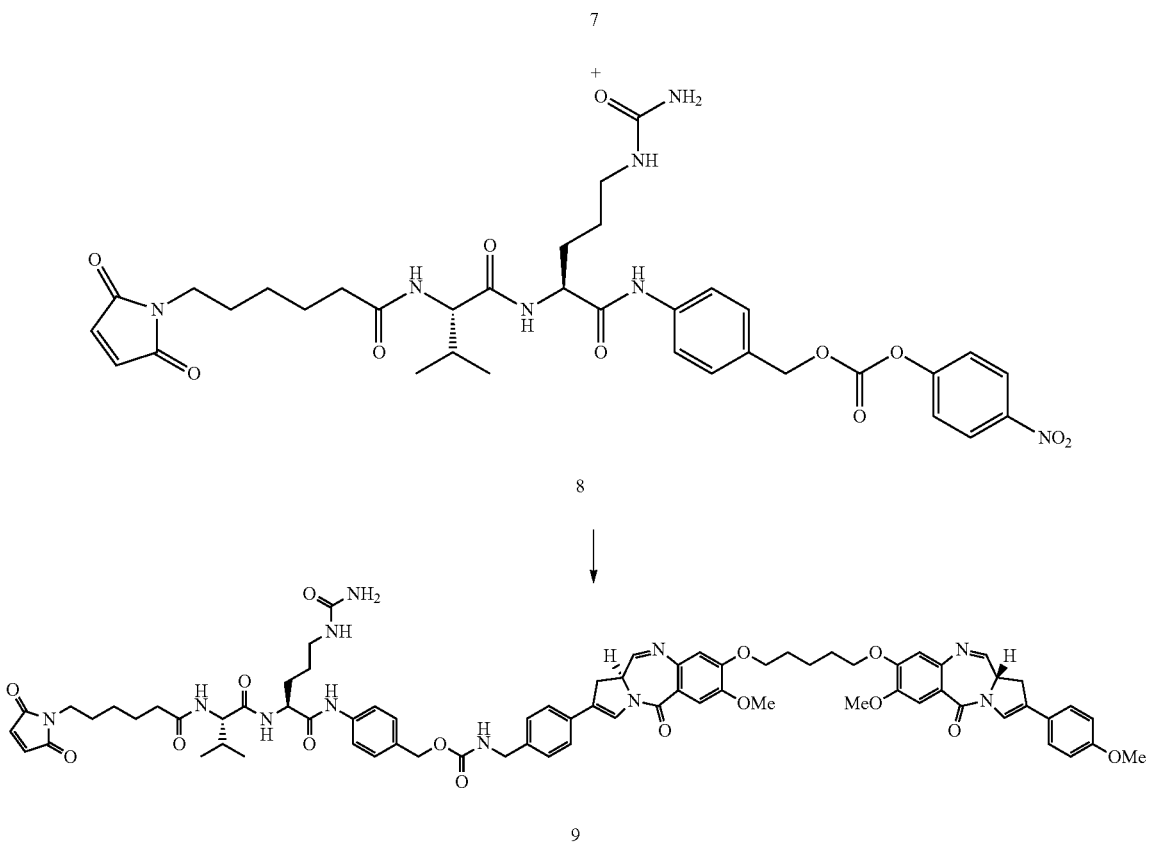

(a) (S)-2-(4-(aminomethyl)phenyl)-7-methoxy-8-((5-(((S)-7-methoxy-2-(4-methoxyphenyl)-5-oxo-5,11a-dihydro-1H-benzo[e]pyrrolo[1,2-a][1,4]diazepin-8-yl)oxy)pentyl)oxy)-1H-benzo[e]pyrrolo[1,2-a][1,4]diazepin-5(11aH)-one (7)

A flame-dried flask was charged with SEM dilactam 3 (100 mg, 94 µmol, 1 eq) dissolved in anhydrous tetrahydrofuran (THF, 1.9 mL), and cooled to −78° C. Lithium triethylborohydride (0.19 mL of a 1 M solution in THF, 188 µmol, 2 eq) was added dropwise and the reaction was stirred under nitrogen for 1 hour, at which time LC revealed incomplete conversion to product. An additional 0.1 mL of reductant was added and the reaction was stirred for one more hour. The reaction was quenched through the addition of water (3 mL) and allowed to warm to room temperature, then diluted with brine (25 mL) and extracted three times with dichloromethane (25 mL). The combined organics were washed with brine (25 mL), dried over sodium sulfate, and evaporated to dryness. The residue was dissolved in a mixture of dichloromethane (2.4 mL), ethanol (6.2 mL), and water (0.9 mL), and silica gel (2.4 g) was added. The resulting slurry was stirred at room temperature for 3 days.

TLC analysis revealed conversion to imine 7, at which time the slurry was filtered over a sintered glass funnel and the silica gel cake was washed with 10% methanol in chloroform until no further PBD absorbance was observed in the filtrate. Concentration of the filtrate provided 70 mg of crude imine dimer 7, which was split and 40 mg taken forward for purification. The material was dissolved in minimal dichloromethane and purified by radial chromatography on a 1 mm chromatotron plate eluted with $CH_2Cl_2$/MeOH mixtures (100:0 to 80:20) to provide 7 (11 mg, 27% from split material). TLC: $R_f$=0.21, 20% MeOH in $CH_2Cl_2$. LC-MS: $t_R$ 11.30 min, m/z ($ES^+$) found 768.3 $(M+H)^+$.

(b) 4-((S)-2-((S)-2-(6-(2,5-dioxo-2,5-dihydro-1H-pyrrol-1-yl)hexanamido)-3-methylbutanamido)-5-ureidopentanamido)benzyl 4-(((S)-7-methoxy-8-((5-(((S)-7-methoxy-2-(4-methoxyphenyl)-5-oxo-5,11a-dihydro-1H-benzo[e]pyrrolo[1,2-a][1,4]diazepin-8-yl)oxy)pentyl)oxy)-5-oxo-5,11a-dihydro-1H-benzo[e]pyrrolo[1,2-a][1,4]diazepin-2-yl)benzylcarbamate (9)

A flame-dried flask was charged with benzylamine 7 (7.3 mg, 9.5 µmol, 1 eq) dissolved in anhydrous dimethylformamide (0.2 mL). Maleimidocaproyl-Valine-Citrulline-PAB-OCO-pNP (Dubowchik et al., *Bioconjugate Chemistry*, 2002, 13, 855-869) (7 mg, 9.5 µmol, 1 eq) was added, followed by diisopropylethylamine (16.5 µL, 95 µmol, 10 eq), the reaction was then stirred at room temperature under a nitrogen atmosphere. LC revealed conversion to product after 1.5 hours; the reaction was diluted with dichloromethane and loaded directly on to a 1 mm chromatotron plate eluted with $CH_2Cl_2$/MeOH mixtures (100:0 to 80:20) to provide purified drug linker 9 (9.3 mg, 72%). TLC: $R_f$=0.24, 10% MeOH in $CH_2Cl_2$. LC-MS: $t_R$ 12.61 min, m/z (ES$^+$) found 1366.8 (M+H)$^+$.

Example 4

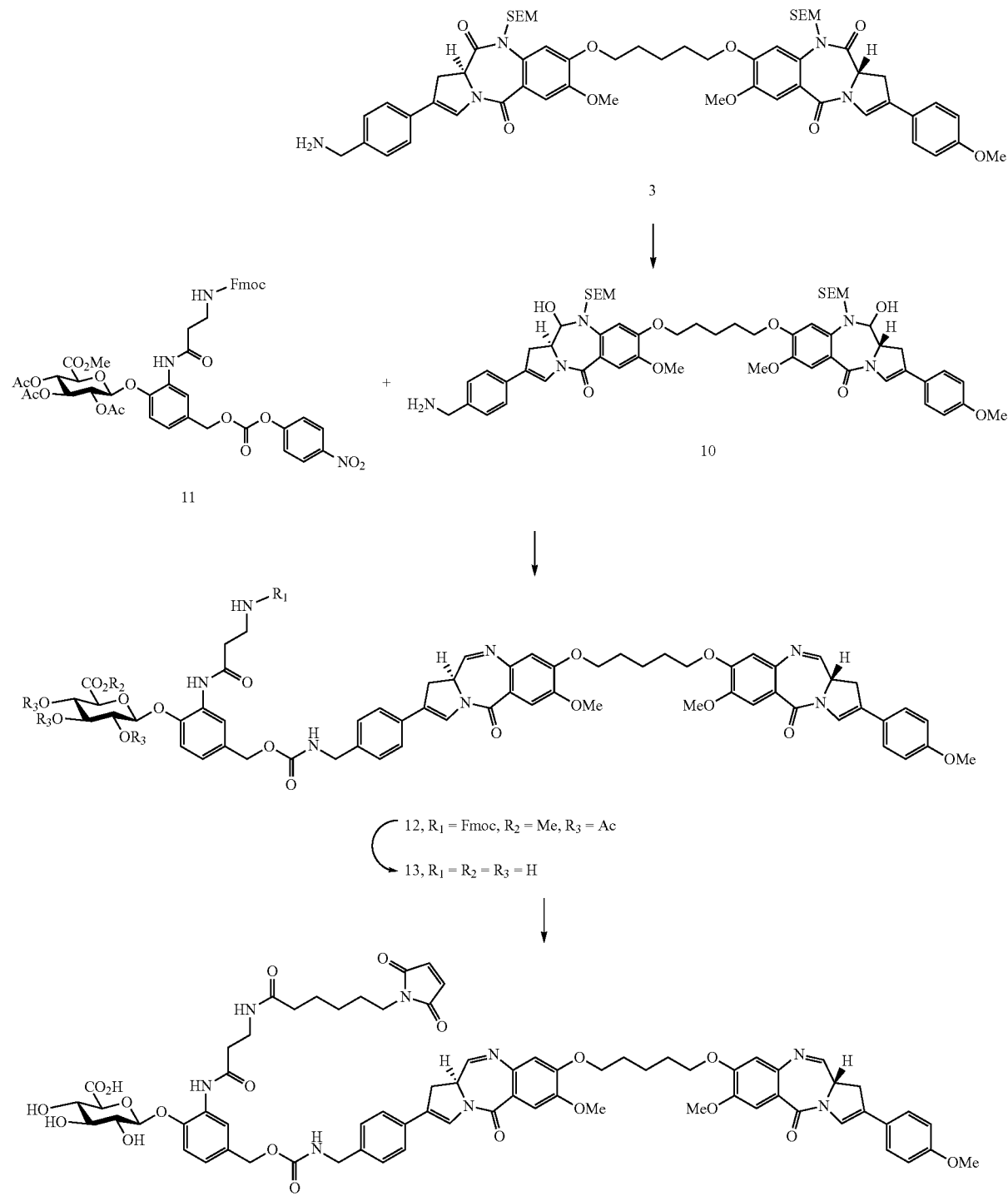

(a) (2S,3R,4S,5R,6R)-2-(2-(3-((((9H-fluoren-9-yl)methoxy)carbonyl)amino)propanamido)-4-(((((4-(((S)-7-methoxy-8-((5-(((S)-7-methoxy-2-(4-methoxyphenyl)-5-oxo-5,11a-dihydro-1H-benzo[e]pyrrolo[1,2-a][1,4]diazepin-8-yl)oxy)pentyl)oxy)-5-oxo-5,11a-dihydro-1H-benzo[e]pyrrolo[1,2-a][1,4]diazepin-2-yl)benzyl)carbamoyl)oxy)methyl)phenoxy)-6-methyltetrahydro-2H-pyran-3,4,5-triyl triacetate (12)

A flame-dried flask was charged with SEM dilactam 3 (40 mg, 38 μmol, 1 eq) dissolved in anhydrous tetrahydrofuran (0.8 mL), and cooled to −78° C. Lithium triethylborohydride (80 μL of a 1 M solution in THF, 76 μmol, 2 eq) was added dropwise and the reaction was stirred under nitrogen for 1.5 hours, at which time LC revealed incomplete conversion to product. An additional 40 μL of reductant was added and the reaction was stirred for one more hour. The reaction was quenched through the addition of water (1 mL) and allowed to warm to room temperature, then diluted with brine (25 mL) and extracted three times with dichloromethane (25 mL). The combined organics were washed with brine (25 mL), dried over sodium sulfate, and evaporated to dryness. The SEM carbinolamine 10 (39 mg) was carried forward without further purification. Activated glucuronide linker 11 (Jeffrey et al., *Bioconjugate Chemistry*, 2006, 17, 831-840) (38 mg, 42 μmol, 1.1 eq) was dissolved in anhydrous dimethylformamide (0.6 mL) and added to a flask containing 10 (39 mg, 37 μmol, 1 eq). Diisopropylethylamine (13 μL, 74 μmol, 2 eq) was added and the reaction was stirred at room temperature under nitrogen; after 1.5 hours LC-MS revealed conversion to the coupled product. The reaction was diluted with brine (25 mL) and extracted three times with dichloromethane (25 mL). The combined organics were washed with brine (25 mL), dried over sodium sulfate, and evaporated to dryness. The residue obtained was dissolved in a mixture of chloroform (0.7 mL), ethanol (1.25 mL), and water (0.17 mL), and silica gel (1 g) was added. The resulting slurry was stirred at room temperature for 3 days. TLC analysis revealed conversion to drug-linker 12, at which time the slurry was filtered over a sintered glass funnel and the silica gel cake was washed with 10% methanol in chloroform until no further PBD absorbance was observed in the filtrate. Concentration of the filtrate provided crude product 12. The material was dissolved in minimal dichloromethane and purified by radial chromatography on a 1 mm chromatotron plate eluted with $CH_2Cl_2$/MeOH mixtures (100:0 to 80:20) to provide 12 (25 mg, 36%). LC-MS: m/z (ES$^+$) found 1542.9 (M+H)$^+$.

(b) (2S,3S,4S,5R,6S)-6-(2-(3-aminopropanamido)-4-(((((4-(((S)-7-methoxy-8-((5-(((S)-7-methoxy-2-(4-methoxyphenyl)-5-oxo-5,11a-dihydro-1H-benzo[e]pyrrolo[1,2-a][1,4]diazepin-8-yl)oxy)pentyl)oxy)-5-oxo-5,11a-dihydro-1H-benzo[e]pyrrolo[1,2-a][1,4]diazepin-2-yl)benzyl)carbamoyl)oxy)methyl)phenoxy)-3,4,5-trihydroxytetrahydro-2H-pyran-2-carboxylic acid (13)

Protected glucuronide linker 12 (25 mg, 16 μmol, 1 eq) was dissolved in methanol (0.5 mL) and tetrahydrofuran (0.5 mL), and the cooled to 0° C. Lithium hydroxide monohydrate (4 mg, 96 μmol, 6 eq) was dissolved in water (0.5 mL) and added dropwise to the reaction, which was then allowed to warm to room temperature and monitored by LC-MS. Additional LiOH (3.2 mg, 76 μmol, 4.8 eq) in 0.4 mL of water was added to the reaction after 2 h to further drive conversion to product. Glacial acetic acid (11 μL, 195 μmol, 12 eq) was added, followed by 1 mL of dimethylsulfoxide, the volatile solvents were then removed by rotary evaporation. The crude product was purified by preparative HPLC to provide deprotected glucuronide linker 13 (2 mg, 11%). LC-MS: $t_R$ 11.54 min, m/z (ES$^+$) found 1180.0 (M+H)$^+$.

(c) (2S,3S,4S,5R,6S)-6-(2-(3-(6-(2,5-dioxo-2,5-dihydro-1H-pyrrol-1-yl)hexanamido)propanamido)-4-(((((4-(((S)-7-methoxy-8-((5-(((S)-7-methoxy-2-(4-methoxyphenyl)-5-oxo-5,11a-dihydro-1H-benzo[e]pyrrolo[1,2-a][1,4]diazepin-8-yl)oxy)pentyl)oxy)-5-oxo-5,11a-dihydro-1H-benzo[e]pyrrolo[1,2-a][1,4]diazepin-2-yl)benzyl)carbamoyl)oxy)methyl)phenoxy)-3,4,5-trihydroxytetrahydro-2H-pyran-2-carboxylic acid (14)

A flame-dried flask was charged with glucuronide linker 13 (2 mg, 1.7 μmol, 1 eq), maleimidocaproic acid N-hydroxysuccinimide ester (0.8 mg, 2.6 μmol, 1.5 eq), and anhydrous dimethylformamide (85 μL). Diisopropylethylamine (1.5 uL, 8.5 μmol, 5 eq) was added, the reaction was then stirred at room temperature under nitrogen. After 2 hours HPLC revealed conversion to product. The reaction was diluted in dimethylsulfoxide and purified by preparative HPLC to provide PBD glucuronide linker 14 (1.4 mg, 61%). LC-MS: $t_R$ 12.30 min, m/z (ES$^+$) found 1373.7 (M+H)$^+$.

Example 5

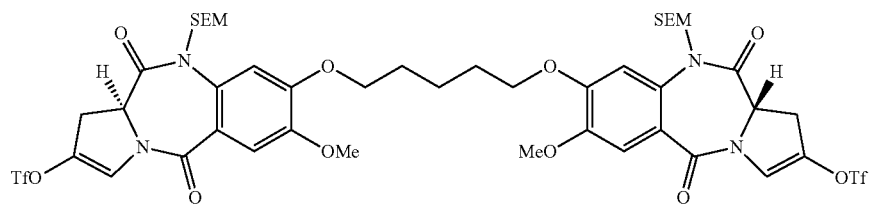

1

↓

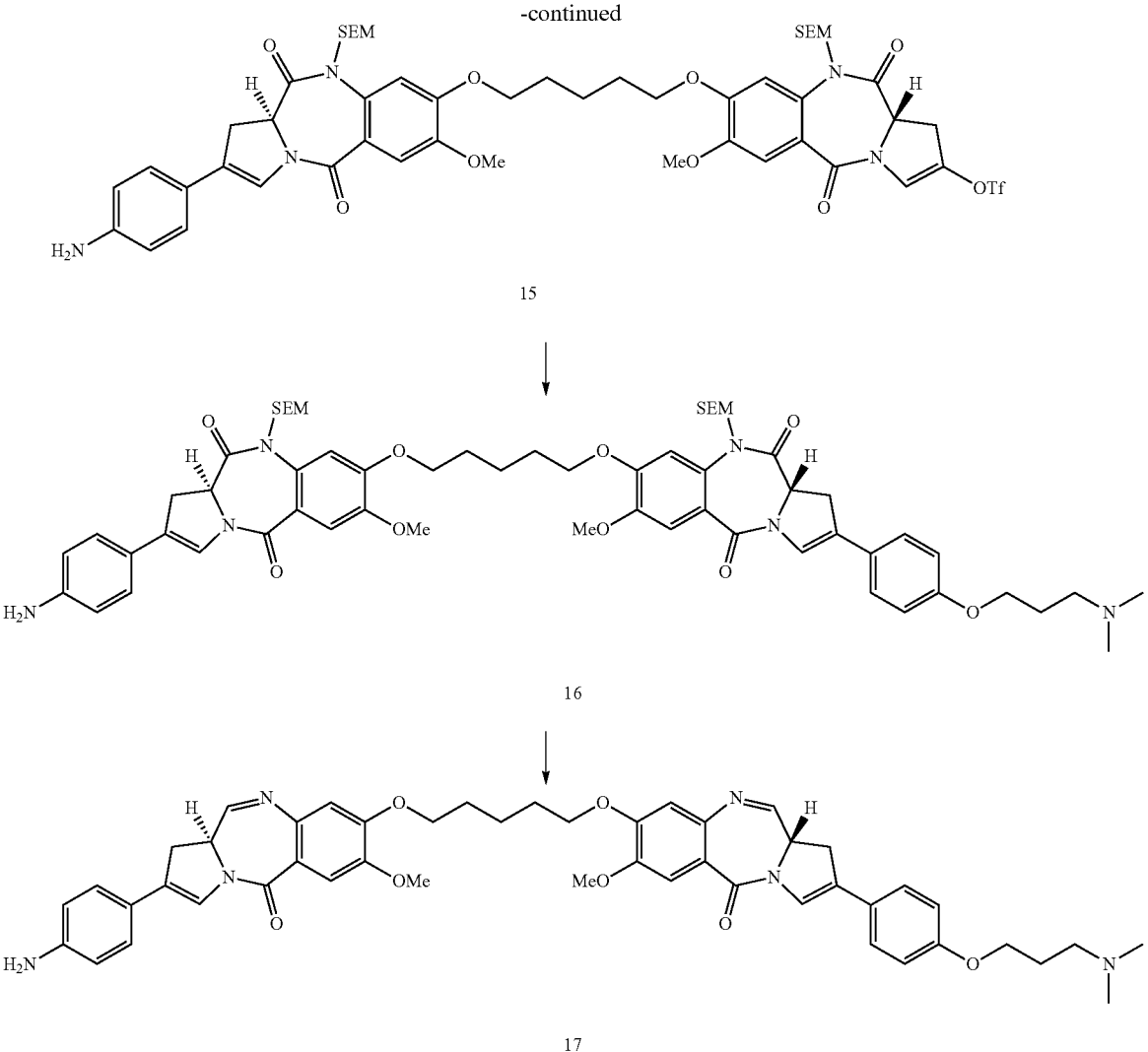

(a) (S)-8-(((5-(((S)-2-(4-aminophenyl)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-8-yl)oxy)pentyl)oxy)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-2-yl trifluoromethanesulfonate (15)

A flask was charged with bis triflate 1 (500 mg, 437 μmol, 1 eq) dissolved in toluene (6.5 mL), ethanol (3.2 mL), and water (3.2 mL). To the stirred solution was added 4-aminophenylboronic acid pinacol ester (87 mg, 398 μmol, 0.91 eq), sodium carbonate (213 mg, 2.0 mmol, 4.6 eq), and tetrakis(triphenylphosphine)palladium(0) (20 mg, 17.5 μmol, 0.04 eq), the reaction was stirred vigorously at room temperature under nitrogen with monitoring by LC-MS. After three hours the reaction had proceeded to approximately 50% conversion to desired product. The reaction was concentrated and then partitioned between ethyl acetate (100 mL) and water (100 mL). The organic layer was then washed with water (100 mL), brine (100 mL), dried over sodium sulfate, and concentrated to dryness to provide crude aniline triflate 15. The crude product was purified by flash chromatography, eluting with mixtures of hexanes:ethyl acetate (60:40 to 30:70), to provide pure aniline triflate 15 (118 mg, 25%). TLC: $R_f$=0.43, 25% hexanes in ethyl acetate. LC-MS: $t_R$ 8.30 min, m/z (ES$^+$) found 1088.2 (M+H)$^+$.

(b) (S)-2-(4-aminophenyl)-8-((5-(((S)-2-(4-(3-(dimethylamino)propoxy)phenyl)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-8-yl)oxy)pentyl)oxy)-7-methoxy-10-((2-(trimethylsilyl)ethoxy)methyl)-1H-benzo[e]pyrrolo[1,2-a][1,4]diazepine-5,11(10H,11aH)-dione (16)

A flask was charged with aniline triflate 15 (118 mg, 109 μmol, 1 eq) dissolved in toluene (0.7 mL), ethanol (2.3 mL), and water (0.3 mL). To the stirred solution was added 4-[3-(dimethylamino)propyloxy]phenylboronic acid pinacol ester (43 mg, 142 μmol, 1.3 eq), sodium carbonate (53 mg, 0.5 mmol, 4.6 eq), and tetrakis(triphenylphosphine)palladium(0) (5 mg, 4.4 μmol, 0.04 eq), the reaction was stirred vigorously at room temperature under nitrogen with monitoring by LC-MS. After four hours the reaction had reached completion. The reaction was concentrated and then partitioned between ethyl acetate (25 mL) and water (25 mL).

The aqueous layer was extracted two times with ethyl acetate (25 mL). The organic layer was then washed with water (50 mL), brine (50 mL), dried over sodium sulfate, and concentrated to dryness to provide crude SEM dilactam 16. The crude product was purified by flash chromatography, eluting with mixtures of hexanes:ethyl acetate (50:50 to 0:100), to provide pure product 16 (78 mg, 64%). TLC: $R_f$=0.38, 20% methanol in $CH_2Cl_2$. LC-MS: m/z ($ES^+$) found 1117.8 $(M+H)^+$. $^1H$ NMR (d7-DMF) δ (ppm) 0.00 (s, 18H), 0.90 (m, 4H), 1.74 (m, 3H), 1.96 (m, 6H), 2.21 (s, 6H), 2.44 (t, J=7.2 Hz, 2H), 3.25 (m, 2H), 3.62 (m, 4H), 3.80 (m, 2H), 3.96 (s, 6H), 4.11 (t, J=6.4 Hz, 2H), 4.20 (m, 3H), 4.92 (m, 2H), 5.31 (dd, J=6, 10 Hz, 2H), 5.48 (m, 4H), 6.73 (t, J=8.4 Hz, 2H), 7.01 (t, J=8.8 Hz, 2H), 7.29 (m, 3H), 7.40 (m, 4H), 7.47 (m, 1H), 7.56 (t, J=8.4 Hz, 2H).

(c) (S)-2-(4-aminophenyl)-8-((5-(((S)-2-(4-(3-(dimethylamino)propoxy)phenyl)-7-methoxy-5-oxo-5,11a-dihydro-1H-benzo[e]pyrrolo[1,2-a][1,4]diazepin-8-yl)oxy)pentyl)oxy)-7-methoxy-1H-benzo[e]pyrrolo[1,2-a][1,4]diazepin-5(11 aH)-one (17)

A flame-dried flask was charged with SEM dilactam 16 (70 mg, 63 μmol, 1 eq) dissolved in anhydrous tetrahydrofuran (1.3 mL), and cooled to −78° C. Lithium triethylborohydride (0.13 mL of a 1 M solution in THF, 126 μmol, 2 eq) was added dropwise and the reaction was stirred under nitrogen for 1.5 h, at which time LC revealed incomplete conversion to product. An additional 65 μL of reductant was added and the reaction was stirred for one more hour. The reaction was quenched through the addition of water (1 mL) and allowed to warm to room temperature, then diluted brine (25 mL) and extracted three times with dichloromethane (25 mL). The combined organics were washed with brine (25 mL), dried over sodium sulfate, and evaporated to dryness. The residue was dissolved in a mixture of dichloromethane (1.2 mL), ethanol (3.2 mL), and water (0.5 mL), and silica gel (1.6 g) was added. The resulting slurry was stirred at room temperature for 4 days. TLC analysis revealed conversion to imine dimer 17, at which time the slurry was filtered over a sintered glass funnel and the silica gel cake was washed with 10% methanol in chloroform until no further PBD absorbance was observed in the filtrate. Concentration of the filtrate provided crude imine dimer 17. The material was dissolved in minimal dichloromethane and purified by radial chromatography on a 1 mm chromatotron plate eluted with $CH_2Cl_2$/MeOH mixtures (100:0 to 60:40) to provide 17 (31 mg, 60%). LC-MS: $t_R$ 11.14 min, m/z ($ES^+$) found 825.4 $(M+H)^+$.

Example 6

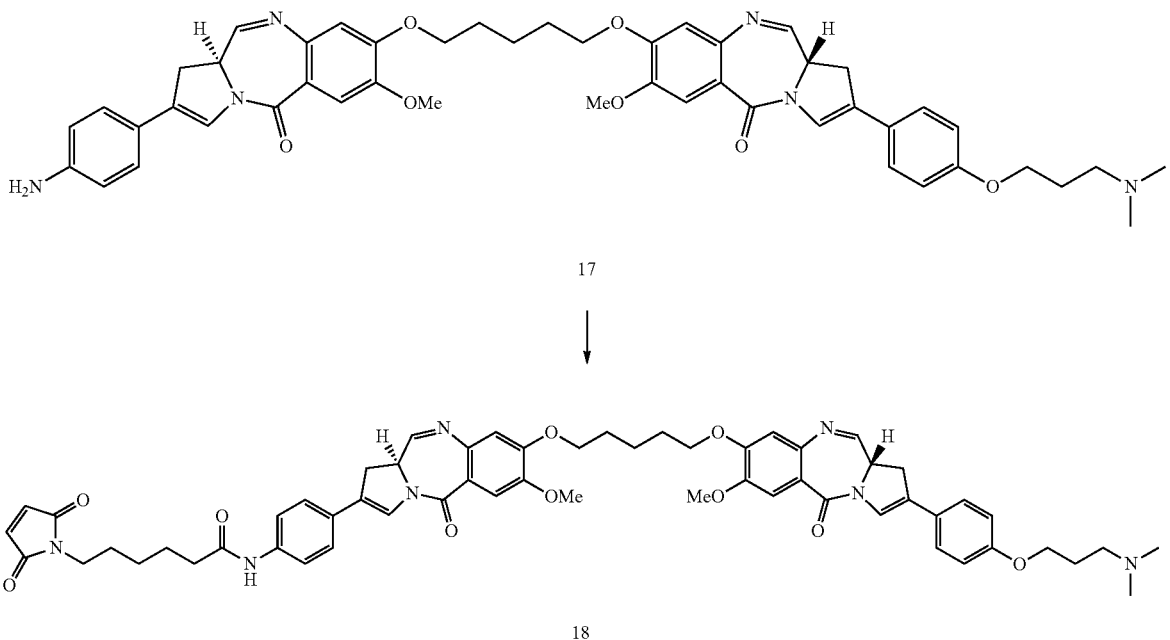

N-(4-(((S)-8-((5-(((S)-2-(4-(3-(dimethylamino)propoxy)phenyl)-7-methoxy-5-oxo-5,11a-dihydro-1H-benzo[e]pyrrolo[1,2-a][1,4]diazepin-8-yl)oxy)pentyl)oxy)-7-methoxy-5-oxo-5,11a-dihydro-1H-benzo[e]pyrrolo[1,2-a][1,4]diazepin-2-yl)phenyl)-6-(2,5-dioxo-2,5-dihydro-1H-pyrrol-1-yl)hexanamide (18)

A flame-dried flask was charged with maleimidocaproic acid (5.2 mg, 25 μmol, 1.5 eq) dissolved in 0.33 mL of 5% methanol in anhydrous dichloromethane. The acid was preactivated by addition of N-ethoxycarbonyl-2-ethoxy-1,2-dihydroquinoline (7.3 mg, 30 μmol, 1.8 eq), followed by stirring at room temperature under nitrogen for 15 minutes. The activated acid was then added to a flame-dried flask containing PBD dimer 17 (13.5 mg, 16 μmol, 1 eq). The reaction was stirred for 4 h at room temperature under nitrogen, at which time LC-MS revealed conversion to product. The material was diluted in dichloromethane and purified by radial chromatography on a 1 mm chromatotron plate eluted with $CH_2Cl_2$/MeOH mixtures (100:0 to 80:20) to provide 18 (7.3 mg, 44%). LC-MS: $t_R$ 9.09 min, m/z ($ES^+$) found 1018.3 $(M+H)^+$.

Example 7

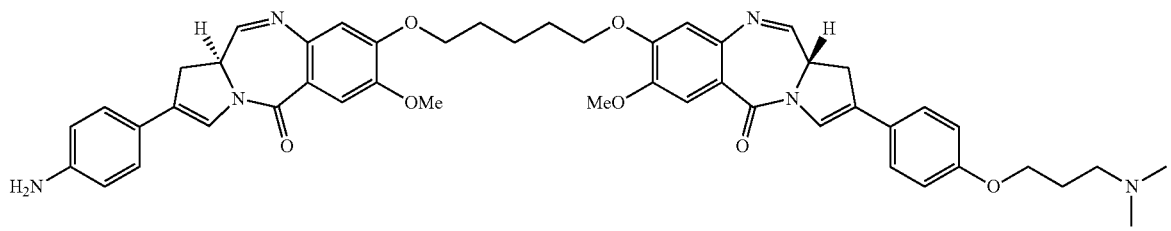

17

↓

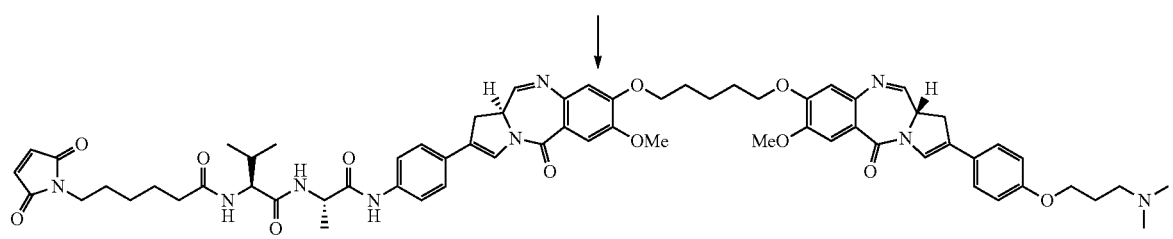

19

N—((S)-1-(((S)-1-((4-((S)-8-((5-(((S)-2-(4-(3-(dimethylamino)propoxy)phenyl)-7-methoxy-5-oxo-5,11a-dihydro-1H-benzo[e]pyrrolo[1,2-a][1,4]diazepin-8-yl)oxy)pentyl)oxy)-7-methoxy-5-oxo-5,11a-dihydro-1H-benzo[e]pyrrolo[1,2-a][1,4]diazepin-2-yl)phenyl)amino)-1-oxopropan-2-yl)amino)-3-methyl-1-oxobutan-2-yl)-6-(2,5-dioxo-2,5-dihydro-1H-pyrrol-1-yl)hexanamide (19)

A flame-dried flask was charged with maleimidocaproyl-valine-alanine linker (Compound 36 in Example 13 of WO 2011/130613 A1) (9 mg, 24 μmol, 1.5 eq) dissolved in 0.33 mL of 5% methanol in anhydrous dichloromethane. The acid was pre-activated by addition of N-ethoxycarbonyl-2-ethoxy-1,2-dihydroquinoline (7.1 mg, 29 μmol, 1.8 eq), followed by stirring at room temperature under nitrogen for 15 minutes. The activated acid was then added to a flame-dried flask containing PBD dimer 17 (13 mg, 16 μmol, 1 eq). The reaction was stirred for 7 h at room temperature under nitrogen, at which time LC-MS revealed conversion to product. The material was diluted in dichloromethane and purified by radial chromatography on a 1 mm chromatotron plate eluted with CH$_2$Cl$_2$/MeOH mixtures (100:0 to 80:20) to provide 19 (5.1 mg, 27%). LC-MS: t$_R$ 9.09 min, m/z (ES$^+$) found 1188.4 (M+H)$^+$.

Example 8

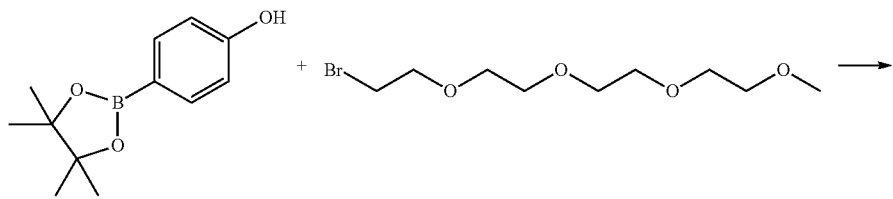

20

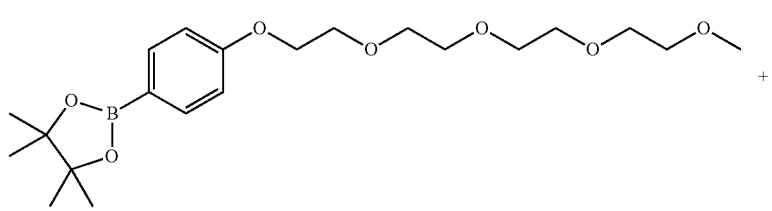

21

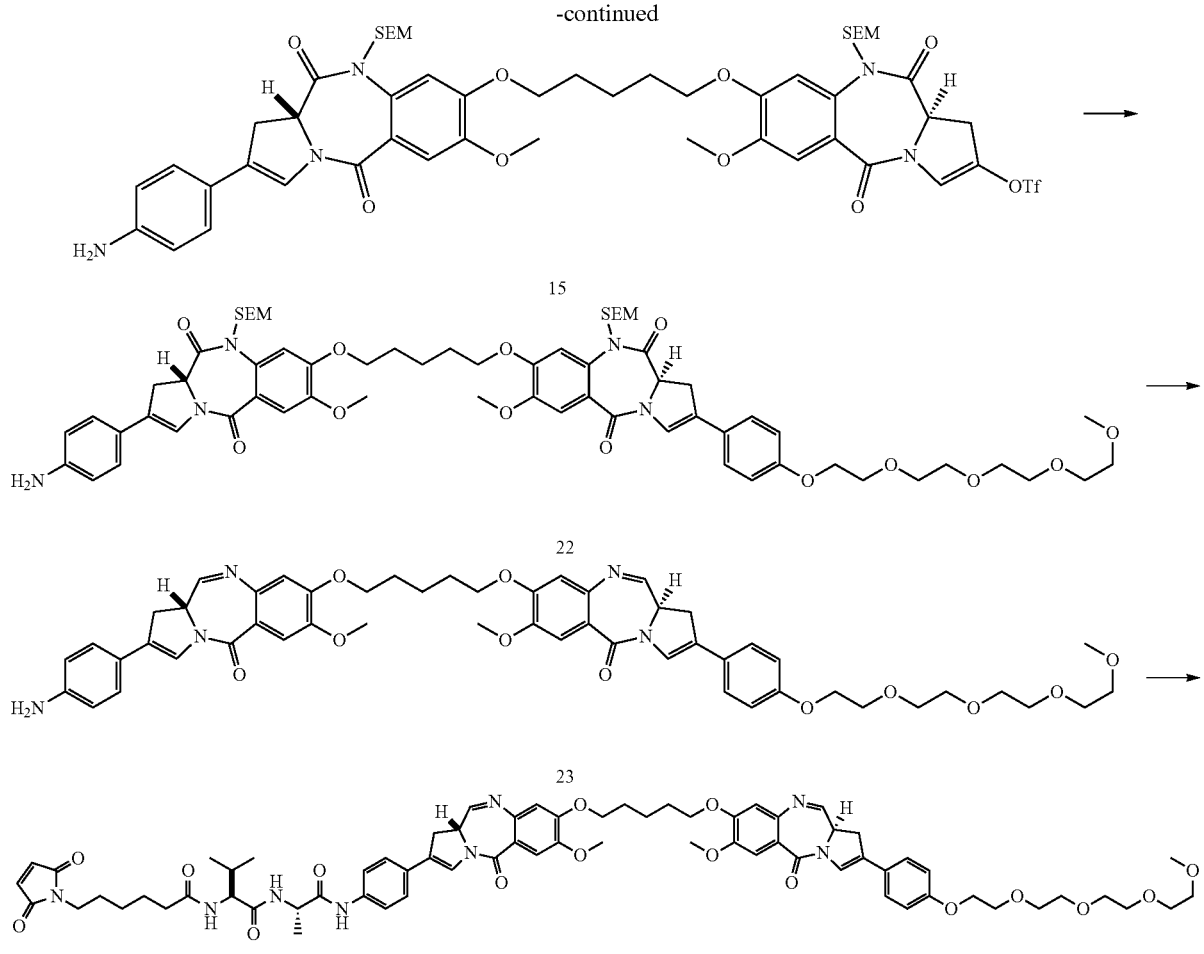

(a) 2-(4-(2,5,8,11-tetraoxatridecan-13-yloxy)phenyl)-4,4,5,5-tetramethyl-1,3,2-dioxaborolane (21)

To a mixture of 4-hydroxyphenylboronic acid pinacol ester (880 mg, 4 mmol), bromomethyltetraethylene glycol (1.6 g, 6 mmol) and DMF (10 ml) was added Cs$_2$CO$_3$ (1.5 g; 8 mmol). The reaction mixture was stirred for ~65 h, and was poured into ethyl acetate (100 mL). The mixture was washed with 0.1 N HCl (200 mL), water (3×100 mL) and brine (50 mL) and the organic phase was dried over Na$_2$SO$_4$. Decanting and concentration gave a brown oil which was purified on a 2 mm radial chromatotron plate eluting with 50% ethyl acetate in hexanes followed by 100% ethyl acetate to give 1.21 g (74%): NMR (d6-DMSO, 400 MHz) ☐ 7.59 (d, J=8.6 Hz, 2H), 6.93 (d, J=8.6 Hz, 2H), 4.11 (t, J=4.7 Hz, 2H), 3.73 (m, 2H), 3.60-3.45 (m, 14H), 3.41 (m, 2H), 3.23 (s, 3H), 1.27 (s, 12H); LC-MS: m/z (ES+) found 433.64 (M+Na)$^+$.

(b) (R)-2-(4-(2,5,8,11-tetraoxatridecan-13-yloxy)phenyl)-8-((5-(((R)-2-(4-aminophenyl)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-8-yl)oxy)pentyl)oxy)-7-methoxy-10-((2-(trimethylsilyl)ethoxy)methyl)-1H-benzo[e]pyrrolo[1,2-a][1,4]diazepine-5,11(10H,11aH)-dione (22)

To a mixture of the monotriflate 15 (200 mg, 0.18 mmol) and TEG boronate ester (111 mg, 0.27 mmol) in a mixture of toluene (2 mL) and ethanol (1 mL) was added 2M Na$_2$CO$_3$ (0.5 mL) and tetrakis Pd (6 mg, 0.054 mmol). After stirring at room temperature for 3 h, the reaction mixture was poured into ethyl acetate, washed with water (3×50 mL) and brine (50 mL) and was dried over Na$_2$SO$_4$. The solution was decanted, concentrated and then purified on a 2 mm radial chromatotron plate eluting with 5% methanol in dichloromethane. This gave 207 mg (94%) as a yellow solid: $^1$H NMR (CDCl$_3$, 400 MHz) ☐ 7.39-7.34 (m, 7H), 7.26 (m, 2H), 6.89 (d, J=9.0 Hz, 2H), 6.66 (d, J=8.6 Hz, 2H), 4.70 (dd, J=10.2, 2.0 Hz, 2H), 4.18-4.03 (m, 8H), 3.93 (s, 3H), 3.90-3.62 (m, 21H), 3.55 (dd, J=5.1, 3.2 Hz, 2H) 3.38 (s, 3H), 3.12 (pent, J=5.0H, 2H), 2.05 (m, 6H), 1.72 (m, 2H), 1.0 (m, 4H), 0.3 (s, 18H); LC-MS: m/z (ES+) found 1222.98 (M+H)$^+$.

(c) (R)-2-(4-(2,5,8,11-tetraoxatridecan-13-yloxy)
phenyl)-8-((5-(((R)-2-(4-aminophenyl)-7-methoxy-
5-oxo-5,11a-dihydro-1H-benzo[e]pyrrolo[1,2-a][1,4]
diazepin-8-yl)oxy)pentyl)oxy)-7-methoxy-1H-benzo
[e]pyrrolo[1,2-a][1,4]diazepin-5(11aH)-one (23)

To a mixture of the SEM dilactam (207 mg, 0.17 mmol) in THF (10 mL) at −78° C. was added Superhydride (LiHBEt₄ as a 1N solution in THF, 0.34 mL, 0.34 mmol). The reaction mixture was stirred for approximately 2 h, at which time LC-MS analysis of the reaction mixture revealed approximately 50% conversion to fully reduced SEM-carbinolamine intermediate, with mono-reduced material still present. An additional aliquot of Superhydride (0.34 mL, 0.34 mmol) was added and the reaction was stirred at −78° C. for an additional hour. LC-MS inspection revealed that the reaction still had not progressed to completion, therefore a third aliquot of Superhydride (0.34 mL, 0.34 mmol) was added and the reaction mixture was placed in a −80° C. freezer for 16 hours. The reaction mixture was then quenched with water (5 mL), allowed to warm to an ambient temperature and was poured into ethyl acetate (100 mL). After washing with brine, the mixture was dried over Na₂SO₄. The organic phase was decanted, concentrated under reduced pressure, and then treated with a mixture of ethanol (14 mL) dichloromethane (5 mL), waster (7 mL) and silica gel (5 g) for 72 hours. The mixture was filtered through a fritted glass funnel and washed several times with 10% methanol in dichloromethane, before the solution was concentrated under reduced pressure. The mixture was purified on a 2 mm radial chromatotron plate eluting with 5% methanol in dichloromethane to give 46 mg (29%): LC-MS: m/z (ES+) found 930.85 (M+H)⁺.

(d) N—((S)-1-(((S)-1-((4-((R)-8-((5-(((R)-2-(4-(2,5,
8,11-tetraoxatridecan-13-yloxy)phenyl)-7-methoxy-
5-oxo-5,11a-dihydro-1H-benzo[e]pyrrolo[1,2-a][1,4]
diazepin-8-yl)oxy)pentyl)oxy)-7-methoxy-5-oxo-5,
11a-dihydro-1H-benzo[e]pyrrolo[1,2-a][1,4]
diazepin-2-yl)phenyl)amino)-1-oxopropan-2-yl)
amino)-3-methyl-1-oxobutan-2-yl)-6-(2,5-dioxo-2,5-
dihydro-1H-pyrrol-1-yl)hexanamide (24)

To a mixture of the mc-val-ala-OH (50 mg, 0.129 mmol) in 5% methanol in dichloromethane (1 mL) at 0° C. was added EEDQ (32 mg, 0.129 mmol). The mixture was stirred for 15 min, and then a solution of the aniline (44 mg, 0.044 mmol) in 5% methanol in dichloromethane (1 mL) was added. The reaction mixture was allowed to stir for 3 hours, was diluted with dichloromethane (2 mL) and was aspirated directly onto a 2 mm radial chromatotron plate. The product was eluted with a gradient of 2.5% to 5% methanol in dichloromethane to give 22.5 mg (40%): LC-MS: m/z (ES+) found 1294 (M+H)⁺.

Example 9—Preparation of PBD Dimer Conjugates

Antibodies with introduced cysteines: Antibodies to CD70 containing a cysteine residue at position 239 of the heavy chain were fully reduced by adding 10 equivalents of TCEP and 1 mM EDTA and adjusting the pH to 7.4 with 1M Tris buffer (pH 9.0). Following a 1 hour incubation at 37° C., the reaction was cooled to 22° C. and 30 equivalents of dehydroascorbic acid were added to selectively reoxidize the native disulfides, while leaving cysteine 239 in the reduced state. The pH was adjusted to 6.5 with 1M Tris buffer (pH 3.7) and the reaction was allowed to proceed for 1 hour at 22° C. The pH of the solution was then raised again to 7.4 by addition of 1 M Tris buffer (pH 9.0). 3.5 equivalents of the PBD drug linker in DMSO were placed in a suitable container for dilution with propylene glycol prior to addition to the reaction. To maintain solubility of the PBD drug linker, the antibody itself was first diluted with propylene glycol to a final concentration of 33% (e.g., if the antibody solution was in a 60 mL reaction volume, 30 mL of propylene glycol was added). This same volume of propylene glycol (30 mL in this example) was then added to the PBD drug linker as a diluent. After mixing, the solution of PBD drug linker in propylene glycol was added to the antibody solution to effect the conjugation; the final concentration of propylene glycol is 50%. The reaction was allowed to proceed for 30 minutes and then quenched by addition of 5 equivalents of N-acetyl cysteine. The ADC was then purified by ultrafiltration through a 30 kD membrane. (Note that the concentration of propylene glycol used in the reaction can be reduced for any particular PBD, as its sole purpose is to maintain solubility of the drug linker in the aqueous media.)

Example 10: Determination of In Vitro Activity of Selected Conjugates

The in vitro cytotoxic activity of the selected antibody drug conjugate was assessed using a resazurin (Sigma, St. Louis, Mo., USA) reduction assay (reference: Doronina et al., *Nature Biotechnology*, 2003, 21, 778-784). The antibody drug conjugate was prepared as described above.

For the 96-hour assay, cells cultured in log-phase growth were seeded for 24 h in 96-well plates containing 150 µL RPMI 1640 supplemented with 20% FBS. Serial dilutions of ADC in cell culture media were prepared at 4× working concentration; 50 µL of each dilution was added to the 96-well plates. Following addition of ADC, the cells were incubated with test articles for 4 days at 37° C. Resazurin was then added to each well to achieve a 50 µM final concentration, and the plates were incubated for an additional 4 hours at 37° C. The plates were then read for the extent of dye reduction on a Fusion HT plate reader (Packard Instruments, Meridien, Conn., USA) with excitation and emission wavelengths of 530 and 590 nm, respectively. The IC₅₀ value, determined in triplicate, is defined here as the concentration that results in a 50% reduction in cell growth relative to untreated controls.

Referring to the table below, the in vitro cytotoxicity of the ADC using the 96 hour assay is shown. The ADC was tested against antigen positive and antigen negative cell lines. h1F6 is the humanized anti-CD70 antibody described below.

In Vitro Activity

TABLE 1

| | IC$_{50}$ in pM following 48 hours treatment | | | |
|---|---|---|---|---|
| compound | 786-O | Caki-1 | HL60 | HEL9217 |
| 17 | 7 | 2 | 3 | 2 |
| 23 | 100 | 100 | 40 | 100 |

TABLE 2

| | | IC$_{50}$ in pM following 96 hours treatment | | |
|---|---|---|---|---|
| ADC | drugs/Ab | 786-O | Caki-1 | antigen-negative cell line |
| h1F6ec-6 | 1.8 | 260 | 12 | 28,000 |
| h1F6ec-9 | 1.5 | 120 | 4.9 | 60,000 |
| h1F6ec-14 | 1.8 | 380 | 24 | 20,000 |

TABLE 3

| | | IC$_{50}$ in pM following 96 hours treatment | | | |
|---|---|---|---|---|---|
| ADC | drugs/Ab | 786-O | Caki-1 | UMRC3 | antigen-negative cell line |
| h1F6ec-18 | 1.9 | 540 | 63 | 1000 | 4000 |
| h1F6ec-19 | 1.9 | 13 | 3.8 | 25 | 2000 |
| h1F6ec-24 | 2.0 | 30 | 8 | — | 3000 |

Example 11: Determination of In Vivo Cytotoxicity of Selected Conjugates

All studies were conducted in accordance with the Animal Care and Use Committee in a facility that is fully accredited by the Association for Assessment and Accreditation of Laboratory Animal Care. ADC tolerability was first assessed to ensure that the conjugates were tolerated at the doses selected for the xenograft experiments. BALB/c mice were treated with escalating doses of ADC formulated in PBS with 0.5 M arginine and 0.01% Tween 20. Mice were monitored for weight loss and outward signs of morbidity following treatment; those that experienced greater than 20% weight loss or displayed signs of morbidity were euthanized. The antibody used was a CD70 antibody, humanized h1F6 IgG1 (WO2006/113909 incorporated by reference in its entirety and for all purposes), with a point mutation substituting cysteine for serine at position 239. Conjugation to the Drug Unit is through the introduced cysteine at position 239. An average of 2 drugs is loaded per antibody.

In vivo therapy experiments were conducted in xenograft models in mice bearing CD70+ renal cell carcinoma. Tumor (Caki-1) fragments were implanted into the right flank of Nude mice. Mice were randomized to study groups (n=5 (786-0) with each group averaging around 100 mm³. The ADC or controls were dosed ip according to the schedule indicated. Tumor volume as a function of time was determined using the formula (L×W²)/2. Animals were euthanized when tumor volumes reached 1000 mm³. Mice showing durable regressions were terminated around day 100 post implant.

Referring to the FIGURE, the results of a treatment study using an h1F6-compound 18 and h1F6-compound 19 conjugate in a CD70+ renal cell carcinoma model are shown. Dosing was carried out at q7d×2. In the Figure, ✶ is untreated, ■ is treatment with h1F63c-18 at 0.1 mg/kg, □ is treatment with h1F63c-18 at 0.3 mg/kg, ▲ is treatment with h1F63c-19 at 1 mg/kg, ∆ is treatment with h1F63c-19 at 3 mg/kg.

Results of a mouse tolerability experiment an h1F6-compound 6 conjugate demonstrated that a single dose of ADC at 1 mg/kg was well tolerated with no signs of weight loss or morbidity out to 30 days. Administration of a higher dose (2.5 mg/kg) resulted in weight loss.

The invention claimed is:

1. A conjugate of formula I:

$$L\text{-}(LU\text{-}D)_p, \quad (I)$$

or a pharmaceutically acceptable salt thereof, wherein

L is a Ligand Unit selected from the group consisting of an antibody, an antigen-binding fragment of an antibody and an Fc fusion protein;

LU is a Linker Unit of formula 1a:

$$\text{-}A^1\text{-}L^1\text{-} \quad (1a)$$

wherein:

$L^1$ is an amino acid sequence comprising a dipeptide of formula —NH—$X_1$—$X_2$—CO—, wherein —NH— is the amino group of $X_1$, and CO is the carbonyl group of $X_2$, and wherein the peptide is cleavable by the action of an enzyme to release D as a free drug, wherein the enzyme is a cathepsin;

$A^1$ is a Stretcher Unit, wherein $A^1$ comprises the functionality —CO— connected directly to the amino group of $X_1$, thereby forming an amide link with —$X_1$—, and wherein $A_1$ is further comprised of the structure of:

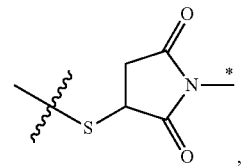

wherein

S is a sulfur atom derived from the Ligand Unit;

the wavy line indicates the point of attachment to the Ligand Unit; and the asterisk indicates the point of attachment to the remaining portion of $A^1$;

subscript p is from 1 to 20; and

D is a Drug Unit, wherein the Drug Unit is a PBD dimer having the structure selected from the group consisting of D1-D6:

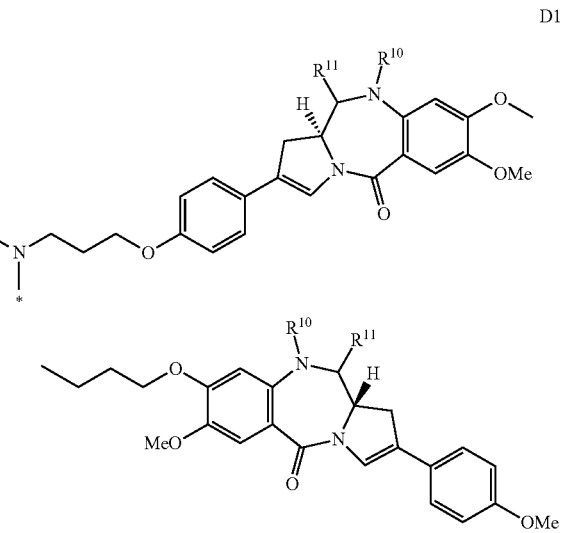

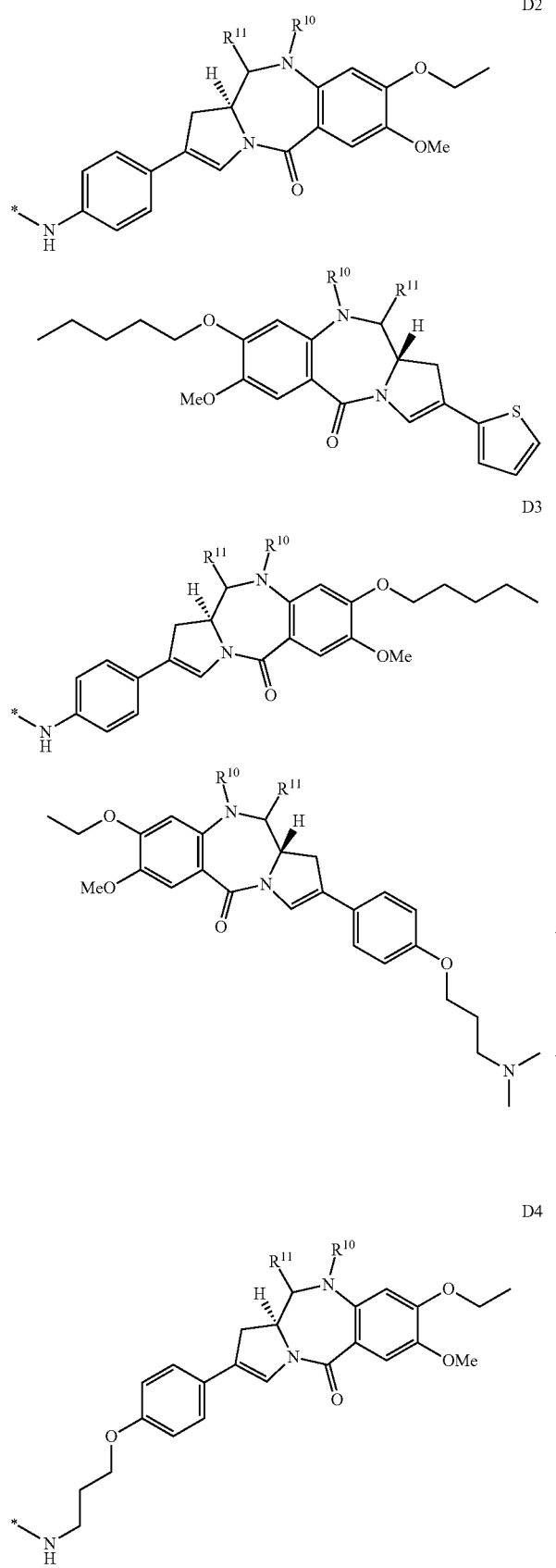
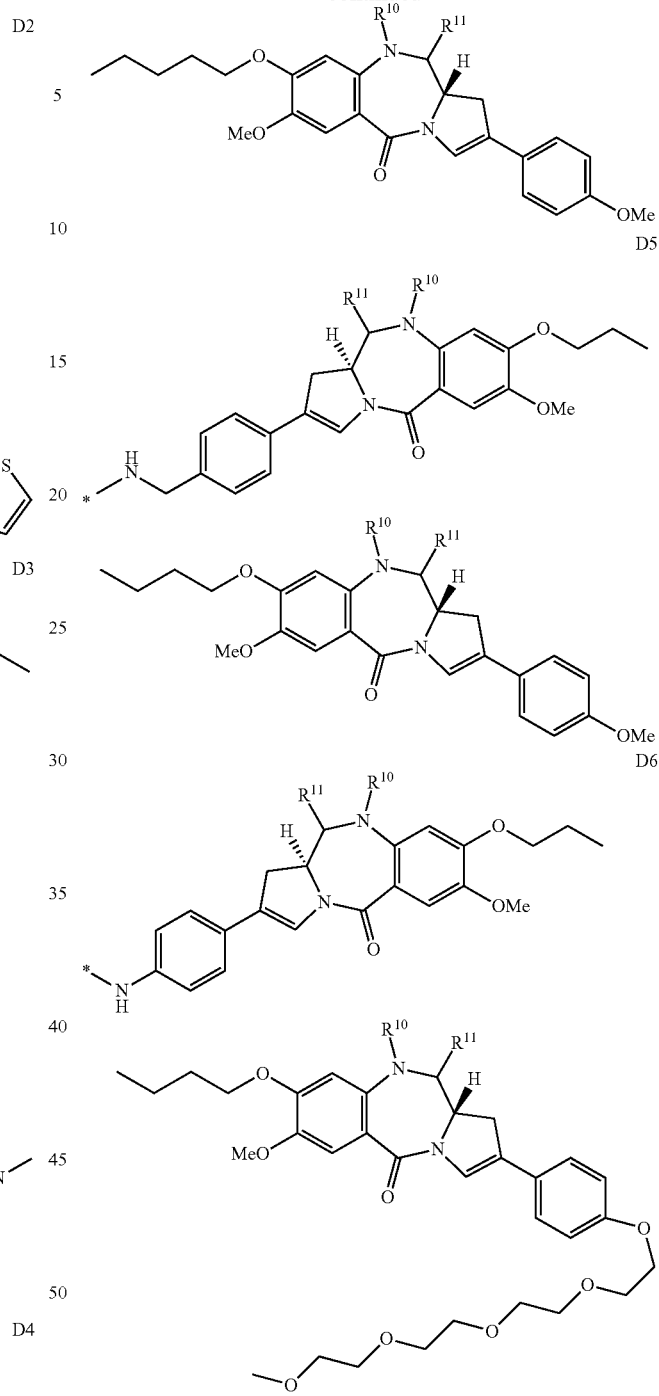
wherein the asterisk indicates the point of attachment to LU; and
either:
(a) $R^{10}$ is H, and $R^{11}$ is OH or $OR^A$, wherein $R^A$ is $C_{1-4}$ alkyl, or
(b) $R^{10}$ and $R^{11}$ form a nitrogen-carbon double bond between the nitrogen and carbon atoms to which they are bound, or
(c) $R^{10}$ is H and $R^{11}$ is $SO_zM$, wherein subscript z is 2 or 3 and M is a pharmaceutically acceptable cation;

and R¹⁰' and R¹¹' are the same as R¹⁰ and R¹¹, wherein if R¹¹ and R¹¹' are each SO_zM, then each M is an independently selected pharmaceutically acceptable monovalent cation or both M together is a pharmaceutically acceptable divalent cation.

2. The conjugate of claim 1, wherein R¹⁰ and R¹¹ form a nitrogen-carbon double bond.

3. The conjugate of claim 2, wherein R¹⁰' and R¹¹' form a nitrogen-carbon double bond.

4. The conjugate of claim 1, wherein the dipeptide of formula —NH—X₁—X₂—CO— is selected from the group consisting of -Phe-Lys-, -Val-Ala-, -Val-Lys-, -Ala-Lys-, -Val-Cit-, -Phe-Cit-, -Leu-Cit-, -Ile-Cit-, -Phe-Arg-, and -Trp-Cit-, wherein Cit is citrulline.

5. The conjugate of claim 1, wherein the Ligand Unit is an antibody or antigen binding fragment thereof and wherein the sulfur atom bonding the antibody Ligand Unit to A¹ of LU is from a reactive thiol group of a cysteine residue of the antibody or antigen binding fragment thereof.

6. The conjugate of claim 5, wherein the cysteine residue is an introduced cysteine residue in the heavy chain or light chain of the antibody or antigen binding fragment thereof.

7. The conjugate of claim 6, wherein the introduced cysteine is at amino acid heavy chain position 239 of the antibody, according to the EU numbering system.

8. The conjugate of claim 5, wherein the antibody is a humanized 1F6 antibody.

9. The conjugate of claim 7, wherein the antibody is a humanized 1F6 antibody.

10. A drug linker compound of formula V:

LU-D    (V)

or a salt thereof, wherein
LU is a Linker Unit having the formula of G¹-L¹, wherein
  L¹ is an amino acid sequence comprising a dipeptide of formula —NH—X₁—X₂—CO—, wherein —NH— is the amino group of X₁, and CO is the carbonyl group of X₂, and wherein the peptide is cleavable by the action of an enzyme to release D as a fee drug, wherein the enzyme is a cathepsin;
  G¹ is a Stretcher Unit for connection to a Ligand Unit, wherein G¹ is comprised of a maleimide group for reaction with a reactive thiol functional group provided by the Ligand Unit for said connection, and wherein G¹ further comprises the functionality —CO— connected directly to the amino group of X₁, thereby forming an amide link with —X₁—;
D is a Drug Unit, wherein the Drug Unit is a PBD dimer having the structure selected from the group consisting of D1-D6:

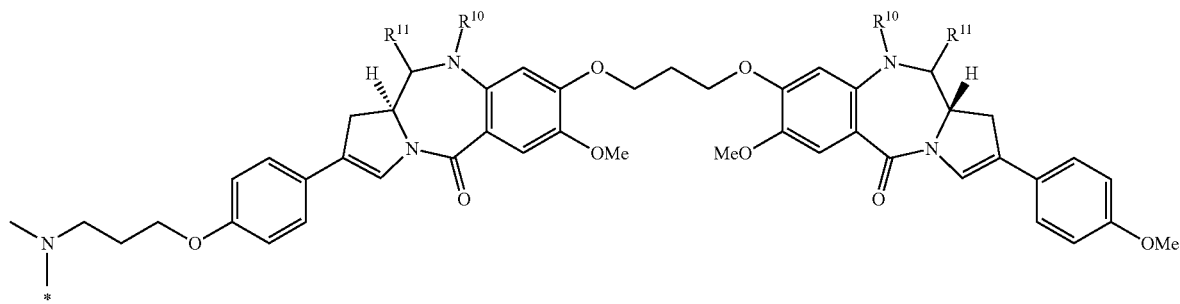

D1

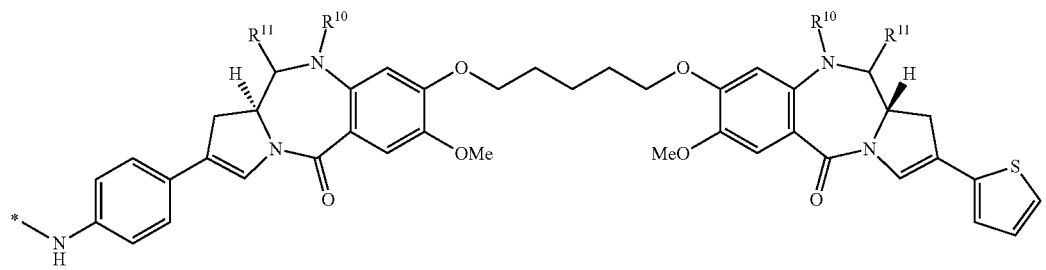

D2

-continued
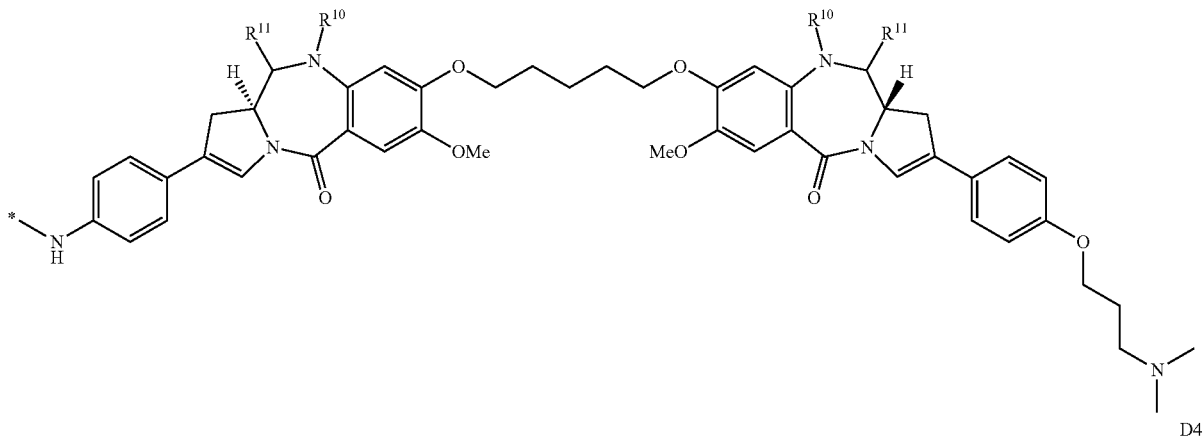
D3
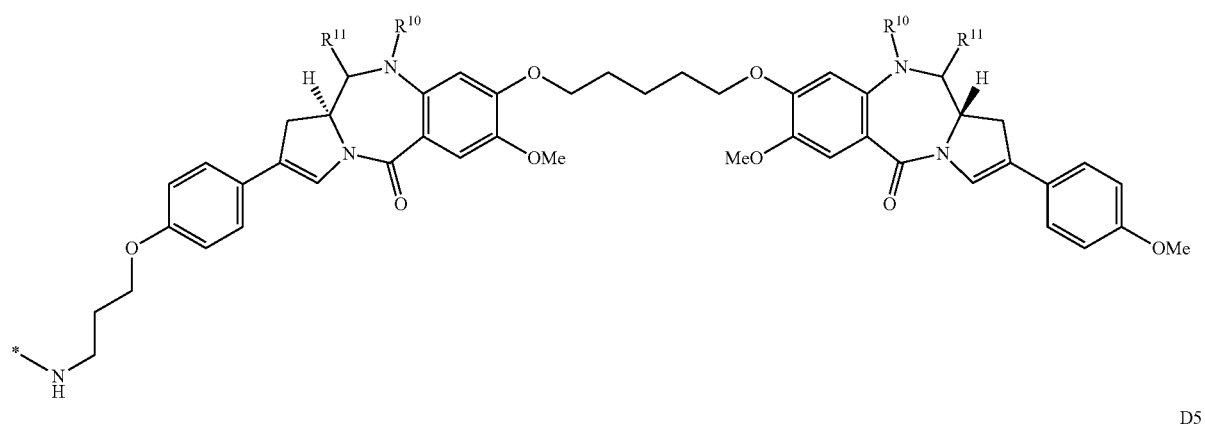
D4
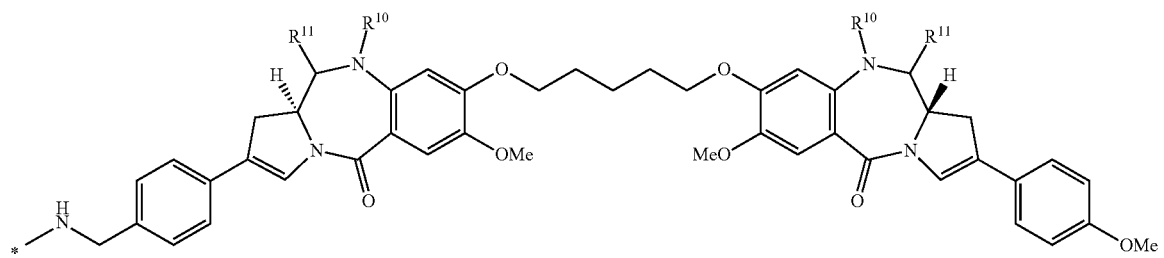
D5
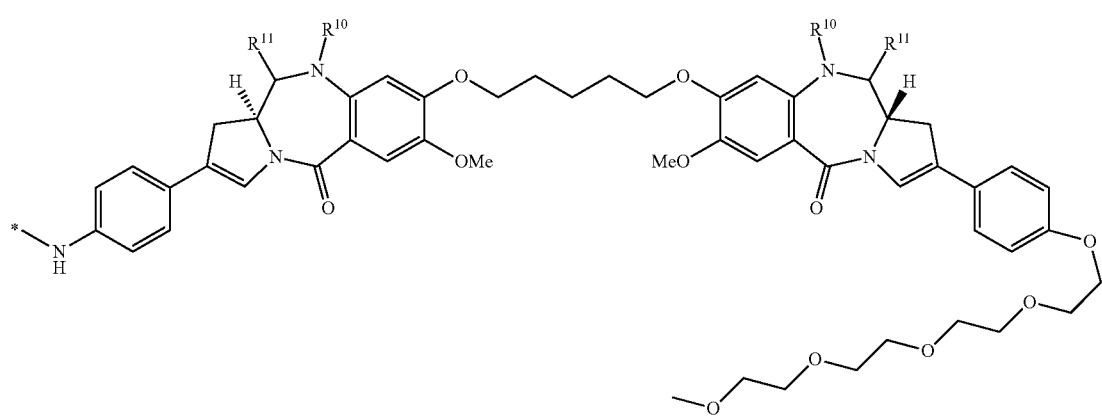
D6 and salts thereof, wherein
the asterisk indicates the point of attachment to LU; and either:
(a) $R^{10}$ is H, and $R^{11}$ is OH or $OR^A$, wherein $R^A$ is $C_{1-4}$ alkyl, or
(b) $R^{10}$ and $R^{11}$ form a nitrogen-carbon double bond between the nitrogen and carbon atoms to which they are bound, or
(c) $R^{10}$ is H and $R^{11}$ is $SO_zM$, wherein subscript z is 2 or 3 and M is a cation; and $R^{10'}$ and $R^{11'}$ are the same as $R^{10}$ and $R^{11}$, wherein if $R^{11}$ and $R^{11'}$ are each $SO_zM$, then each M is an independently selected monovalent cation or both M together is a divalent cation.

11. The drug linker compound of claim 10, wherein the dipeptide of formula —NH—$X_1$—$X_2$—CO— is selected from the group consisting of -Phe-Lys-, -Val-Ala-, -Val-Lys-, -Ala-Lys-, -Val-Cit-, -Phe-Cit-, -Leu-Cit-, -Ile-Cit-, -Phe-Arg-, and -Trp-Cit-, wherein Cit is citrulline.

12. The drug linker compound of claim 10, wherein $R^{10}$ and $R^{11}$ form a nitrogen-carbon double bond.

13. The drug linker compound of claim 12, wherein $R^{10'}$ and $R^{11'}$ form a nitrogen-carbon double bond.

14. The drug linker compound of claim 13, wherein $L^1$ is a dipeptide selected from the group consisting of valine-alanine, valine-citrulline and phenylalanine-lysine.

15. A method of preparing an antibody drug conjugate of claim 1 in which L is an antibody Ligand Unit,
the method comprising the step of contacting an antibody having a reactive cysteine thiol functional group with a Drug Linker compound of claim 10 so that the sulfur atom of the reactive thiol functional group reacts with the maleimide group of $G^1$ of the Drug Linker compound to form the Stretcher Unit ($A^1$) of the antibody drug conjugate,
wherein the reactive thiol functional group is obtained by disulfide reduction of the antibody or by introduction of a cysteine residue in the heavy chain of the antibody.

* * * * *